United States Patent
Inada et al.

(10) Patent No.: US 10,040,754 B2
(45) Date of Patent: Aug. 7, 2018

(54) CELLULOSE ACYLATE FILM, NOVEL COMPOUND, POLARIZING PLATE AND LIQUID CRYSTAL DISPLAY DEVICE

(71) Applicant: FUJIFILM Corporation, Tokyo (JP)

(72) Inventors: Hiroshi Inada, Kanagawa (JP); Naozumi Shiraiwa, Kanagawa (JP); Yingjie Xu, Kanagawa (JP); Aiko Yoshida, Kanagawa (JP); Masaki Noro, Kanagawa (JP); Yasukazu Kuwayama, Kanagawa (JP); Nobutaka Fukagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 347 days.

(21) Appl. No.: 14/835,165

(22) Filed: Aug. 25, 2015

(65) Prior Publication Data

US 2015/0361036 A1 Dec. 17, 2015

Related U.S. Application Data

(63) Continuation of application No. PCT/JP2014/054762, filed on Feb. 26, 2014.

(30) Foreign Application Priority Data

Feb. 26, 2013 (JP) .................. 2013-035377
Jul. 26, 2013 (JP) .................. 2013-156149
Jul. 26, 2013 (JP) .................. 2013-156160

(51) Int. Cl.
*C07C 271/20* (2006.01)
*C07C 271/06* (2006.01)
(Continued)

(52) U.S. Cl.
CPC .......... *C07C 271/20* (2013.01); *C07C 271/06* (2013.01); *C07C 271/28* (2013.01);
(Continued)

(58) Field of Classification Search
None
See application file for complete search history.

(56) References Cited

U.S. PATENT DOCUMENTS 3,846,442 A 11/1974 Habermeier et al.
3,867,347 A 2/1975 Felber et al.
(Continued)

FOREIGN PATENT DOCUMENTS

CN 101445577 A 6/2009
CN 103709449 A 4/2014
(Continued)

OTHER PUBLICATIONS

Written Opinion issued in connection with International Patent Application No. PCT/JP2014/069823 dated Oct. 21, 2014.
(Continued)

*Primary Examiner* — Anthony J Frost
(74) *Attorney, Agent, or Firm* — Edwards Neils LLC; Jean C. Edwards, Esq.

(57) ABSTRACT

A cellulose acylate film, which includes a compound denoted by general formula (I) below, the equivalent U of which, calculated as a value obtained by dividing the molecular weight of the compound by the number of divalent linking groups denoted by —O—C(=O)—NH— contained per molecule, is less than or equal to 515, wherein, in general formula (I), each of $L^{11}$ and $L^{21}$ independently denotes an optionally substituted alkylene group; each of $L^{12}$ and $L^{22}$ independently denotes a single bond, any one of or any combination of —O—, —$NR^1$—, —S— and —C(=O)—; $R^1$ denotes a hydrogen atom or a substituent; each of n1 and n2 independently denotes an integer of 0 to 20, with at least either n1 or n2 being an integer of greater than or equal to 1.

$Q^1\text{-}(L^{12}\text{-}L^{11})_{n1}\text{-}O\text{—}C(=O)\text{—}NH\text{-}(L^{21}\text{-}L^{22})_{n2}\text{-}Q^2$    General formula (I)

16 Claims, 1 Drawing Sheet

(51) Int. Cl.

| | | |
|---|---|---|
| C07C 271/28 | (2006.01) | |
| C07C 271/36 | (2006.01) | |
| C07C 271/56 | (2006.01) | |
| C07D 295/20 | (2006.01) | |
| C08J 5/18 | (2006.01) | |
| C08K 5/16 | (2006.01) | |
| G02B 1/14 | (2015.01) | |
| G02B 5/30 | (2006.01) | |

(52) U.S. Cl.
CPC ......... *C07C 271/36* (2013.01); *C07C 271/56* (2013.01); *C07D 295/20* (2013.01); *C08J 5/18* (2013.01); *C08K 5/16* (2013.01); *G02B 1/14* (2015.01); *G02B 5/30* (2013.01); *B32B 2457/202* (2013.01); *C08J 2301/10* (2013.01); *Y10T 428/1041* (2015.01); *Y10T 428/31971* (2015.04)

(56) References Cited

U.S. PATENT DOCUMENTS

| | | | |
|---|---|---|---|
| 4,019,972 | A | 4/1977 | Faust |
| 4,200,725 | A | 4/1980 | Gras et al. |
| 4,218,515 | A | 8/1980 | Heckles |
| 4,328,325 | A | 5/1982 | Marquardt et al. |
| 4,355,093 | A | 10/1982 | Hartmann et al. |
| 4,861,853 | A | 8/1989 | Petrie et al. |
| 4,931,529 | A | 6/1990 | Burba et al. |
| 4,968,732 | A | 11/1990 | Burba et al. |
| 4,983,676 | A | 1/1991 | Petrie et al. |
| 5,030,754 | A | 7/1991 | Speranza et al. |
| 6,726,995 | B2 | 4/2004 | Ishii et al. |
| 7,709,572 | B2 | 5/2010 | Takebe et al. |
| 8,690,305 | B2 | 4/2014 | Breton et al. |
| 2009/0119851 | A1 | 5/2009 | Steigerwald et al. |
| 2011/0223435 | A1* | 9/2011 | Naito ............... B29C 41/28 428/461 |
| 2012/0204757 | A1* | 8/2012 | Nagura ............... C09K 19/54 106/170.1 |
| 2012/0287199 | A1* | 11/2012 | Breton ............... B41J 2/17593 347/20 |
| 2015/0361036 | A1 | 12/2015 | Inada et al. |

FOREIGN PATENT DOCUMENTS

| | | |
|---|---|---|
| CN | 105026479 A | 11/2015 |
| DE | 10154350 A1 | 5/2003 |
| GB | 1453429 A | 10/1976 |
| GB | 1580864 A | 12/1980 |
| JP | S49-53691 A | 5/1974 |
| JP | S50-92124 A | 7/1975 |
| JP | S51-19601 A | 2/1976 |
| JP | S51-34265 A | 3/1976 |
| JP | S53-285 A | 1/1978 |
| JP | S54-44670 A | 4/1979 |
| JP | S55-137118 A | 10/1980 |
| JP | S55-157623 A | 12/1980 |
| JP | S56-165146 A | 12/1981 |
| JP | S58-187187 A | 11/1983 |
| JP | S60-104055 A | 6/1985 |
| JP | S64-75515 A | 3/1989 |
| JP | H01-101325 A | 4/1989 |
| JP | H02-19362 A | 1/1990 |
| JP | H05-197073 A | 8/1993 |
| JP | 2001-187806 A | 7/2001 |
| JP | 2004-026742 A | 1/2004 |
| JP | 2004-155934 A | 6/2004 |
| JP | 2004-175971 A | 6/2004 |
| JP | 2004-292696 A | 10/2004 |
| JP | 2005-242566 A | 9/2005 |
| JP | 2005-272485 A | 10/2005 |
| JP | 2005-272566 A | 10/2005 |
| JP | 2005272566 A * | 10/2005 |
| JP | 2006-257369 A | 9/2006 |
| JP | 2009-015045 A | 1/2009 |
| JP | 2009-241397 A | 10/2009 |
| JP | 2009-258410 A | 11/2009 |
| JP | 2012-123292 A | 6/2012 |
| JP | 2012-236998 A | 12/2012 |
| JP | 2013-020223 A | 1/2013 |
| JP | 2013-076000 A | 4/2013 |
| WO | 2007/008959 A2 | 1/2007 |
| WO | 2011/059994 A2 | 5/2011 |
| WO | WO 2013/133041 A1 | 9/2013 |
| WO | 2014/171468 A1 | 10/2014 |
| WO | 2015/012407 A1 | 1/2015 |

OTHER PUBLICATIONS

International Search Report issued in connection with International Patent Application No. PCT/JP2014/069823 dated Oct. 21, 2014.
International Preliminary Report on Patentability issued by WIPO dated Oct. 29, 2015, in connection with Intl. Patent Application No. PCT/JP2014/060786.
International Preliminary Report on Patentability issued by WIPO dated Feb. 4, 2016, in connection with Related International Patent Application No. PCT/JP2014/069823.
International Search Report issued in PCT/JP2014/054762 dated Apr. 1, 2014.
Written Opinion issued in PCT/JP2014/054762 dated Apr. 1, 2014.
Second Office Action issued by the State Intellectual Property Office (SIPO) of China dated Aug. 23, 2017 in connection with Chinese Patent Application No. 201480041133.1.
Office Action, issued by the Japanese Patent Office (JPO) dated Sep. 5, 2017 in connection with Japanese Patent Application No. 2015-121383.
First Office Action issued by the State Intellectual Property Office (SIPO) of China dated Nov. 28, 2016 in connection with corresponding Chinese Patent Application No. 201480041133.1.
Xiong Quanbo et al., The Seminar of Application Technique is Foreseen to the Plastic Lining, Open Day Apr. 30, 2009, pp. 61-66.
Office Action, issued by the Japanese Patent Office (JPO) dated August 30, 2016, in connection with corresponding Japanese Patent Application No. 2015-502995.
J. Malik et al., Computational study of thermally controlled polymer network disassembly via the incorporation of sterically hindered urea linkages, Polymer, 2002, pp. 2561-2567, vol. 43 No. 8, Dept. of Materials Science and Engineering, University of Cincinnati, Cincinnati, Ohio.
J. Malik et al., Thermally Controlled Molecular Disassembly of a Crosslinked Polymer Network by the Incorporation of Sterically Hindered Urea Linkages, Journal of Applied Polymer Science, 2002, pp. 856-864, vol. 85 No. 4, Dept. of Materials Science and Engineering, University of Cincinnati, Cincinnati, Ohio.
Office Action, issued by the State Intellectual Property Office (SIPO) of China dated Jun. 29, 2016, in connection with corresponding Chinese Patent Application No. 201480010577.9.
International Search Report dated Jul. 8, 2014 in connection with International Patent Application No. PCT/JP2014/060786.
Written Opinion of the ISA dated Jul. 8, 2014 in connection with International Patent Application No. PCT/JP2014/060786 dated Jul. 8, 2014.
Notification of Reasons for Refusal issued by the Japanese Patent Office dated Dec. 6, 2016, in connection with Japanese Patent Application No. 2014-081511.
International Preliminary Report on Patentability issued by WIPO dated Sep. 1, 2015 in connection with Intl. Patent Application No. PCT/JP2014/054762.
Second Office Action issued by the State Intellectual Property Office (SIPO) of China dated Mar. 2, 2017 in connection with corresponding Chinese Patent Application No. 201480010577.9.
Non-Final Office Action, issued by the USPTO dated Dec. 6, 2017, in connection with U.S. Appl. No. 14/843,723.

(56) References Cited

OTHER PUBLICATIONS

Non-Final Office Action, issued by the USPTO dated Mar. 29, 2018, in connection with U.S. Appl. No. 14/884,314.

* cited by examiner

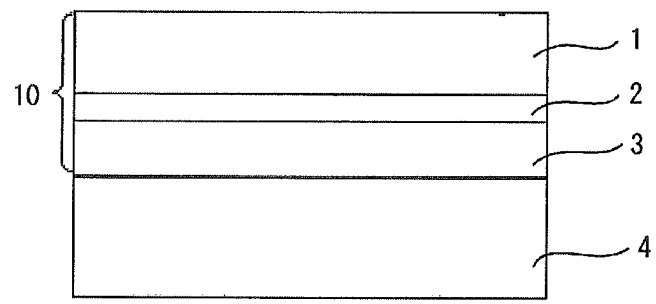

CELLULOSE ACYLATE FILM, NOVEL COMPOUND, POLARIZING PLATE AND LIQUID CRYSTAL DISPLAY DEVICE

CROSS-REFERENCE TO RELATED APPLICATIONS

This application is a Continuation of PCT International Application No. PCT/JP2014/54762 filed on Feb. 26, 2014, which was published under PCT Article 21(2) in Japanese, and claims priority under 35 U.S.C § 119(a) to Japanese Patent Application No. 2013-035377 filed on Feb. 26, 2013, Japanese Patent Application No. 2013-156149 filed on Jul. 26, 2013, and Japanese Patent Application No. 2013-156160 filed on Jul. 26, 2013. The above applications are hereby expressly incorporated by reference, in their entirety, into the present application.

TECHNICAL FIELD

The present invention relates to a cellulose acylate film, a polarizing plate, and a liquid crystal display device. In particular, the present invention relates to a cellulose acylate film that is useful as a polarizing plate protective film, a polarizing plate employing the same, and a liquid crystal device comprising the polarizing plate.

The present invention further relates to a novel compound that is useful as an additive for cellulose acylate films.

BACKGROUND ART

Cellulose acylate films are generally employed as optical compensation films, protective films, substrate films, and the like in display devices such as liquid crystal display devices. Patent References 1 and 2, for example, propose adding additives to enhance the performance of such cellulose acylate films.

Patent Reference 1: JP-A-No. 2004-175971; Patent Reference 2: JP-A-No. 2005-272566

SUMMARY OF THE INVENTION

Patent Reference 1 describes additives for enhancing the ductility of the film. However, when the present inventors examined the additives described in Patent Reference 1, they found that due to absorption at 275 nm or longer, there was a problem that the film tends to be yellowish accompanied by continuous light irradiation (referred to as "light tinting" hereinafter). Patent Reference 2 describes additives for increasing retardation in the direction of thickness (Rth) of the film. However, when the film is rendered thin, there was a possibility of an increase in haze of the film due to volatilization.

In light of these points, in additives for cellulose acylate films, there is a need for not having an influence on light tinting and for having low-volatility.

In recent years, display devices mainly for television use have been increasing in size and becoming thinner. Therefore, a need to reduce the thickness of the cellulose acylate film constituting the display device has been increasing. In this regard, research conducted by the present inventors has revealed that in a liquid crystal display device of reduced thickness, the surface hardness of the film has a significant impact on the performance of the liquid crystal display device. More specifically, the surface hardness of the protective film that is employed on the viewer-side of the polarizing plate was found to have a particularly significant impact on the performance of the liquid crystal display device.

However, although Patent Reference 1 states that the overall physical strength of a cellulose acylate film can be increased by adding the additives that are described therein, there is no disclosure relating to enhanced surface hardness. Nor is there any disclosure regarding the mechanical characteristics of the film in Patent Reference 2.

In an aspect of the present invention, for resolving such problems of conventional art, the object is to provide a cellulose acylate film in which light tinting is inhibited, volatilization of additives is low, and has enough surface hardness.

Based on the above-stated object, the present inventors conducted extensive research. As a result, they discovered that in the first and second aspects described in detail further below, adding a compound having a specific structure to the cellulose acylate film made it possible to enhance the surface hardness of the cellulose acylate film and provide a cellulose acylate film of reduced thickness having a surface of great hardness. In this regard, the present inventors surmise that in the first aspect, described further below, the compound having a urethane bond (a bond denoted by —O—C(=O)—NH—) in a prescribed ratio and having a specific structure interacted with a local moiety such as an ester bond or hydroxyl group in the cellulose acylate, or with the polymer chain, and thus reducing the interspace of the film, thereby increasing the surface hardness of the cellulose acylate film. The present inventors surmise that in the second aspect, a prescribed divalent linking group contained in the compound described further below interacted with a local moiety such as an ester body or hydroxyl group in the cellulose acylate, or with the polymer chain, reducing the interspace of the film and thus increasing the surface hardness of the cellulose acylate film. Even more surprisingly, these compounds were found to having low-volatility, and the film to which these compounds were added inhibited light tinting.

The present invention was devised based on the above knowledge.

An aspect (the first aspect) of the present invention relates to a cellulose acylate film comprising the compound denoted by general formula (I) below, the equivalent U of which ((molecular weight)/(number of divalent linking groups denoted by —O—C(=O)—NH— contained per molecule)), calculated as the value obtained by dividing the molecular weight of the compound by the number of divalent linking groups denoted by —O—C(=O)—NH— contained per molecule, is less than or equal to 515:

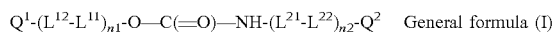

$$Q^1\text{-}(L^{12}\text{-}L^{11})_{n1}\text{-}O\text{-}C(=O)\text{-}NH\text{-}(L^{21}\text{-}L^{22})_{n2}\text{-}Q^2 \quad \text{General formula (I)}$$

(wherein, in general formula (I), each of $L^{11}$ and $L^{21}$ independently denotes an optionally substituted alkylene group; each of $L^{12}$ and $L^{22}$ independently denotes a single bond, any one of or any combination of —O—, —NR$^1$—, —S—, and —C(=O)—; R$^1$ denotes a hydrogen atom or a substituent;

each of n1 and n2 independently denotes an integer of 0 to 20, with at least either n1 or n2 being an integer of greater than or equal to 1; when $L^{11}$, $L^{12}$, $L^{21}$, and $L^{22}$ are present in a plurality of number, the plurality of $L^{11}$, $L^{12}$, $L^{21}$, and $L^{22}$ can be identical or different; and each of $Q^1$ and $Q^2$ independently denotes a substituent, with at least either $Q^1$ or $Q^2$ comprising a ring structure).

In one embodiment, the compound denoted by general formula (I) comprises 1 to 6 divalent linking groups denoted by —O—C(=O)—NH— per molecule.

In one embodiment, the molecular weight of the compound denoted by general formula (I) falls within a range of 230 to 2,000.

In one embodiment, the compound denoted by general formula (I) is a compound denoted by general formula (I-1) below:

$$(Q^3\text{-}(L^{32}\text{-}L^{31})_{n3}\text{-}A\text{-}(L^{41}\text{-}L^{42})_{n4})_m\text{-}Z^1 \qquad \text{General formula (I-1):}$$

(wherein, in general formula (I-1), each of $L^{31}$ and $L^{41}$ independently denotes an optionally substituted alkylene group; each of $L^{32}$ and $L^{42}$ independently denotes a single bond, any one of or any combination of —O—, —NR$^1$—, —S—, and —C(=O)—; R$^1$ denotes a hydrogen atom or a substituent; each of n3 and n4 independently denotes an integer of 0 to 20, with at least either n3 or n4 being an integer of greater than or equal to 1; when $L^{31}$, $L^{32}$, $L^{41}$, and $L^{42}$ in a plurality of number, the plurality of $L^{31}$, $L^{32}$, $L^{41}$, and $L^{42}$ can be identical or different; $Q^3$ denotes a substituent; $Z^1$ denotes a linking group of valence m; A denotes *—O—C(=O)—NH— or *—NH—C(=O)—O—, where * denotes the position of the bond with $L^{41}$; m denotes an integer of 2 to 6; when $Q^3$ and A are present in a plurality of number, the plurality of $Q^3$ and A can be identical or different; with at least either $Q^3$ or $Z^1$ comprising a ring structure).

In one embodiment, at least either $Q^3$ or $Z^1$ in the compound denoted by general formula (I-1) comprises a ring structure, the compound denoted by general formula (I-1) has 2 or 3 ring structures per molecule.

In one embodiment, in general formula (I-1), at least one of the plurality of $Q^3$ comprises an aromatic group, or $Z^1$ comprises a alicyclic group or aromatic group.

In one embodiment, in general formula (I-1), at least one of the plurality of $Q^3$ comprises an aromatic group or $Z^1$ comprises a alicyclic group.

In one embodiment, the compound denoted by general formula (I) is a compound denoted by general formula (I-2) below:

$$(Q^4\text{-}(L^{52}\text{-}L^{51})_{n5}\text{-}A\text{-}(L^{61}\text{-}L^{62})_{n6})_{m1}\text{-}Z^2 \qquad \text{General formula (I-2):}$$

(wherein, in general formula (I-2), each of $L^{51}$ and $L^{61}$ independently denotes an optionally substituted alkylene group; each of $L^{52}$ and $L^{62}$ independently denotes a single bond, or any one of or any combination of —O—, —NR$^1$—, —S—, and —C(=O)—; R$^1$ denotes a hydrogen atom or a substituent; each of n5 and n6 independently denotes an integer of 0 to 20, with at least either n5 or n6 being an integer of greater than or equal to 1; when $L^{51}$, $L^{52}$, $L^{61}$, and $L^{62}$ are present in a plurality of number, the plurality of $L^{51}$, $L^{52}$, $L^{61}$, and $L^{62}$ can be identical or different; $Q^4$ denotes a substituted or unsubstituted phenyl group, substituted or unsubstituted cyclohexyl group, methyl group, or t-butyl group; $Z^2$ denotes a group comprising at least one or any combination of linear, branched, and alicyclic group and aromatic group; A denotes *—O—C(=O)—NH— or *—NH—C(=O)—O—, where * denotes the position of the bond with $L^{61}$; m1 denotes the integer 2 or 3; when $Q^4$ and A are present in a plurality of number, the plurality of $Q^4$ and A can be identical or different; with at least one from among $Z^2$ and the plurality of $Q^4$ comprising a ring structure).

In one embodiment, in general formula (I-2), $L^{51}$ denotes an alkylene group and $L^{52}$ denotes a single bond or —O—.

In one embodiment, in general formula (I-2), $Q^4$ is an unsubstituted phenyl group.

In one embodiment, in general formula (I-2), $Z^2$ denotes a group comprising at least a alicyclic group or aromatic group.

In one embodiment, the compound denoted by general formula (I) is selected from the group consisting of the compound denoted by general formula (I-3) below, the compound denoted by general formula (I-4) below, and the compound denoted by general formula (I-5) below:

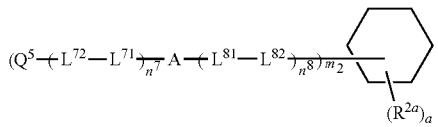

General formula (I-3)

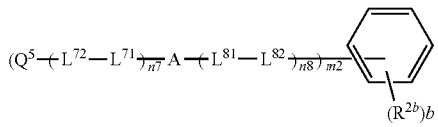

General formula (I-4)

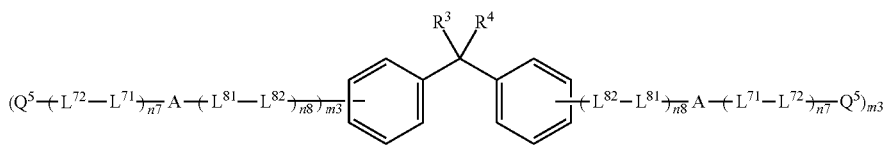

General formula (I-5)

(wherein each of $L^{71}$ and $L^{81}$ independently denotes an optionally substituted alkylene group; each of $L^{72}$ and $L^{82}$ independently denotes a single bond, any one any one of or any combination of —O—, —NR$^1$—, —S—, and —C(=O)—; R$^1$ denotes a hydrogen atom or a substituent; each of n7 and n8 independently denotes an integer of 0 to 20, with at least either n7 or n8 being an integer of greater than or equal to 1; when $L^{71}$, $L^{72}$, $L^{81}$, and $L^{82}$ are present in a plurality of number, the plurality of $L^{71}$, $L^{72}$, $L^{81}$, and $L^{82}$ can be identical or different; $Q^5$ denotes a substituted or unsubstituted phenyl group, substituted or unsubstituted cyclohexyl group, methyl group, or t-butyl group; A denotes *—O—C(=O)—NH— or *—NH—C(=O)—O—, where * denotes the position of the bond with $L^{81}$; each of $R^{2a}$ and $R^{2b}$ denotes an alkyl group having 1 to 3 carbon atoms; m2 denotes the integer 2 or 3; the plurality of $Q^5$ and A can be identical or different; a denotes an integer of 0 to 10; when a is an integer that is greater than or equal to 1, the plurality of $R^{2a}$ that are present can be identical or different; b denotes an integer of 0 to 5; when b is an integer that is greater than or equal to 1, the plurality of $R^{2b}$ can be identical or different; m3 denotes 1 or 2; the plurality of m3 can be identical or different; and each of $R^3$ and $R^4$ independently denotes a hydrogen atom or a methyl group).

In one embodiment, the compounded denoted by general formula (I) is selected from the group consisting of the compound denoted by general formula (II) below and the compound denoted by general formula (III) below:

General formula (II)

General formula (III)

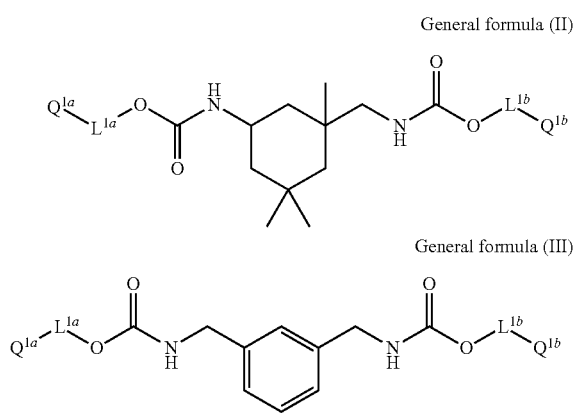

(wherein, in general formulas (II) and (III), each of $L^{1a}$ and $L^{1b}$ independently denotes a single bond, an alkylene group, one of the groups denoted by general formula (2A) to (2E) below, or a group comprised of a combination of 2 or 3 or any combination of the groups denoted by general formulas (2A) to (2E) and one or more alkylene groups; each of $Q^{1a}$ and $Q^{1b}$ independently denotes a substituent, with at least either $Q^{1a}$ or $Q^{1b}$ denoting a phenyl group optionally substituted with an alkoxy group having 1 to 3 carbon atoms or an alkyl group having 1 to 3 carbon atoms;

—{$R^b_{jb}(CR^aR^c)_{ja}$—O—(C=O)}—*;  General formula (2A)

—{$R^b_{jb}(CR^aR^c)_{ja}$—O}—*;  General formula (2B)

—{$R^b_{jb}(CR^aR^c)_{ja}$—(C=O)O—}—*;  General formula (2C)

—{$R^b_{jb}(CR^aR^c)_{ja}$—$NR^1$(C=O)O—}—*;  General formula (2D)

—{$R^b_{jb}(CR^aR^c)_{ja}$—O—(C=O)$NR^1$}—*;  General formula (2E)

wherein, in general formulas (2A) to (2E), * denotes the position of the bond with $Q^{1a}$ or $Q^{1b}$, or the position of the bond with an adjacent group on the $Q^{1a}$ or $Q^{1b}$ side; each of $R^a$ and $R^c$ independently denotes a hydrogen atom or an alkyl group having 1 to 3 carbon atoms; ja denotes an integer that is greater than or equal to 1; when $R^a$ and $R^c$ are present in a plurality of number, the plurality of $R^a$ and $R^c$ can be identical or different; $R^b$ denotes a cycloalkylene group optionally substituted with one or more alkyl groups having 1 to 3 carbon atoms; jb denotes 0 or 1; and $R^1$ denotes a hydrogen atom or an alkyl group having 1 to 4 carbon atoms; when $R^1$ are present in a plurality of number, the plurality of $R^1$ can be identical or different).

An aspect (the second aspect) of the present invention relates to a cellulose acylate film comprising a compound denoted by general formula (A-100) below:

$Q^A$-($L^{102}$-$L^{101}$)$_{na}$-$NR^{100}$—C(=O)—NH-($L^{103}$-$L^{104}$)$_{nb}$-$Q^B$  General formula (A-100)

(wherein, in general formula (A-100), $R^{100}$ denotes a hydrogen atom or a substituent; each of $L^{101}$ and $L^{102}$ independently denotes an optionally substituted alkylene group; each of $L^{102}$ and $L^{104}$ independently denotes a single bond, any one of or any combination of —O—, —$NR^{100a}$—, —S—, and —C(=O)—; $R^{100a}$ denotes a hydrogen atom or a substituent; each of na and nb independently denotes an integer of 0 to 20; when $L^{101}$, $L^{102}$, $L^{103}$, and $L^{104}$ are present in a plurality of number, the plurality of $L^{101}$, $L^{102}$, $L^{103}$, and $L^{104}$ can be identical or different; each of $Q^A$ and $Q^B$ independently denotes a substituent, with at least either $Q^A$ or $Q^B$ comprising a ring structure; when na denotes zero and $Q^A$ comprises a ring structure, the ring structure comprised in $Q^A$ can be one that is formed with $R^{100}$ in —$NR^{100}$—; however, the number of divalent linking groups denoted by —NH—(C=O)—NH— per molecule is 0 or 1).

In one embodiment, the compound denoted by general formula (A-100) comprises two or more divalent linking groups denoted by —NH—(C=O)—NR—, where R denotes a hydrogen atom or a substituent; or one or more each of the above divalent linking groups denoted by —NH—(C=O)—NR— and a divalent linking group denoted by —NH—C(=O)—O—, per molecule.

In one embodiment, the molecular weight of the compound denoted by general formula (A-100) falls within a range of 230 to 2000.

In one embodiment, the compound denoted by general formula (A-100) is a compound denoted by general formula (A-1) below:

$(Q^{103}$-($L^{132}$-$L^{131}$)$_{n103}$-$A^{100}$($L^{141}$-$L^{142}$)$_{n104}$)$_m$-$Z^{101}$  General formula (A-101)

(wherein, in general formula (A-101), each of $L^{131}$ and $L^{141}$ independently denotes an optionally substituted alkylene group; each of $L^{132}$ and $L^{142}$ independently denotes a single bond, any one of or any combination of —O—, —$NR^{100a}$—, —S—, and —C(=O)—; $R^{100a}$ denotes a hydrogen atom or a substituent; each of n103 and n104 independently denotes an integer of 0 to 20; when $L^{131}$, $L^{132}$, $L^{141}$, and $L^{142}$ are present in a plurality of number, the plurality of $L^{131}$, $L^{132}$, $L^{141}$, and $L^{142}$ can be identical or different; $Q^{103}$ denotes a substituent; $Z^{101}$ denotes a linking group of valence m; $A^{100}$ denotes *—NR—C(=O)—NH—, *—NH—C(=O)—NR—, *—O—C(=O)—NH—, or *—NH—C(=O)—O—; $R^{100}$ denotes a hydrogen atom or a substituent; * denotes the position of the bond with $L^{141}$ or $Z^{101}$; m denotes an integer of 2 to 6; the plurality of $Q^{103}$ and $A^{100}$ can be identical or different, with at least one of $A^{100}$ denoting *—NR—C(=O)—NH— or *—NH—C(=O)—$NR^{100}$—, and with at least one from among the plurality of $Q^{103}$ and $Z^{101}$ comprising a ring structure; and when at least one instance of n103 denotes zero, $Q^{103}$ comprises a ring structure, and $A^{100}$ denotes *—NH—C(=O)—$NR^{100}$—, the ring structure that is comprised in $Q^{103}$ can be a ring structure that is formed with the R in the —$NR^{100}$— comprised in $A^{100}$; however, the number of divalent linking groups denoted by —NH—(C=O)—NH— is 0 or 1).

In one embodiment, in general formula (A-101), $Z^{101}$ comprises a alicyclic group or a aromatic ring group.

In one embodiment, in general formula (A-101), n103 denotes zero, $A^{100}$ denotes *—NH—C(=O)—$NR^{100}$—, and the ring structure comprised in $Q^{103}$ is a nitrogen-containing six-membered hetero ring formed with $R^{100}$ in —$NR^{100}$.

In one embodiment, the nitrogen-containing six-membered hetero ring is a morpholine ring.

In one embodiment, in general formula (A-100), one or more of the plurality of $Q^{103}$ are ring groups selected from the group consisting of aromatic groups and cycloalkyl groups.

In one embodiment, in general formula (A-100), one or more of the plurality of $Q^{103}$ denote unsubstituted phenyl groups or unsubstituted cyclohexyl groups.

In one embodiment, in general formula (A-100), one or more of the plurality of $Q^{103}$ denote alkyl groups.

In one embodiment, the compound denoted by general formula (A-100) is selected from the group consisting of the compound denoted by general formula (A-104-A) below, the compound denoted by general formula (A-104-B) below, and the compound denoted by general formula (A-105) below:

General formula (A-104-A)

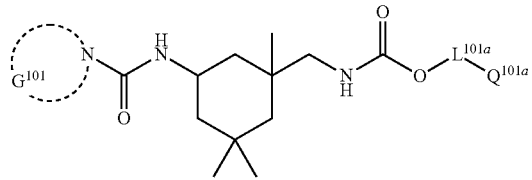

General formula (A-104-B)

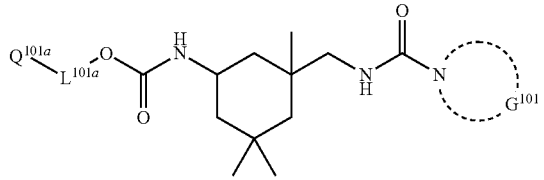

(wherein, in general formulas (A-104-A) and (A-104-B), $L^{101a}$ denotes a single bond, alkylene group, any one of groups denoted by general formulas (2A) to (2F) below, or a group comprising a combination of one or more groups denoted by general formulas (2A) to (2F) below and one or more alkylene group; $Q^{101a}$ denotes a substituent; and $G^{101}$ denotes an atom group forming a ring structure with a nitrogen atom to which the atom group connects; however, the number of divalent linking groups denoted by —NH—(C=O)—NH-per molecule is 0 or 1);

General formula (A-105)

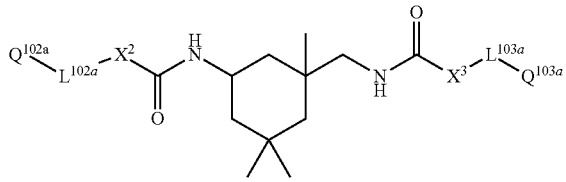

(wherein, in general formula (A-105), each of $L^{102a}$ and $L^{103a}$ independently denotes a single bond, alkylene group, any one of groups denoted by general formulas (2A) to (2F) below, or a group comprised of a combination of one or more groups denoted by general formulas (2A) to (2F) below and one or more alkylene group; each of $Q^{102a}$ and $Q^{103a}$ independently denotes a substituent; each of $X^2$ and $X^3$ independently denotes —$NR^{100}$— or —O—, with $R^{100}$ denoting a hydrogen atom or a substituent; and the number of divalent linking groups denoted by —NH—(C=O)—NH-per molecule is 0 or 1);

—{$R^b_{jb}(CR^aR^c)_{ja}$—O—(C=O)}—*;  General formula (2A)

—{$R^b_{jb}(CR^aR^c)_{ja}$—O}—*;  General formula (2B)

—{$R^b_{jb}(CR^aR^c)_{ja}$—(C=O)O—}—*;  General formula (2C)

—{$R^b_{jb}(CR^aR^c)_{ja}$—$NR^{100a}$(C=O)O—}—*;  General formula (2D)

—{$R^b_{jb}(CR^aR^c)_{ja}$—O—(C=O)$NR^{100a}$}*;  General formula (2E)

—{$R^b_{jb}(CR^aR^c)_{ja}$—$NR^{100a}$(C=O)$NR^{100a}$}—*;  General formula (2F)

(wherein, in general formulas (2A) to (2F), * denotes the position of the bond with $Q^{101a}$, $Q^{102a}$ or $Q^{103a}$, or the position of the bond with an adjacent group on the $Q^{101a}$, $Q^{102a}$, or $Q^{103a}$ side; each of $R^a$ and $R^c$ independently denotes a hydrogen atom or an alkyl group having 1 to 3 carbon atoms; ja denotes an integer greater than or equal to 1; when $R^a$ and $R^c$ are present in a plurality of number, the plurality of $R^a$ and $R^c$ can be identical or different; $R^b$ denotes a cyloalkylene group optionally substituted with one or more alkyl groups having 1 to 3 carbon atoms; jb denotes 0 or 1; $R^{100a}$ denotes a hydrogen atom or an alkyl group having 1 to 4 carbon atoms; when $R^{100a}$ are present in a plurality of number, the plurality of $R^{100a}$ can be identical or different; however, when both $X^2$ and $X^3$ denote —O—, one or both of $L^{102a}$ and $L^{103a}$ comprise divalent linking groups denoted by —$NR^{100a}$—C(=O)—NH—).

In one embodiment, the equivalent U (U=((molecular weight)/(total number of divalent linking groups denoted by —NH(C=O)—NR— and divalent linking groups denoted by —NH—C(=O)—O— contained per molecule)), calculated as the value obtained by dividing the molecular weight by the total number of divalent linking groups denoted by —NH(C=O)—NR— and divalent linking groups denoted by —NH—C(=O)—O— contained per molecule, is less than or equal to 515.

In one embodiment, the content of the compound denoted by general formula (I) and the compound denoted by general formula (A-100) in the cellulose acylate film set forth above (when two or more compounds are contained, "the content of the compound" means the total content of the compounds) is 0.1 to 50 mass parts per 100 mass parts of cellulose acylate.

A further aspect of the present invention relates to a polarizing plate having the above cellulose acylate film and a polarizer.

A still further aspect of the present invention relates to a liquid crystal display device having the above polarizing plate.

In one embodiment, the above polarizing plate is provided on at least the viewing side of a liquid crystal display device.

A still further aspect of the present invention relates to a compound denoted by general formula (II-1) below:

General formula (II-1)

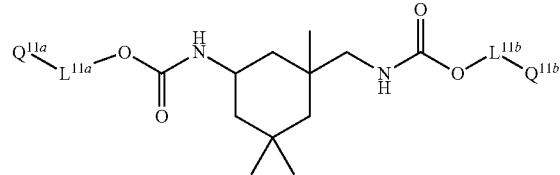

(wherein, in general formula (II-1), each of $L^{11a}$ and $L^{11b}$ independently denotes any one of the groups denoted by general formulas (2A-1) to (2E-1) below, a group comprising a combination of two or more groups denoted by general formulas (2A-1) to (2E-1) below, or a group comprising a combination of one or more groups denoted by general formulas (2A-1) to (2E-1) below and one or more alkylene groups; each of $Q^{11a}$ and $Q^{11b}$ independently denotes a substituent, and at least either $Q^{11a}$ or $Q^{11b}$ denoting a phenyl group optionally substituted with an alkoxy group having 1 to 3 carbon atoms or an alkyl group having 1 to 3 carbon atoms:

—{$(CR^aR^c)_{ja}$—O—(C=O)}—*;  General formula (2A-1)

—{$(CR^aR^c)_{ja}$—O}—*;  General formula (2B-1)

—{(CRᵃRᶜ)_{ja}—(C=O)O—}—*;  General formula (2C-1)

—{(CRᵃRᶜ)_{ja}—NR¹(C=O)O—}—*;  General formula (2D-1)

—{(CRᵃRᶜ)_{ja}—O—(C=O)NR¹}—*;  General formula (2E-1)

(wherein, in general formulas (2A-1) to (2E-1), * denotes the position of the bond with $Q^{11a}$ or $Q^{11b}$, or the position of the bond with an adjacent group on the $Q^{11a}$ or $Q^{11b}$ side; each of $R^a$ and $R^c$ independently denotes a hydrogen atom or an alkyl group having 1 to 3 carbon atoms; $R^1$ denotes a hydrogen atom or an alkyl group having 1 to 4 carbon atoms; ja denotes an integer greater than or equal to 1; when $R^a$, $R^c$, and $R^1$ are present in a plurality of number, the plurality of $R^a$, $R^c$, and $R^1$ can be identical or different).

A still further aspect of the present invention relates to a compound denoted by general formula (III-1) below:

General formula (III-1)

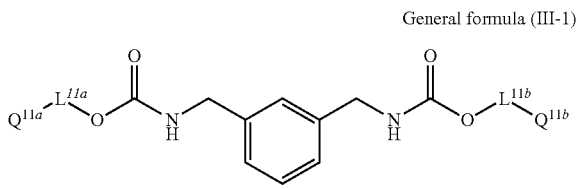

(wherein, in general formula (III-1), each of $L^{11a}$ and $L^{11b}$ independently denotes any one of the groups denoted by general formulas (2A-1) or (2C-1) to (2E-1) below, a group comprising a combination of two or more groups denoted by general formulas (2A-1) or (2C-1) to (2E-1) below, or a group comprising a combination of one or more groups denoted by general formulas (2A-1) or (2C-1) to (2E-1) below and one or more alkylene groups; each of $Q^{11a}$ and $Q^{11b}$ independently denotes a substituent, and at least either $Q^{11a}$ or $Q^{11b}$ denoting a phenyl group optionally substituted with an alkoxy group having 1 to 3 carbon atoms or an alkyl group having 1 to 3 carbon atoms:

—{(CRᵃRᶜ)_{ja}—O—(C=O)}—*;  General formula (2A-1)

—{(CRᵃRᶜ)_{ja}—(C=O)O—}—*;  General formula (2C-1)

—{(CRᵃRᶜ)_{ja}—NR¹(C=O)O—}—*;  General formula (2D-1)

—{(CRᵃRᶜ)_{ja}—O—(C=O)NR¹}—*;  General formula (2E-1)

(wherein, in general formulas (2A-1) and (2C-1) to (2E-1), * denotes the position of the bond with $Q^{11a}$ or $Q^{11b}$, or the position of the bond with an adjacent group on the $Q^{11a}$ or $Q^{11b}$ side; each of $R^a$ and $R^c$ independently denotes a hydrogen atom or an alkyl group having 1 to 3 carbon atoms; ja denotes an integer greater than or equal to 1; $R^1$ denotes a hydrogen atom or an alkyl group having 1 to 4 carbon atoms; when $R^a$, $R^c$, and $R^1$ are present in a plurality of number, the plurality of $R^a$, $R^c$, and $R^1$ can be identical or different).

A still further aspect of the present invention relates to a compound denoted by general formula (A-104-A) or (A-104-B) below:

General formula (A-104-A)

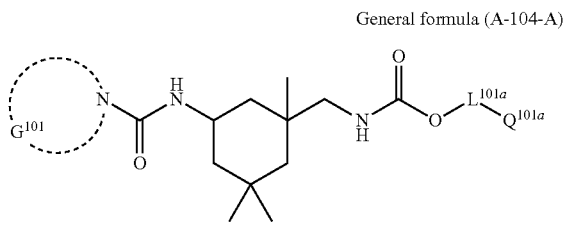

General formula (A-104-B)

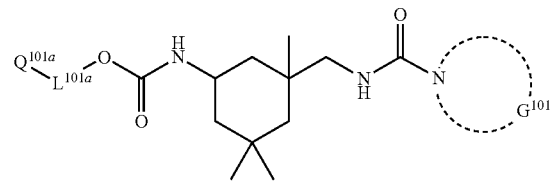

(wherein, in general formulas (A-104-A) and (A-104-B), $L^{1a}$ denotes a single bond, an alkylene group, or a group denoted by any of general formulas (2A-1) to (2C-1) below; $Q^{1a}$ denotes a substituent; and $G^1$ denotes an atom group forming a ring structure with a nitrogen atom to which the atom group connects:

—{(CRᵃRᶜ)_{ja}—O—(C=O)}—*;  General formula (2A-1)

—{(CRᵃRᶜ)_{ja}—O}—*;  General formula (2B-1)

—{(CRᵃRᶜ)_{ja}—(C=O)O—}—*;  General formula (2C-1)

(wherein, in general formulas (2A-1) to (2C-1), * denotes the position of the bond with the substituent denoted by $Q^{1a}$; each of $R^a$ and $R^c$ independently denotes a hydrogen atom or an alkyl group having 1 to 3 carbon atoms; ja denotes an integer greater than or equal to 1; when $R^a$ and $R^c$ are present in a plurality of number, the plurality of $R^a$ and $R^c$ can be identical or different).

A still further aspect of the present invention relates to a compound denoted by general formula (A-105) below.

General formula (A-105)

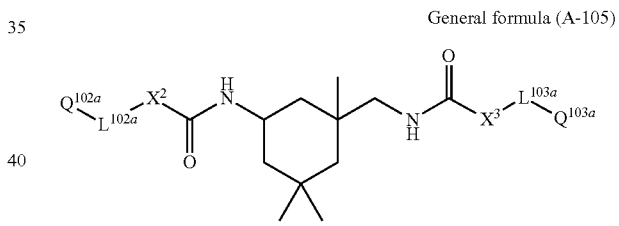

(wherein, in general formula (A-105), each of $L^{102a}$ and $L^{103a}$ independently denotes a group denoted by any of general formulas (2A-1) to (2F-1) below, a group comprising a combination of two or more groups denoted by general formulas (2A-1) to (2F-1) below; or a group comprising a combination of one or more groups denoted by general formulas (2A-1) to (2F-1) below and one or more alkylene groups; each of $Q^{102a}$ and $Q^{103a}$ independently denotes a substituent; each of $X^2$ and $X^3$ independently denotes —NR¹⁰⁰— or —O—, with $R^{100}$ denoting a hydrogen atom or a substituent; and the number of divalent linking groups denoted by —NH—(C=O)—NH-per molecule is 0 or 1);

—{(CRᵃRᶜ)_{ja}—O—(C=O)}—*;  General formula (2A-1)

—{(CRᵃRᶜ)_{ja}—O}—*;  General formula (2B-1)

—{(CRᵃRᶜ)_{ja}—(C=O)O—}—*;  General formula (2C-1)

—{(CRᵃRᶜ)_{ja}—NR¹⁰⁰ᵃ(C=O)O—}—*;  General formula (2D-1)

—{(CRᵃRᶜ)_{ja}—O—(C=O)NR¹⁰⁰ᵃ}—*;  General formula (2E-1)

—{(CRᵃRᶜ)_{ja}—NR¹⁰⁰ᵃ(C=O)NR¹⁰⁰ᵃ}—*;  General formula (2F-1)

(wherein, in general formulas (2A-1) to (2F-1), * denotes the position of the bond with $Q^{102a}$ or $Q^{103a}$, or the position of the bond with an adjacent group on the $Q^{102a}$ or $Q^{103a}$ side; each of $R^a$ and $R^c$ independently denotes a hydrogen atom or an alkyl group having 1 to 3 carbon atoms; ja denotes an integer greater than or equal to 1; when $R^a$ and $R^c$ are present in a plurality of number, the plurality of $R^a$ and $R^c$ can be identical or different; $R^{100a}$ denotes a hydrogen atom or an alkyl group having 1 to 4 carbon atoms; when $R^{100a}$ are present in a plurality of number, the plurality of $R^{100a}$ can be identical or different; however, when both $X^2$ and $X^3$ denote —O—, one or both of $L^{102a}$ and $L^{103a}$ comprise divalent linking groups denoted by —$NR^{100a}$—C(=O)—NH—).

According to an aspect of the present invention, a cellulose acylate film affording reduced light tinting, reduced volatilization of added compounds, and high surface hardness could be provided.

BRIEF DESCRIPTION OF THE DRAWINGS

FIG. 1 An example showing the positional relation between a polarizing plate and a liquid crystal display device, according to an embodiment of the present invention.

DETAILED DESCRIPTION OF THE EMBODIMENTS

The contents of the present invention will be described in detail below. In the present invention and Specification of the present application, a range stated using the word "to" includes the preceding and succeeding numeric values as minimum and maximum values, respectively. In the present invention and Specification of the present application, the word "group" as in an alkyl group and the like, unless specifically stated otherwise, can be substituted or unsubstituted.

When the number of carbon atoms in a group is specified, the number includes the number of carbon atoms present in any substituents.

The first aspect and the second aspect will be described in order. Unless specifically stated otherwise, the description of one aspect can be applied to the other aspect. Unless specifically stated otherwise, the groups that are given can have substituent(s). Examples of substituents are the various substituents described for substituent group T further below.

[Cellulose Acylate Film of the First Aspect]

The cellulose acylate film of the first aspect comprises the compound denoted by general formula (I) below, the equivalent U of which, calculated as U=((molecular weight)/(number of divalent linking groups denoted by —O—C(=O)—NH— contained per molecule)), is less than or equal to 515. The use of such a compound makes it possible to attain a cellulose acylate film with a hard surface and to reduce the adverse effects of light tinting. In addition, the above compound can exhibit low-volatility, thus contributing to providing a film that is highly transparent.

$Q^1$-$(L^{12}$-$L^{11})_{n1}$-O—C(=O)—NH-$(L^{21}$-$L^{22})_{n2}$-$Q^2$    General formula (I)

(In general formula (I), each of $L^{11}$ and $L^{21}$ independently denotes an optionally substituted alkylene group; each of $L^{12}$ and $L^{22}$ independently denotes a single bond, any one of or any combination of —O—, —$NR^1$—, —S—, and —C(=O)—. $R^1$ denotes a hydrogen atom or a substituent. Each of n1 and n2 independently denotes an integer of 0 to 20, with at least either n1 or n2 being an integer of greater than or equal to 1; when $L^{11}$, $L^{12}$, $L^{21}$, and $L^{22}$ are present in a plurality of number, the plurality of $L^{11}$, $L^{12}$, $L^{21}$, and $L^{22}$ can be identical or different. Each of $Q^1$ and $Q^2$ independently denotes a substituent, with at least either $Q^1$ or $Q^2$ comprising a ring structure.)

The alkylene groups denoted by $L^{11}$ and $L^{12}$ can be linear, branched, or cyclic, or can be in the form of an alkylene group in which one or more cyclic alkylene groups (cycloalkylene groups) and one or more linear or branched alkylene groups are connected. Specific examples of linear and branched alkylene groups are methylene groups, ethylene groups, propylene groups, butylene groups, pentylene groups, and hexylene groups. Alkylene groups having 1 to 20 carbon atoms are preferable, alkylene groups having 1 to 12 carbon atoms are more preferred, alkylene groups having 1 to 8 carbon atoms are yet more preference, alkylene groups having 1 to 3 carbon atoms are much more preference, and methylene groups, ethylene groups, or propylene groups are most preference as linear or branched alkylene groups. Optionally substituted cyclohexylene groups are preferable as cyclic alkylene groups. The alkylene groups can have substituent(s). Substituent group T set forth further below gives examples of substituents that can be present in the alkylene groups. Of these, substituents that are preferably present in the alkylene groups are alkyl groups, acyl groups, aryl groups, alkoxy groups, and carbonyl groups.

It is preferable for linear or branched alkylene groups to not have substituents. Cyclic alkylene groups preferably have substituent(s).

Each of $L^{12}$ and $L^{22}$ independently denotes a single bond, any one of or any combination of —O—, —$NR^1$—, —S—, and —C(=O)—. Of these, a single bond, oxygen atom, —$NR^1$—, or —C(=O)— is preferable. $R^1$ denotes a hydrogen atom or a substituent; examples of the substituent are an alkyl group, alkenyl group, aryl group, and acyl group. A hydrogen atom, an alkyl group having 1 to 8 carbon atoms, an alkenyl group having 2 to 8 carbon atoms, an alkynyl group having 2 to 8 carbon atoms, or an aryl group having 6 to 18 carbon atoms (such as a benzene ring or naphthalene ring group) is preferable, and a hydrogen atom or an alkyl group having 1 to 4 carbon atoms is more preferable.

In one embodiment, $L^{12}$ and $L^{22}$ preferably denote single bonds, —O—*, —OC(=O)—*, —C(=O)O—*, —$NR^1$—*, or —$R^1N$—*. Here, * denotes the position of the bond with $Q^1$ or $Q^2$, or the position at which an adjacent group is bonded on the $Q^1$ or $Q^2$ side.

Additionally, specific examples of the linking group denoted by -($L^{12}$-$L^{11}$)- or -($L^{21}$-$L^{22}$)- when $L^{12}$ and $L^{22}$ are —OC(=O)—* or —C(=O)O—* are given by the structures denoted by general formulas (2A) and (2C) below.

Specific examples of the linking group denoted by -($L^{12}$-$L^{11}$)- or -($L^{21}$-$L^{22}$)- when $L^{12}$ and $L^{22}$ are oxygen atoms are given by the structure denoted by general formula (2B) below.

Specific examples of the linking group denoted by -($L^{12}$-$L^{11}$)- or -($L^{21}$-$L^{22}$)- when $L^{12}$ and $L^{22}$ are —$NR^1$—OC(=O)—* or —$NR^1$—C(=O)O—* are given by the structure denoted by general formulas (2D) and (2E) below:

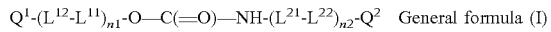    General formula (2A)

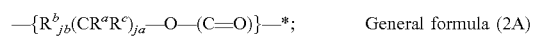    General formula (2B)

    General formula (2C)

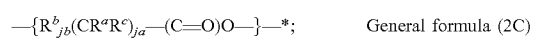    General formula (2D)

    General formula (2E)

(In general formulas (2A) to (2E), * denotes the position of the bond with $Q^1$ or $Q^2$, or the position of the bond with an adjacent group on the $Q^1$ or $Q^2$ side; each of $R^a$ and $R^c$ independently denotes a hydrogen atom or an alkyl group (for example, an alkyl group having 1 to 3 carbon atoms, preferably a methyl group); ja denotes an integer greater than or equal to 1, preferably an integer of 1 to 3. When $R^a$ and $R^c$ are present in a plurality of number, the plurality of $R^a$ and $R^c$ can be identical or different. $R^b$ denotes a cyloalkylene group optionally substituted with one or more alkyl groups having 1 to 3 carbon atoms, preferably a cyclohexylene group optionally substituted with 1 to 3 alkyl groups having 1 to 3 carbon atoms; jb denotes 0 or 1. $R^1$ denotes a hydrogen atom or a substituent, preferably a hydrogen atom or an alkyl group having 1 to 4 carbon atoms, with the alkyl group preferably being a methyl group. When $R^1$ are present in a plurality of number, the plurality of $R^1$ can be identical or different.)

When a plurality of the structure denoted by —($CR^aR^c$)— are contained in general formulas (2A) to (2E), it is preferable for both $R^a$ and $R^c$ to be hydrogen atoms or for at least either $R^a$ or $R^c$ to be an alkyl group.

Specific examples of linking groups denoted by general formula (2A) are:
—C(CH$_3$)$_2$—O—(C=O)—;
—CH$_2$CH$_2$—O—(C=O)—;
—CH$_2$CH$_2$CH$_2$—O—(C=O)—;
—CH$_2$CH(CH$_3$)—O—(C=O)—;
—CH(CH$_3$)CH$_2$—O—(C=O)—;
-(cyclohexylene group substituted with 1 to 3 alkyl groups having 1 to 3 carbon atoms)-CH$_2$—O—(C=O)—;
-(cyclohexylene group substituted with 1 to 3 alkyl groups having 1 to 3 carbon atoms)-CH$_2$CH$_2$—O—(C=O)—;
-(cyclohexylene group substituted with 1 to 3 alkyl groups having 1 to 3 carbon atoms)-CH$_2$CH$_2$CH$_2$—O—(C=O)—;
-(cyclohexylene group substituted with 1 to 3 alkyl groups having 1 to 3 carbon atoms)-CH$_2$CH(CH$_3$)—O—(C=O)—; and
-(cyclohexylene group substituted with 1 to 3 alkyl groups having 1 to 3 carbon atoms)-CH(CH$_3$)CH$_2$—O—(C=O)—.

Specific examples of linking groups denoted by general formula (2B) are: methyleneoxy groups; ethyleneoxy groups; propyleneoxy groups; butyleneoxy groups; pentyleneoxy groups; hexyleneoxy groups;
-(cyclohexylene group substituted with 1 to 3 alkyl groups having 1 to 3 carbon atoms)-CH$_2$—O—;
-(cyclohexylene group substituted with 1 to 3 alkyl groups having 1 to 3 carbon atoms)-CH$_2$CH$_2$—O—;
-(cyclohexylene group substituted with 1 to 3 alkyl groups having 1 to 3 carbon atoms)-CH$_2$CH$_2$CH$_2$—O—;
-(cyclohexylene group substituted with 1 to 3 alkyl groups having 1 to 3 carbon atoms)-CH$_2$CH(CH$_3$)—O—; and
-(cyclohexylene group substituted with 1 to 3 alkyl groups having 1 to 3 carbon atoms)-CH(CH$_3$)CH$_2$—O—.

Specific examples of linking groups denoted by general formula (2C) are:
—C(CH$_3$)$_2$—(C=O)—O—;
—CH$_2$CH$_2$—(C=O)—O—;
—CH$_2$CH$_2$CH$_2$—(C=O)—O—;
—CH$_2$CH(CH$_3$)—(C=O)—O—;
—CH(CH$_3$)CH$_2$—(C=O)—O—;
-(cyclohexylene group substituted with 1 to 3 alkyl groups having 1 to 3 carbon atoms)-CH$_2$—(C=O)—O—;
-(cyclohexylene group substituted with 1 to 3 alkyl groups having 1 to 3 carbon atoms)-CH$_2$CH$_2$—(C=O)—O—;
-(cyclohexylene group substituted with 1 to 3 alkyl groups having 1 to 3 carbon atoms)-CH$_2$CH$_2$CH$_2$—(C=O)—O—;
-(cyclohexylene group substituted with 1 to 3 alkyl groups having 1 to 3 carbon atoms)-CH$_2$CH(CH$_3$)—(C=O)—O—; and
-(cyclohexylene group substituted with 1 to 3 alkyl groups having 1 to 3 carbon atoms)-CH(CH$_3$)CH$_2$—(C=O)—O—.

Specific examples of linking groups denoted by general formula (2D) are:
-(cyclohexylene group substituted with 1 to 3 alkyl groups having 1 to 3 carbon atoms)-CH$_2$—NR$^1$(C=O)O—;
—CH$_2$—NR$^1$(C=O)—O—;
—CH$_2$CH$_2$—NR$^1$(C=O)—O—;
—CH$_2$CH$_2$CH$_2$—NR$^1$(C=O)—O—;
—CH$_2$CH(CH$_3$)—NR$^1$(C=O)—O—; and
—CH(CH$_3$)CH$_2$—NR$^1$(C=O)—O—.

Specific examples of linking groups denoted by general formula (2E) are:
-(cyclohexylene group substituted with 1 to 3 alkyl groups having 1 to 3 carbon atoms)-CH$_2$—O—(C=O) NR$^1$—;
—CH$_2$—NR$^1$(C=O)—O—;
—CH$_2$CH$_2$—NR$^1$(C=O)—O—;
—CH$_2$CH$_2$CH$_2$—NR$^1$(C=O)—O—;
—CH$_2$CH(CH$_3$)—NR$^1$(C=O)—O—; and
—CH(CH$_3$)CH$_2$—NR$^1$(C=O)—O—.

Examples of preferable forms of the linking groups denoted by ($L^{12}$-$L^{11}$) and ($L^{21}$-$L^{22}$) are alkylene groups and the groups denoted by general formulas (2A) to (2E). In one embodiment, examples of preferred forms are alkylene groups and the groups denoted by general formula (2A) or (2B). In another embodiment, examples of preferred forms are the groups denoted by general formula (2D) or (2E). The phrase "($L^{12}$-$L^{11}$) and ($L^{21}$-$L^{22}$) are alkylene groups" means that $L^{11}$ and $L^{21}$ denote alkylene groups and $L^{12}$ and $L^{22}$ denote single bonds. In general formula (I), when n1 and n2 denote integers that are greater than or equal to 1 (that is, integers falling within a range of 1 to 20), a plurality of ($L^{12}$-$L^{11}$) and ($L^{21}$-$L^{22}$) are contained in general formula (I). In that case, the plurality of ($L^{12}$-$L^{11}$) and the plurality of ($L^{21}$-$L^{22}$) can be of identical or different structures. The plurality of ($L^{12}$-$L^{11}$) and the plurality of ($L^{21}$-$L^{22}$) preferably contain a combination of an alkylene group and one or more of the groups denoted by any one of general formulas (2A) to (2E).

Substituent Group T:

Alkyl groups (preferably having 1 to 20, more preferably having 1 to 12, most preferably having 1 to 8 carbon atoms, such as methyl groups, ethyl groups, isopropyl groups, tert-butyl groups, n-octyl groups, n-decyl groups, n-hexadecyl groups, cyclopropyl groups, cylopentyl groups, and cyclohexyl groups); alkenyl groups (preferably having 2 to 20, more preferably having 2 to 12, and most preferably having 2 to 8 carbon atoms, such as vinyl groups, allyl groups, 2-butenyl groups, and 3-pentenyl groups); alkynyl groups (preferably having 2 to 20, more preferably having 2 to 12, and most preferably having 2 to 8 carbon atoms, such as propargyl groups and 3-pentynyl groups); aryl groups (preferably having 6 to 30, more preferably having 6 to 20, and most preferably having 6 to 12 carbon atoms, such as phenyl groups, biphenyl groups, and naphthyl groups); amino groups (preferably having 0 to 20, more preferably having 0 to 10, and most preferably having 0 to 6 carbon atoms, such as amino groups, methylamino groups, dimethylamino groups, diethylamino groups, and dibenzylamino groups); alkoxy groups (preferably having 1 to 20, more preferably having 1 to 12, and most preferably having 1 to 8 carbon atoms, such as methoxy groups, ethoxy groups, and butoxy groups); aryloxy groups (preferably having 6 to 20, more preferably having 6 to 16, and most preferably having 6 to 12 carbon atoms, such as phenyloxy groups and 2-naphthyloxy groups); acyl groups (preferably having 1 to 20, more preferably having 1 to 16, and most preferably having 1 to 12 carbon atoms, such as acetyl groups, benzoyl groups, formyl groups, and pivaloyl groups); alkoxycarbonyl groups (preferably having 2 to 20, more preferably having 2 to 16, and most preferably having 2 to 12 carbon atoms, such as methoxycarbonyl groups and ethoxycarbonyl groups); aryloxycarbonyl groups (preferably having 7 to 20, more preferably having 7 to 16, and most preferably having 7 to 10 carbon atoms, such as phenyloxycarbonyl groups); acyloxy groups (preferably having 2 to 20, more preferably having 2 to 16, and most preferably having 2 to 10 carbon atoms, such as acetoxy groups and benzoyloxy groups); acylamino groups (preferably having 2 to 20, more preferably having 2 to 16, and most preferably having 2 to 10 carbon atoms, such as acetylamino groups and benzoyl amino groups); alkoxycarbonylamino groups (preferably having 2 to 20, more preferably having 2 to 16, and most preferably having 2 to 12 carbon atoms, such as methoxycarbonylamino groups); aryloxycarbonylamino groups (preferably having 7 to 20, more preferably having 7 to 16, and most preferably having 7 to 12 carbon atoms, such as phenyloxycarbonylamino groups); sulfonylamino groups (preferably having 1 to 20, more preferably having 1 to 16, and most preferably having 1 to 12 carbon atoms, such as methanesulfonylamino groups and benzenesulfonylamino groups); sulfamoyl groups (preferably having 0 to 20, more preferably having 0 to 16, and most preferably having 0 to 12 carbon atoms, such as sulfamoyl groups, methylsulfamoyl groups, dimethylsulfamoyl groups, and phenylsulfamoyl); carbamoyl groups (preferably having 1 to 20, more preferably having 1 to 16, and most preferably having 1 to 12 carbon atoms, such as carbamoyl groups, methylcarbamoyl groups, diethylcarbamoyl groups, and phenylcarbamoyl groups); alkylthio groups (preferably having 1 to 20, more preferably having 1 to 16, and most preferably having 1 to 12 carbon atoms, such as methylthio groups and ethylthio groups); arylthio groups (preferably having 6 to 20, more preferably having 6 to 16, and most preferably having 6 to 12 carbon atoms, such as phenylthio groups); sulfonyl groups (preferably having 1 to 20, more preferably having 1 to 16, and most preferably having 1 to 12 carbon atoms, such as mesyl groups and tosyl groups); sulfinyl groups (preferably having 1 to 20, more preferably having 1 to 16, and most preferably having 1 to 12 carbon atoms, such as methanesulfinyl groups and benzenesulfinyl groups); urethane groups; ureido groups (preferably having 1 to 20, more preferably having 1 to 16, and most preferably having 1 to 12 carbon atoms, such as ureido groups, methylureido groups, and phenylureido groups); phosphamide groups (preferably having 1 to 20, more preferably having 1 to 16, and most preferably having 1 to 12 carbon atoms, such as diethylphosphamide groups and phenylphosphamide groups); hydroxyl groups; mercapto groups; halogen atoms (such as fluorine atoms, chlorine atoms, bromine atoms, and iodine atoms); cyano groups; sulfo groups; carboxyl groups; nitro groups; hydroxam groups; sulfino groups; hydrazino groups; imino groups, heterocyclic groups (preferably having 1 to 30 and more preferably having 1 to 12 carbon atoms with hetero atoms in the form of, for example, nitrogen atoms, oxygen atoms, and sulfur atoms, specific examples being imidazolyl groups, pyridyl groups, quinolyl groups, furyl groups, piperidyl groups, morpholino groups, benzoxazolyl groups, benzoimidazolyl groups, and benzothiazolyl groups); and silyl groups (preferably having 3 to 40, more preferably 3 to 30, and most preferably, 3 to 24 carbon atoms, such as trimethylsilyl groups and triphenylsilyl groups).

These substituents can be further substituted. When two or more substituents are present, the two or more substituents can be identical or different. When possible, they can connect to form rings.

Each of $Q^1$ and $Q^2$ independently denotes a substituent, with at least either $Q^1$ or $Q^2$ comprising a ring structure.

Substituent group T set forth above provides examples of substituents. Examples are aryl groups having 6 to 30 carbon atoms (preferably 6 to 20, more preferably 6 to 10); alkyl groups having 1 to 12 carbon atoms (preferably 1 to 10, more preferably 1 to 5) (it being permissible for oxygen atoms to be contained in the alkyl chain); alkenyl groups having 2 to 12 carbon atoms (preferably 2 to 10, and more preferably 2 to 5); and alkoxy groups having 1 to 12 carbon atoms (preferably 1 to 10, more preferably 1 to 5). $Q^1$ and $Q^2$ can comprise further substituents.

Specific examples of these substituents are provided by substituent group T set forth above. Aryl groups, alkyl groups, and acyl groups are preferable as the group T. The aryl group being referred to here is an aromatic hydrocarbon group.

Examples of the ring structure contained in one or both of $Q^1$ and $Q^2$ are aliphatic rings (such as cyclohexane rings) and aromatic rings (such as benzene rings and naphthalene rings).

Multiple types of rings can also be present, and the rings can be condensed rings. In one embodiment, the ring structure is preferably not a cyclic imide group. In still another embodiment, at least $Q^1$ or $Q^2$, preferably both, are preferably not polar groups. In the present invention, the term "polar group" refers to a substituent with a C log P value of less than or equal to 0.85. The C log P value will be described further below. In the present Specification, the C log P values of $Q^1$ and $Q^2$ are obtained as the C log P values of the compounds in the form of the given substituents connected to hydrogen: $Q^1$-H and $Q^2$-H. It is possible to calculate a C log P value even for a compound with a structure that does not actually exist by estimation using computational chemistry techniques or based on empirical methods. Specific examples of substituents with C log P values that are less than or equal to 0.85 are cyano groups and imide groups.

The ring structure that is contained in one or both of $Q^1$ and $Q^2$ is preferably an aliphatic carbon ring or an aromatic carbon ring, preferably a cyclohexane ring or a benzene ring, and more preferably, a benzene ring. From the perspective of increasing the surface hardness of the cellulose acylate film, in the compound denoted by general formula (I), 2 to 4 cyclohexane rings or benzene rings are preferably contained per molecule, with 2 or 3 being preferable. From the perspective of increasing the surface hardness of the cellulose acylate film, a ring structure that is contained as a terminal group of the molecule is preferably bonded to the main chain portion through a divalent linking group selected from the group consisting of —O—C(═O)—, —C(═O)—, and —O—. From the same perspective, a benzene ring is preferably contained in $Q^A$ or $Q^B$ as a terminal group of the molecule. When a substituent is present in the ring structure, a substituent in the form of an alkyl group having 1 to 3 carbon atoms or an alkoxy group having 1 to 3 carbon atoms is preferable.

It is also preferable for $Q^1$ to be a monovalent substituent denoted by general formula (a) below or a substituent in which one or more of these monovalent substituents are bonded to $L^2$ through a linking group:

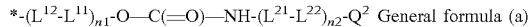
$$*\text{-}(L^{12}\text{-}L^{11})_{n1}\text{-}O\text{—}C(=O)\text{—}NH\text{-}(L^{21}\text{-}L^{22})_{n2}\text{-}Q^2 \quad \text{General formula (a)}$$

It is also preferable for $Q^2$ to be a monovalent substituent denoted by general formula (b) below or a substituent in which one or more of these monovalent substituents are bonded to $L^4$ through a linking group:

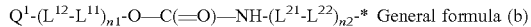
$$Q^1\text{-}(L^{12}\text{-}L^{11})_{n1}\text{-}O\text{—}C(=O)\text{—}NH\text{-}(L^{21}\text{-}L^{22})_{n2}\text{-}* \quad \text{General formula (b)}$$

That is, in the compound denoted by general formula (I), two or more of the structure denoted by $\text{-}(L^{12}\text{-}L^{11})_{n1}\text{-}O\text{—}C(=O)\text{—}NH\text{-}(L^{21}\text{-}L^{22})_{n2}\text{-}$ are preferably present per molecule. In general formulas (a) and (b) above, $L^{11}$ to $L^{22}$, n1, n2, $Q^1$, and $Q^2$ are defined as in general formula (I). Specific embodiments of compounds according to the above preferable embodiments will be described further below. Examples of the above linking groups are those described for $Z^1$ in general formula (I-1).

The compound denoted by general formula (I) comprises one or more divalent linking groups denoted by —NH—C(=O)—O—, and can comprise two or more. The number of divalent linking groups denoted by —NH—C(=O)—O— is preferably 1 to 6. In one embodiment, 2 or 3 are preferred. In yet another embodiment 2 to 4 are preferred.

In still another embodiment, the compound denoted by general formula (I) can contain a divalent linking group denoted by —NR$^1$—C(=O)—O— in addition to the divalent linking group denoted by —NH—C(=O)—O—. The total number of divalent linking groups denoted by —NH—C(=O)—O— and divalent linking groups denoted by —NR$^1$—C(=O)—O— is, for example, 2 to 6, preferably 2 to 4.

In one embodiment, the compound denoted by general formula (I) does not contain the divalent linking group denoted by —NR$^1$—C(=O)—NR$^1$— in portions other than the ring structure. Details regarding R$^1$ are as set forth above. The same applies to the compounds denoted by the various general formulas set forth in detail below.

The compound denoted by general formula (I) has an equivalent U calculated as U=((molecular weight)/(number of divalent linking groups denoted by —O—C(=O)—NH— contained per molecule)) of less than or equal to 515.

The lower the value of equivalent U, the higher the content of divalent linking groups denoted by —O—C(=O)—NH-per molecule. The compound denoted by general formula (I), the equivalent U of the compound is less than or equal to 515, can yield a cellulose acylate film with high surface hardness. Equivalent U is preferably less than or equal to 450, more preferably less than or equal to 420, and most preferably less than or equal to 300. There is no specific lower limit; by way of example, it can be greater than or equal to 100. In a preferable embodiment of the compound denoted by general formula (I), no groups denoted by —NH—C(=O)—NR— or —NR—C(=O)—NH— are contained per molecule. Here, R denotes a hydrogen atom or a substituent.

Examples of the substituent are the examples given in substituent group T. In one embodiment, the compound denoted by general formula (I) preferably does not contain the structure denoted by "-aromatic ring-NH—C(=O)—O—". Not containing such a structure can particularly inhibit light tinting of the cellulose acylate film. In yet another embodiment, it possible for the compound denoted by general formula (I) to contain the structure denoted by "-aromatic ring-NH—C(=O)—O—".

Each of n1 and n2 independently denotes an integer of 0 to 20, with either n1 or n2 denoting an integer of greater than or equal to 1. n1 and n2 preferably denote integers of 0 to 10, more preferably denote integers of 0 to 5, and most preferably denote integers of 0 to 3.

The compound denoted by general formula (I) is preferably the compound denoted by general formula (I-1):

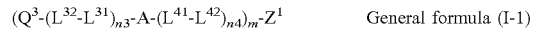
$$(Q^3\text{-}(L^{32}\text{-}L^{31})_{n3}\text{-}A\text{-}(L^{41}\text{-}L^{42})_{n4})_m\text{-}Z^1 \quad \text{General formula (I-1)}$$

(wherein, in general formula (I-1), each of $L^{31}$ and $L^{41}$ independently denotes an optionally substituted alkylene group; each of $L^{32}$ and $L^{42}$ independently denotes a single bond, any one of or any combination of —O—, —NR$^1$—, —S—, and —C(=O)—; R$^1$ denotes a hydrogen atom or a substituent; each of n3 and n4 independently denotes an integer of 0 to 20, with at least either n3 or n4 being an integer of greater than or equal to 1; when $L^{31}$, $L^{32}$, $L^{41}$, and $L^{42}$ in a plurality of number, the plurality of $L^{31}$, $L^{32}$, $L^{41}$, and $L^{42}$ can be identical or different; $Q^3$ denotes a substituent; $Z^1$ denotes a linking group of valence m; A denotes *—O—C(=O)—NH— or *—NH—C(=O)—O— (where * denotes the position of the bond with $L^{41}$); and m denotes an integer of 2 to 6; when $Q^3$ and A are present in a plurality of number, the plurality of $Q^3$ and A can be identical or different, with at least either $Q^3$ or $Z^1$ comprising a ring structure).

Each of $L^{31}$ and $L^{41}$ is independently defined identically with $L^{11}$ and $L^{21}$ in general formula (I). It is preferable for at least either $L^{31}$ or $L^{41}$ to be an alkylene group defined identically with that of $L^{11}$ and $L^{21}$ in general formula (I), and more preferable for both to be alkylene groups defined identically with those of $L^{11}$ and $L^{21}$ in general formula (I).

Each of $L^{32}$ and $L^{42}$ is independently defined identically with $L^{12}$ and $L^{22}$ in general formula (I), and their preferable ranges are identical.

Specifically, the linking group denoted by $(L^{41}\text{-}L^{42})$ is preferably a single bond or an alkylene group, and the linking group denoted by $(L^{32}\text{-}L^{31})$ is preferably a single bond, an alkylene group, or any of the groups denoted by general formulas (2A) to (2E) below. Details regarding general formulas (2A) to (2E) are as set forth above:

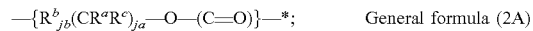
$$-\{R^b_{jb}(CR^aR^c)_{ja}\text{—}O\text{—}(C=O)\}\text{—}*; \quad \text{General formula (2A)}$$

$$-\{R^b_{jb}(CR^aR^c)_{ja}\text{—}O\}\text{—}*; \quad \text{General formula (2B)}$$

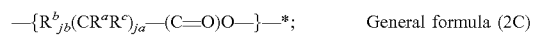
$$-\{R^b_{jb}(CR^aR^c)_{ja}\text{—}(C=O)O\text{—}\}\text{—}*; \quad \text{General formula (2C)}$$

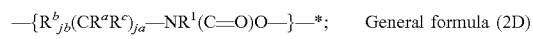
$$-\{R^b_{jb}(CR^aR^c)_{ja}\text{—}NR^1(C=O)O\text{—}\}\text{—}*; \quad \text{General formula (2D)}$$

$$-\{R^b_{jb}(CR^aR^c)_{ja}\text{—}O\text{—}(C=O)NR^1\}\text{—}*. \quad \text{General formula (2E)}$$

(In general formulas (2A) to (2E), * denotes the position of the bond with $Q^3$ or $Z^1$, or the position of the bond with an adjacent group on the $Q^3$ or $Z^1$ side. Details regarding $R^a$ and the like are as set forth above.)

n3 and n4 are defined identically with n1 and n2 in general formula (I) and their preferable ranges are identical.

m denotes an integer of 2 to 6, preferably an integer of 2 to 3.

$Q^3$ denotes a substituent, preferably a linear or branched alkyl group having 1 to 30 carbon atoms or a ring group having 6 to 30 carbon atoms, and more preferably consists only of a ring group. $Q^3$ can further comprise substituent(s). Specific examples of substituents are those given by substituent group T above. An aryl group, alkyl group, acyl group, or alkoxy group is preferable. However, it is preferable for no substituent to be present in $Q^3$.

The ring group contained in $Q^3$ can be a condensed ring but is preferably a monocyclic system. Specific examples are an aliphatic ring (cyclohexane ring or the like) and an aromatic ring (benzene ring, naphthalene ring, or the like). An aromatic ring is preferable, and an aromatic hydrocarbon ring is more preferable.

$Q^3$ is preferably an aryl group having 6 to 30 (preferably 6 to 20, and more preferably 6 to 10) carbon atoms or an aryl group having 5 to 30 (preferably 6 to 20, and more preferably 6 to 10) carbon atoms; and more preferably a benzene ring.

At least one of the plurality of $Q^3$ (the m instances of $Q^3$) preferably comprises a ring structure, with each instance preferably comprising a ring structure and more preferably comprising an aromatic group.

At least either $Q^3$ or $Z^1$ contains one or more ring structures, and both $Q^3$ and $Z^1$ preferably contain ring structures. It is preferable for one or both of $Q^3$ and $Z^1$ to contain ring structures, more preferable having 2 to 4 ring structures per molecule, and most preferable having 2 to 3 ring structures per molecule.

A denotes *—O—C(=O)—NH— or *—NH—C(=O)—O— (*denotes the position of the bond with $L^{41}$).

$Z^1$ denotes a linking group of valence m, preferably a linking group of valence 2 to 6, more preferably a linking group of valence 2 or 3, and most preferably, a linking group of valence 2. $Z^1$ is preferably a group containing at least one linear, branched, or alicyclic group or aromatic group; more preferably a group containing at least one branched or alicyclic group or aromatic group; yet more preferably a group containing at least one alicyclic or aromatic group; and most preferably, a group containing a alicyclic group.

$Z^1$ can be comprised of just one linear, branched, or alicyclic group or aromatic group, but is preferably a combination of this group and an oxygen atom and a linear or branched alkylene group. An aliphatic group that is contained as $Z^1$ is preferably a saturated aliphatic group.

Incorporating at least one selecting from a branched, alicyclic group or aromatic group, $Z^1$ can yield a rigid structure. Thus, incorporating this compound tends to further increase the surface hardness of the film. The number of carbon atoms constituting $Z^1$ is preferably 3 to 20, preferably 4 to 15.

$Z^1$ can comprise a substituent. Specific examples of substituents are those given by substituent group T above. However, the absence of substituents is preferable.

Specifically, the linking group given by way of example below is preferable. * denotes the position of the bond with $L^{41}$.

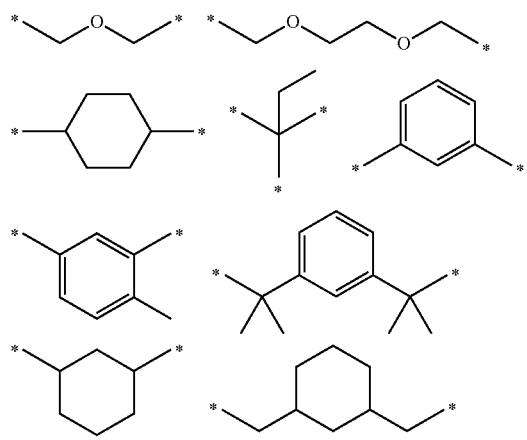

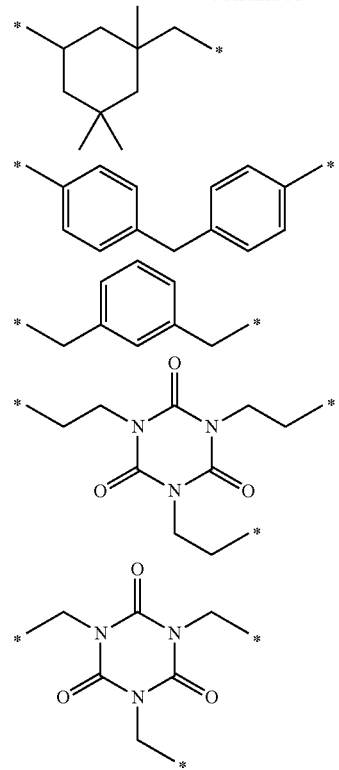

The compound denoted by general formula (I-1) preferably contains a ring structure in the form of an aliphatic carbon ring or an aromatic carbon ring. In the compound denoted by general formula (I-1), it is preferable for each instance of $Q^3$ to comprise an aromatic group (preferably a benzene ring) or for $Z^1$ to comprise a alicyclic group or aromatic group. It is preferable for each instance of $Q^3$ to be comprised of an unsubstituted aromatic group (preferably an unsubstituted benzene ring) or for $Z^1$ to comprise a alicyclic group. It is more preferable for each instance of $Q^3$ to be comprised of an unsubstituted aromatic ring group (preferably an unsubstituted benzene ring) or for $Z^1$ to be comprised of a cyclic aromatic group. And it is optimal for each instance of $Q^3$ to be comprised of an unsubstituted aromatic group (preferably an unsubstituted benzene ring) and for $Z^1$ to be comprised of a alicyclic group.

The compound denoted by general formula (I) is preferably the compound denoted by general formula (I-2) below:

$(Q^4-(L^{52}-L^{51})_{n5}-A-(L^{61}-L^{62})_{n6})_{m1}-Z^2$  General formula (I-2)

(wherein, in general formula (I-2), each of $L^{51}$ and $L^{61}$ independently denotes an optionally substituted alkylene group; each of $L^{52}$ and $L^{62}$ independently denotes a single bond, or any one of or any combination of —O—, —$NR^1$—, —S—, and —C(=O); $R^1$ denotes a hydrogen atom or a substituent; each of n5 and n6 independently denotes an integer of 0 to 20, with at least either n5 or n6 being an integer of greater than or equal to 1; when $L^{51}$, $L^{52}$, $L^{61}$, and $L^{62}$ are present in a plurality of number, the plurality of $L^{51}$, $L^{52}$, $L^{61}$, and $L^{62}$ can be identical or different; $Q^4$ denotes a substituted or unsubstituted phenyl group, substituted or unsubstituted cyclohexyl group, methyl group, ethyl group, propyl group, isopropyl group, or t-butyl group; $Z^2$ denotes a group comprising at least one linear, branched, or alicyclic group or aromatic group; A denotes *—O—C(=O)—NH— or *—NH—C(=O)—O— (where * denotes the position of the bond with $L^{61}$); and m1 denotes the integer 2 or 3; when $Q^4$ and A are present in a plurality of number, the plurality of $Q^4$ and A can be identical or different; with at least one from among $Z^2$ and the plurality of $Q^4$ comprising a ring structure).

Each of $L^{51}$ and $L^{61}$ is independently defined identically with $L^{11}$ and $L^{21}$ in general formula (I) and the preferable ranges are identical.

Each of $L^{61}$ and $L^{62}$ is independently defined identically with $L^{12}$ and $L^{22}$ in general formula (I) and the preferable ranges are identical.

Specifically, the linking group denoted by ($L^{61}$-$L^{62}$) is preferably a single bond or an alkylene group. The linking group denoted by ($L^{52}$-$L^{51}$) is preferably a single bond, alkylene group, or a group denoted by any of general formulas (2A) to (2E) below. Details regarding general formulas (2A) to (2E) are as set forth above:

| | |
|---|---|
| —{$R^b_{jb}(CR^aR^c)_{ja}$—O—(C=O)}—*; | General formula (2A) |
| —{$R^b_{jb}(CR^aR^c)_{ja}$—O}—*; | General formula (2B) |
| —{$R^b_{jb}(CR^aR^c)_{ja}$—(C=O)O—}—*; | General formula (2C) |
| —{$R^b_{jb}(CR^aR^c)_{ja}$—$NR^1$(C=O)O—}—*; | General formula (2D) |
| —{$R^b_{jb}(CR^aR^c)_{ja}$—O—(C=O)$NR^1$}—* | General formula (2E) |

(In general formulas (2A) to (2E), * denotes the position of the bond to $Q^4$ or $Z^2$, or the position of the bond with an adjacent group on the $Q^4$ or $Z^2$ side. Details regarding $R^a$ and the like are as set forth above.)

$Q^4$ denotes a substituted or unsubstituted phenyl group, substituted or unsubstituted cyclohexyl group, methyl group, ethyl group, propyl group, isopropyl group, or t-butyl group. In general formula (I-2), m1 denotes the integer 2 or 3. Thus, a plurality (m instances) of $Q^4$ are present in the compounded denoted by general formula (I-2). At least one of these plurality of $Q^4$ and $Z^2$ comprises a ring structure.

The phenyl group denoted by $Q^4$ can comprise a substituent or can be unsubstituted; an unsubstituted phenyl group is preferable.

The cyclohexyl group denoted by $Q^4$ can also comprise a substituent or be unsubstituted; an unsubstituted cyclohexyl group is preferable.

Specific examples of substituents that can be substituted on phenyl groups and cyclohexyl groups are given by substituent group T above.

The substitution position of substituent group T is not specifically limited. Substitution is possible at the ortho, meta, and para positions. Preferable substituents are halogen atoms, alkyl groups, and alkoxy groups; preferred substituents are alkyl groups having 1 to 3 carbon atoms and alkoxy groups having 1 to 3 carbon atoms.

Preferred examples of $Q^4$ are unsubstituted phenyl groups, unsubstituted cyclohexyl groups, and methyl groups.

$Z^2$ is a group comprising at least one branched or alicyclic group or aromatic group; preferably a group comprising at least one alicyclic group or aromatic group; and preferably a group comprising a alicyclic group. The ring structure contained in $Z^2$ is preferably an aliphatic carbon ring or an aromatic carbon ring.

$Z^2$ can be at just a branched or alicyclic group or aromatic group, but is preferably a combination of this group and an oxygen atom, a linear or branched alkylene group. The aliphatic group that is contained as $Z^2$ is preferably a saturated aliphatic group.

$Z^2$ preferably comprises 3 to 20, preferably 4 to 15 carbon atoms.

$Z^2$ can comprise substituent(s). Specific examples of substituents given by substituent group T set forth above. It is preferable for no substituent to be present.

A specific example of $Z^2$ is the group containing at least one linear or alicyclic group or aromatic group among the examples given for $Z^1$ above.

n5 and n6 are defined identically with n1 and n2 in general formula (I) and have the same preferable ranges.

m1 denotes the integer 2 or 3 and is preferably 2.

The compound denoted by general formula (I-3) below is a preferable form of the compound denoted by general formula (I).

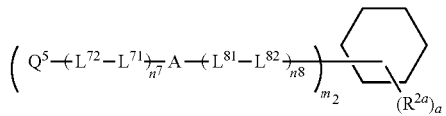

General formula (I-3)

(In general formula (I-3), each of $L^{71}$ and $L^{81}$ independently denotes an optionally substituted alkylene group. Each of $L^{72}$ and $L^{82}$ independently denotes a single bond, any one or any combination of —O—, —$NR^1$—, —S—, —C(=O)—. $R^1$ denotes a hydrogen atom or a substituent. Each of n7 and n8 independently denotes an integer of 0 to 20, with at least either n7 or n8 being an integer of greater than or equal to 1; a plurality of $L^{71}$, $L^{72}$, $L^{81}$, and $L^{82}$ can be identical or different. $Q^5$ denotes a substituted or unsubstituted phenyl group, substituted or unsubstituted cyclohexyl group, methyl group, ethyl group, propyl group, isopropyl group, or t-butyl group. A denotes *—O—C(=O)—NH— or *—NH—C(=O)—O— (where * denotes the position of the bond with $L^{81}$). $R^{2a}$ denotes an alkyl group having from 1 to 3 carbon atoms. m2 denotes the integer 2 or 3; the plurality of $Q^5$ and A that are present can be identical or different. a denotes an integer of 0 to 10; when a is an integer that is greater than or equal to 1, the plurality of $R^{2a}$ that are present can be identical or different.)

Each of $L^{71}$ and $L^{81}$ is independently defined identically with $L^{11}$ and $L^{21}$ in general formula (I) and has the same preferable range.

Each of $L^{72}$ and $L^{82}$ is independently defined identically with $L^{12}$ and $L^{22}$ in general formula (I) and has the same preferable range.

Each of n7 and n8 is independently defined identically with n1 and n2 in general formula (I) and as the same preferable range.

The linking group denoted by ($L^{72}$-$L^{71}$) is identical to the linking group denoted by ($L^{52}$-$L^{51}$) in general formula (I-2) and has the same preferable range.

The linking group denoted by ($L^{81}$-$L^{82}$) is identical to the linking group denoted by ($L^{62}$-$L^{61}$) in general formula (I-2) and has the same preferable range.

Among these, in one embodiment, the linking group denoted by ($L^{72}$-$L^{71}$) and the linking group denoted by ($L^{81}$-$L^{82}$) in general formula (I-3) are preferably the linking groups denoted by general formula (2A) and general formula (2B) above. In another embodiment, the linking groups denoted by general formula (2D) and general formula (2E) above are preferable.

$R^{2a}$ denotes an alkyl group having 1 to 3 carbon atoms, such as a methyl group, ethyl group, propyl group, or isopropyl group. $R^{2a}$ is preferably a methyl group.

m2 denotes the integer 2 or 3, preferably 2. a denotes an integer from 0 to 10, preferably an integer of 0 to 6 for effectively achieving the effect of the present invention.

$Q^5$ is defined identically with $Q^4$ in general formula (I-2) and has the same preferable range.

Specific examples of the bond positions of two or three side chains in the cyclohexane ring in general formula (I-3) are given below.

Below, * denotes a position at which the cyclohexane ring connects to the following structure:

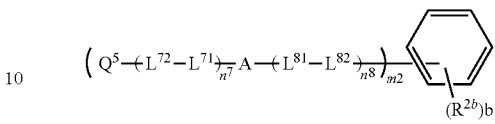

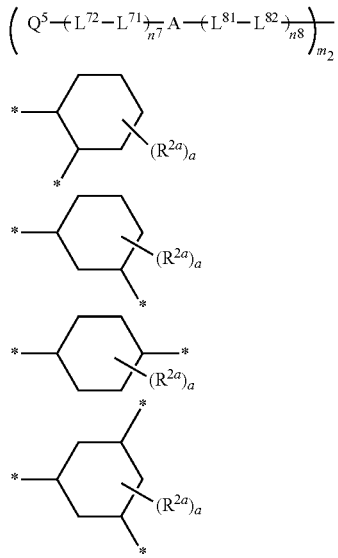

The above cyclohexane ring preferably has the structure indicated below.

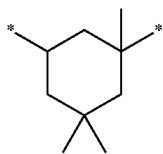

In general formula (I-3), when $Q^5$ denotes a substituted or unsubstituted phenyl group, the compound in general formula (I-3) is denoted by general formula (I-3-1) below.

General formula (I-3-1)

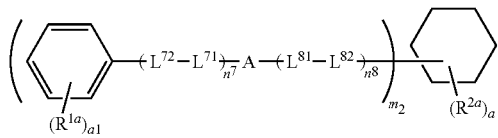

(In general formula (I-3-1), $R^{1a}$ denotes an alkyl group having 1 to 3 carbon atoms or an alkoxy group having 1 to 3 carbon atoms. a1 denotes an integer of 0 to 5. When a1 denotes an integer greater than or equal to 1, the plurality of $R^{1a}$ that are present can be identical or different. Each of $L^{71}$, $L^{72}$, $L^{81}$, $L^{82}$, n7, n8, m2, $R^{2a}$, and a is defined as in general formula (I-3) and has the same preferable range.)

$R^{1a}$ denotes an alkyl group having 1 to 3 carbon atoms or an alkoxy group having 1 to 3 carbon atoms, such as a methyl group, ethyl group, propyl group, isopropyl group, methoxy group, or ethoxy group. A methyl group or methoxy group is preferable.

a1 denotes an integer of 0 to 5, preferably 0 to 3, and more preferably, 0.

An example of a preferable form of the compound denoted by general formula (I) is the compound denoted by general formula (I-4) below:

General formula (I-4)

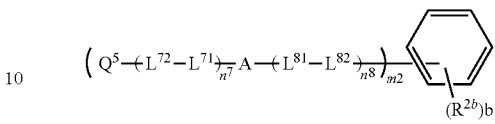

In general formula (I-4), each of $Q^5$, $L^{71}$, $L^{72}$, $L^{81}$, $L^{82}$, A, n7, n8, and m2 is defined as in general formula (I-3). $R^{2b}$ denotes an alkyl group having 1 to 3 carbon atoms. b denotes an integer of 0 to 5. When b denotes an integer that is greater than or equal to 1, the plurality of $R^{2b}$ can be identical or different.

In general equation (I-4), the linking group denoted by $(L^{72}\text{-}L^{71})_{n7}$ is defined identically with the linking group denoted by $(L^{52}\text{-}L^{51})_{n5}$ in general formula (I-2) and the preferable range is the same.

In general equation (I-4), the linking group denoted by $(L^{81}\text{-}L^{82})_{n8}$ is defined identically with the linking group denoted by $(L^{62}\text{-}L^{61})_{n6}$ in general formula (I-2) and the preferable range is the same.

In one embodiment, the linking group denoted by $(L^{72}\text{-}L^{71})$ and the linking group denoted by $(L^{81}\text{-}L^{82})$ are preferably the linking groups denoted by general formula (2A) or general formula (2B) above. In still another embodiment, the linking groups denoted by general formula (2D) and general formula (2E) above are preferable.

In general formula (I-4), the preferable ranges of $Q^5$, A, and m2 are each as defined in general formula (I-3).

$R^{2b}$ denotes an alkyl group having 1 to 3 carbon atoms, such as a methyl group, ethyl group, propyl group, or isopropyl group. $R^{2b}$ is preferably a methyl group.

b denotes an integer of 0 to 5, preferably an integer of 0 to 2, and from the perspective of inhibiting light tinting, is more preferably 0.

Specific examples of the positions of the bond of the two or three side chains in the benzene ring in general formula (I-4) are given below.

Below, * denotes a position at which the benzene ring connects to the following structure:

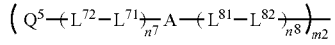

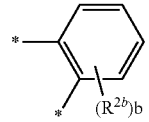

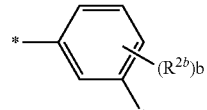

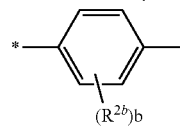

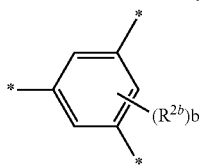

In general equation (I-4), when $Q^5$ denotes a substituted or unsubstituted phenyl group, the compound denoted by general equation (I-4) is denoted by general equation (I-4-1) below.

General equation (I-4-1)

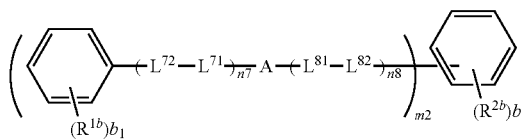

(In general equation (I-4-1), $R^{1b}$ denotes an alkyl group having 1 to 3 carbon atoms or an alkoxy group having 1 to 3 carbon atoms. b denotes an integer of 0 to 5. When b denotes an integer that is greater than or equal to 1, the plurality of $R^{1b}$ that are present can be identical or different. Each of $L^{71}$, $L^{72}$, $L^{81}$, $L^{82}$, n7, n8, m2, $R^{2b}$, and b is defined as in general equation (I-4) and has the same preferable range.)

$R^{1b}$ denotes an alkyl group having 1 to 3 carbon atoms or an alkoxy group having 1 to 3 carbon atoms, such as a methyl group, ethyl group, propyl group, isopropyl group, methoxy group, or ethoxy group; and preferably a methyl group or methoxy group.

b1 denotes an integer of 0 to 5, preferably 0 to 3, and more preferably, 0.

A preferable embodiment of the compound denoted by general formula (I) is the compound denoted by general formula (I-5) below.

In general formula (I-5), each of $Q^5$, $L^{71}$, $L^{72}$, $L^{81}$, $L^{82}$, A, n7, and n8 is defined as in general formula (I-3).

In general equation (I-5), the linking group denoted by $(L^{72}\text{-}L^{71})_{n7}$ is defined identically with the linking group denoted by $(L^{52}\text{-}L^{51})_{n5}$ in general formula (I-2) and the preferable range is the same.

In general equation (I-5), the linking group denoted by $(L^{81}\text{-}L^{82})_{n8}$ is defined identically with the linking group denoted by $(L^{62}\text{-}L^{61})_{n6}$ in general formula (I-2) and the preferable range is the same.

In general formula (I-5), the preferable range of A is identical to that in general formula (I-3).

In general formula (I-5), m3 denotes 1 or 2, preferably 1.

In general formula (I-5), each of $R^3$ and $R^4$ independently denotes a hydrogen atom or a methyl group; and both $R^3$ and $R^4$ are preferably hydrogen atoms or both $R^3$ and $R^4$ are more preferably methyl groups.

In general formula (I-5), a plurality of $Q^5$, $L^{71}$, $L^{72}$, $L^{81}$, $L^{82}$, A, n7, n8, and m3 can be identical or different.

General formula (I-5-1) is a preferable embodiment of the compound denoted by general formula (I-5).

General formula (I-5-1)

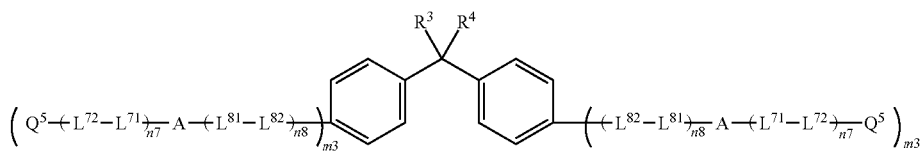

In general formula (I-5-1), each of $Q^5$, $L^{71}$, $L^{72}$, $L^{81}$, $L^{82}$, A, n7, n8, m3, $R^3$, and $R^4$ is defined as in general formula (I-5) and the preferable range is the same.

From the perspective of inhibiting light tinting in the compounds denoted by general formulas (I-3), (I-4), or (I-5), the compounds denoted by general formulas (I-3) or (I-4) are examples of preferable embodiments.

The compounds denoted by general formula (II) below and the compounds denoted by general formula (III) below are examples of preferable embodiments of the compound denoted by general formula (I). These compounds are useful as additives to cellulose acylate films.

General formula (II)

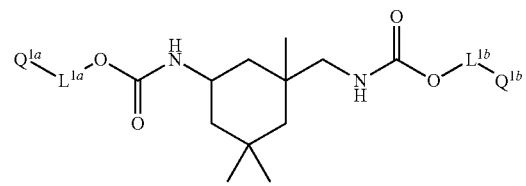

General formula (I-5)

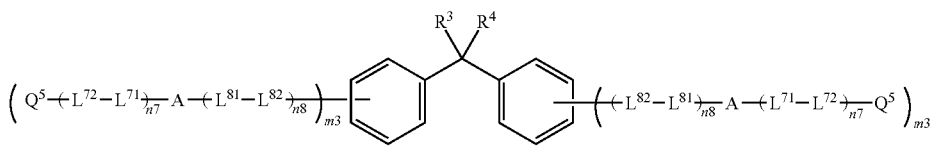

General formula (III)

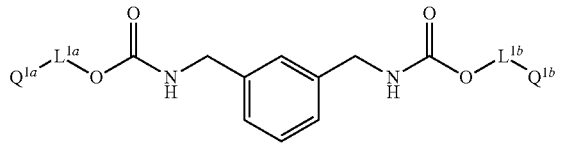

(In general formulas (II) and (III), each of $L^{1a}$ and $L^{1b}$ independently denotes a single bond, an alkylene group, one of the groups denoted by any of general formulas (2A) to (2E) set forth above, or a group comprising two or three combination of the groups denoted by general formulas (2A) to (2E) and alkylene groups; each of $Q^{1a}$ and $Q^{1b}$ independently denotes a substituent, where at least either $Q^{1a}$ or $Q^{1b}$ denotes a phenyl group optionally substituted with an alkoxy group having 1 to 3 carbon atoms or an alkyl group having 1 to 3 carbon atoms.)

In one embodiment, in general formulas (II) and (III), each of $L^{1a}$ and $L^{1b}$ independently denotes a single bond, an alkylene group, a group denoted by any one of general formulas (2A-1) to (2E-1) below, or a combination of any one of the groups denoted by general formulas (2A-1) to (2E-1) below and one or more alkylene groups, such as a group comprised of a combination of two or three:

—{$(CR^aR^c)_{ja}$—O—(C=O)}—*;   General formula (2A-1)

—{$(CR^aR^c)_{ja}$—O}—*;   General formula (2B-1)

—{$(CR^aR^c)_{ja}$—(C=O)O—}—*;   General formula (2C-1)

—{$(CR^aR^c)_{ja}$—NR$^1$(C=O)O—}—*;   General formula (2D-1)

—{$(CR^aR^c)_{ja}$—O—(C=O)NR$^1$}—*;   General formula (2E-1)

(wherein, in general formulas (2A-1) to (2E-1), * denotes the position of the bond with $Q^{1a}$ or $Q^{1b}$, or the position of the bond with an adjacent group on the $Q^{1a}$ or $Q^{1b}$ side; each of $R^a$ and $R^c$ independently denotes a hydrogen atom or an alkyl group having 1 to 3 carbon atoms; ja denotes an integer greater than or equal to 1; when $R^a$ and $R^c$ are present in a plurality of number, the plurality of $R^a$ and $R^c$ can be identical or different; and $R^1$ denotes a hydrogen atom or an alkyl group having 1 to 4 carbon atoms; when $R^1$ are present in a plurality of number, the plurality of $R^1$ can be identical or different).

Each of $L^{1a}$ and $L^{1b}$ denotes a single bond, an alkylene group, one of the groups denoted by any of general formulas (2A-1) to (2E-1) below, or a combination of two or more or any combination of the groups denoted by general formulas (2A-1) to (2E-1) below and alkylene groups, such as a group comprised of a combination of two or three. In general formulas (2A-1) to (2E-1), $R^a$, $R^c$, $R^1$, and ja are defined identically with $R^a$, $R^c$, $R^1$, and ja in general formulas (2A) to (2E).

Examples of the above alkylene groups are methylene and ethylene groups.

Each of $L^{1a}$ and $L^{1b}$ preferably denotes one of the groups denoted by any of general formulas (2A-1) to (2E-1), a group comprising two or more of the groups denoted by general formulas (2A-1) to (2E-1), or a group in the form of a combination of one or more of the groups denoted by general formulas (2A-1) to (2E-1) and one or more alkylene groups. This combination can be, for example, a combination comprised of two or three of the above groups.

Each of $Q^{1a}$ and $Q^{1b}$ independently denotes a substituent, examples of which are the substituents given by substituent group T above. At least either $Q^{1a}$ or $Q^{1b}$ denotes a phenyl group optionally substituted with an alkoxy group having 1 to 3 carbon atoms or an alkyl group having 1 to 3 carbon atoms. It is preferable for both $Q^{1a}$ and $Q^{1b}$ to denote phenyl groups optionally substituted with alkoxy groups having 1 to 3 carbon atoms or alkyl groups having 1 to 3 carbon atoms. It is preferable for both $Q^{1a}$ and $Q^{1b}$ to be unsubstituted phenyl groups.

Details regarding the alkyl group having 1 to 3 carbon atoms and the alkoxy group having 1 to 3 carbon atoms that are substituted onto the above phenyl group are as set forth for $R^{1a}$ in general formula (I-3-1).

For the group denoted by any of general formulas (2A-1) to (2C-1) contained in general formula (II), ja preferably denotes an integer that is greater than or equal to 2, more preferably denotes an integer that falls within a range of 2 to 5, and most preferably denotes 2 or 3. jc preferably denotes an integer of 1 to 3, and preferably denotes 1 or 2.

General formula (II-1) is an example of a preferable embodiment of the compound denoted by general formula (II).

General formula (II-1)

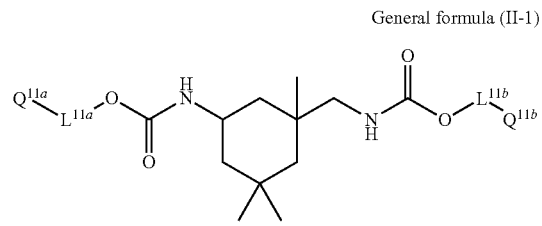

(In general formula (II-1), each of $L^{11a}$ and $L^{11b}$ independently denotes a single bond, an alkylene group, any one of the groups denoted by general formulas (2A-1) to (2E-1) below, a group comprising a combination of two or more groups denoted by general formulas (2A-1) to (2E-1) below, or a group comprising a combination of one or more groups denoted by general formulas (2A-1) to (2E-1) below and one or more alkylene groups; each of $Q^{11a}$ and $Q^{1b}$ independently denotes a substituent; at least $Q^{11a}$ or $Q^{1b}$ denotes a phenyl group optionally substituted with an alkoxy group having 1 to 3 carbon atoms or an alkyl group having 1 to 3 carbon atoms:

—{$(CR^aR^c)_{ja}$—O—(C=O)}—*;   General formula (2A-1)

—{$(CR^aR^c)_{ja}$—O}—*;   General formula (2B-1)

—{$(CR^aR^c)_{ja}$—(C=O)O—}—*;   General formula (2C-1)

—{$(CR^aR^c)_{ja}$—NR$^1$(C=O)O—}—*;   General formula (2D-1)

—{$(CR^aR^c)_{ja}$—O—(C=O)NR$^1$}—*;   General formula (2E-1)

(wherein, in general formulas (2A-1) to (2E-1), * denotes the position of the bond with $Q^{11a}$ or $Q^{11b}$, or the position of the bond with an adjacent group on the $Q^{11a}$ or $Q^{11b}$ side; each of $R^a$ and $R^c$ independently denotes a hydrogen atom or an alkyl group having 1 to 3 carbon atoms; $R^1$ denotes a hydrogen atom or an alkyl group having 1 to 4 carbon atoms; ja denotes an integer greater than or equal to 1; when $R^a$, $R^c$, and $R^1$ are present in a plurality of number, the plurality of $R^a$, $R^c$, and $R^1$ can be identical or different).

In general formula (II-1), details regarding $Q^{11a}$, $Q^{11b}$, $L^{11a}$, and $L^{11b}$ are identical with those for $Q^{1a}$, $Q^{1b}$, $L^{1a}$, and $L^{1b}$ in general formula (II), respectively.

In one embodiment, each of $L^{11a}$ and $L^{11b}$ independently denotes any one of the groups denoted by general formulas (2A-1) to (2E-1) below, a group comprising a combination of two or more groups denoted by general formulas (2A-1) to (2E-1) below, or a group comprising a combination of one or more groups denoted by general formulas (2A-1) to (2E-1) below and one or more alkylene groups. The above combination is, for example, comprised of a combination of two or three of the above groups.

An example of a preferable embodiment of the compound denoted by general formula (III) is general formula (III-1) below.

General formula (III-1)

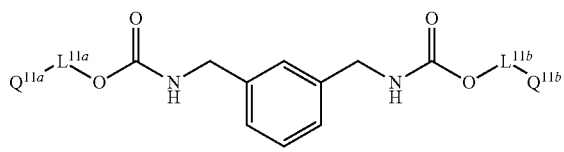

(In general formula (III-1), each of $L^{11a}$ and $L^{11b}$ independently denotes a single bond, an alkylene group, any one of the groups denoted by general formulas (2A-1) or (2C-1) to (2E-1) below, a group comprising a combination of two or more groups denoted by general formulas (2A-1) or (2C-1) to (2E-1) below, or a group comprising a combination of one or more groups denoted by general formulas (2A-1) or (2C-1) to (2E-1) below and one or more alkylene groups; each of $Q^{11a}$ and $Q^{11b}$ independently denotes a substituent; at least $Q^{11a}$ or $Q^{11b}$ denotes a phenyl group optionally substituted with an alkoxy group having 1 to 3 carbon atoms or an alkyl group having 1 to 3 carbon atoms:

| | |
|---|---|
| —{(CHR$^a$)$_{ja}$—O—(C=O)}—*; | General formula (2A-1) |
| —{(CHR$^a$)$_{ja}$—(C=O)O—}—*; | General formula (2C-1) |
| —{(CR$^a$R$^c$)$_{ja}$—NR$^1$(C=O)O—}—*; | General formula (2D-1) |
| —{(CR$^a$R$^c$)$_{ja}$—O—(C=O)NR$^1$}—*; | General formula (2E-1) |

(wherein, in general formulas (2A-1), (2C-1) to (2E-1), * denotes the position of the bond with $Q^{11a}$ or $Q^{11b}$, or the position of the bond with an adjacent group on the $Q^{11a}$ or $Q^{11b}$ side; each of $R^a$ and $R^c$ independently denotes a hydrogen atom or an alkyl group having 1 to 3 carbon atoms, ja denotes an integer greater than or equal to 1, and $R^1$ denotes a hydrogen atom or an alkyl group having 1 to 4 carbon atoms; when $R^a$, $R^c$, and $R^1$ are present in a plurality of number, the plurality of $R^a$, $R^c$, and $R^1$ can be identical or different).

In general formula (III-1), details for $Q^{11a}$, $Q^{11b}$, $L^{11a}$, and $L^{11b}$ are identical to those for $Q^{1a}$, $Q^{1b}$, $L^{1a}$, and $L^{1b}$ in general formula (III), respectively.

In one embodiment, each of $L^{11a}$ and $L^{11b}$ independently denotes any one of the groups denoted by general formulas (2A-1) to (2E-1) below, a group comprising a combination of two or more groups denoted by general formulas (2A-1) to (2E-1) below, or a group comprising a combination of one or more groups denoted by general formulas (2A-1) to (2E-1) below and one or more alkylene groups. The above combination is, for example, comprised of a combination of two or three of the above groups.

Examples of compounds denoted by general formula (I) that are preferably employed in the present invention are given below. However, the present invention is not limited thereto.

Here, the "k" in (1-1-k) is the same number as the k in the compound. For example, when k=2, the compound number is (1-1-2) and the k in —(CH$_2$)$_k$— in the compound is 2. The same applies to the compounds given below.

(1-1-k)

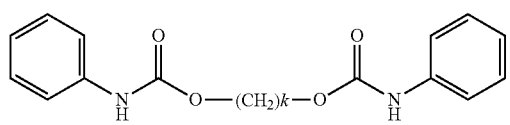

k = integer of 2-12

(1-2)

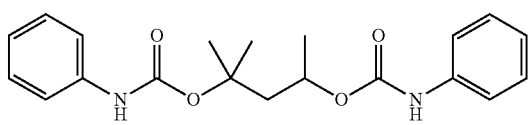

(1-3)

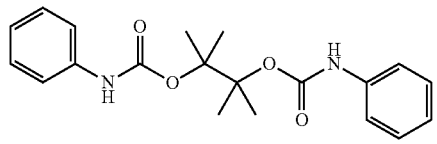

(1-4)

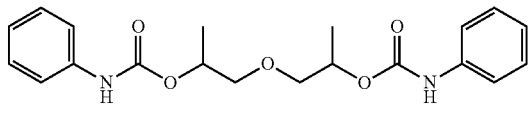

(1-5)

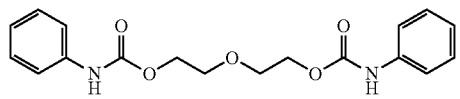

(1-6)

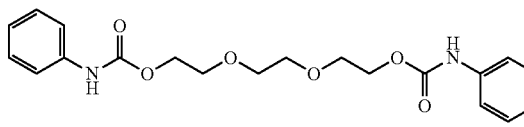

-continued
(1-7)
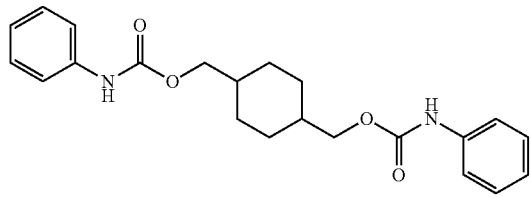
(1-8)
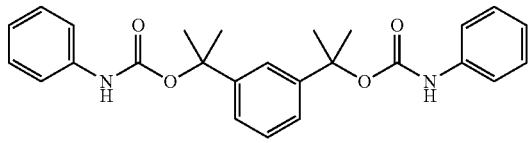
(1-11)
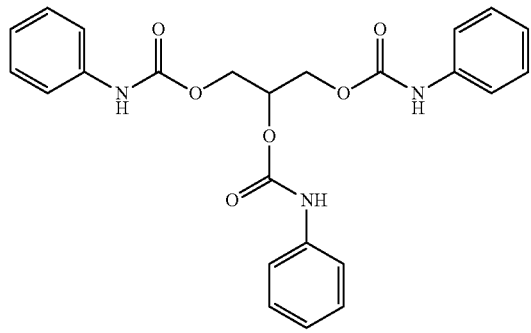
(1-12)
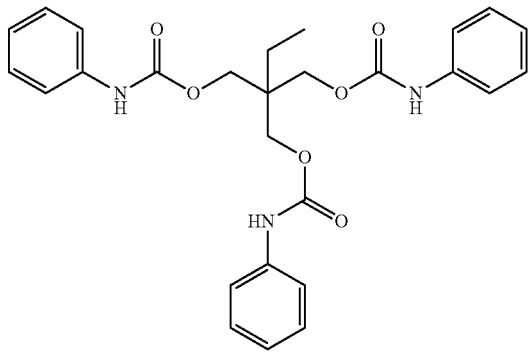
(1-13)
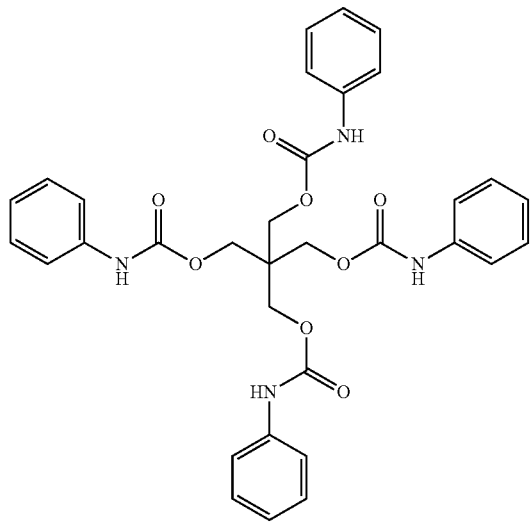
(1-14)
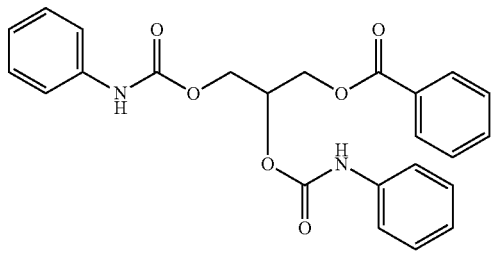
(1-15)
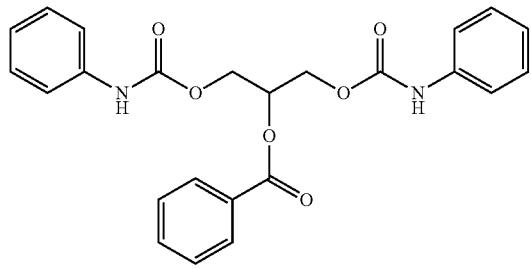
(1-16)
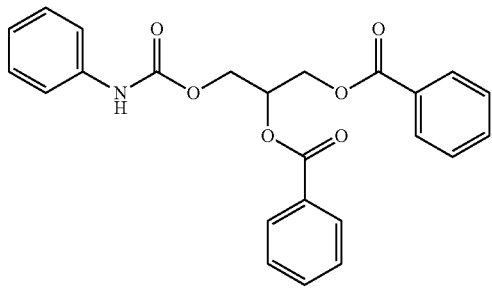

-continued
(1-17)
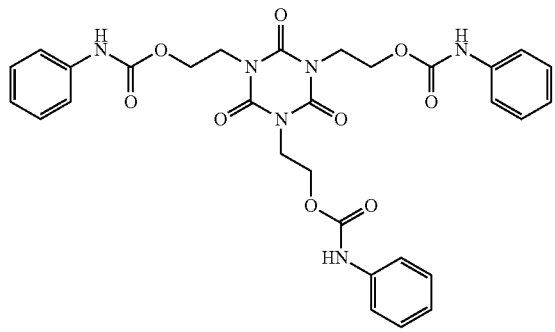
(1-21-k)
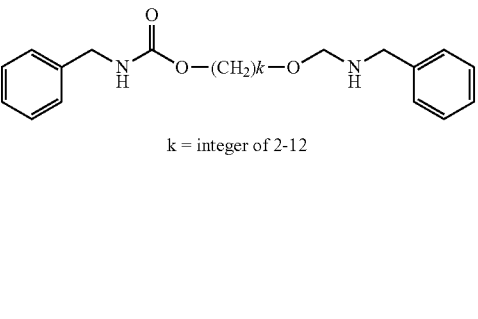
k = integer of 2-12
(1-22)
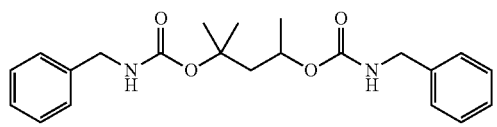
(1-23)
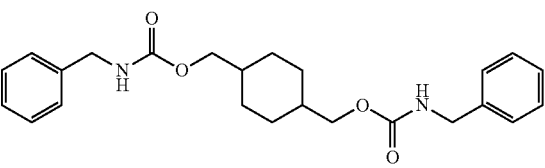
(1-24-k)
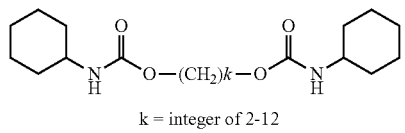
k = integer of 2-12
(2-1-1)
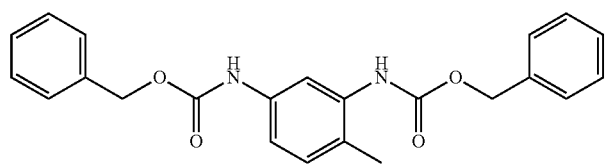
(2-1-2)
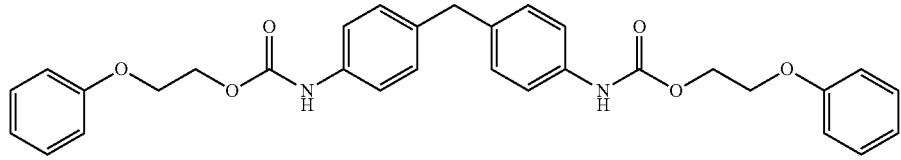
(2-2-1)
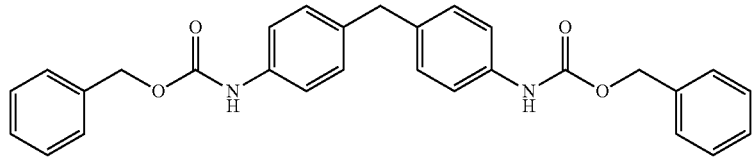
(2-2-2)
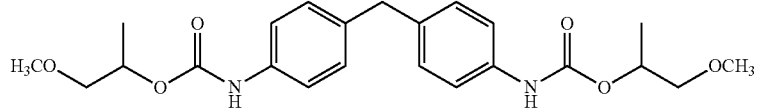
(2-2-3)
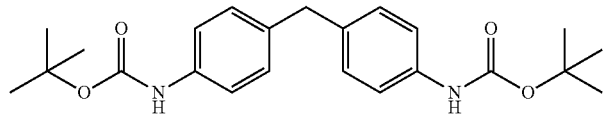
(2-2-4)

-continued
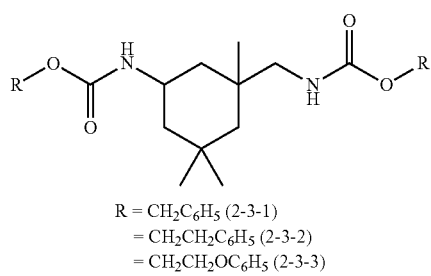
R = CH₂C₆H₅ (2-3-1)
  = CH₂CH₂C₆H₅ (2-3-2)
  = CH₂CH₂OC₆H₅ (2-3-3)
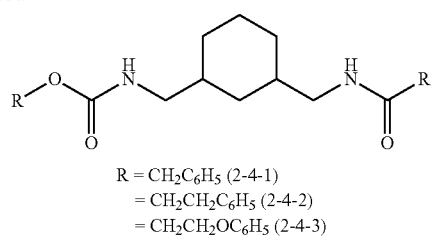
R = CH₂C₆H₅ (2-4-1)
  = CH₂CH₂C₆H₅ (2-4-2)
  = CH₂CH₂OC₆H₅ (2-4-3)
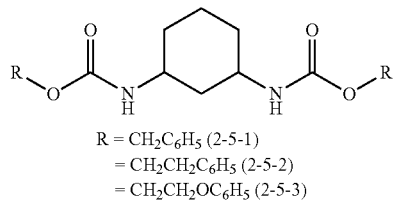
R = CH₂C₆H₅ (2-5-1)
  = CH₂CH₂C₆H₅ (2-5-2)
  = CH₂CH₂OC₆H₅ (2-5-3)
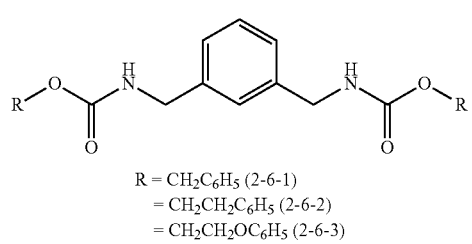
R = CH₂C₆H₅ (2-6-1)
  = CH₂CH₂C₆H₅ (2-6-2)
  = CH₂CH₂OC₆H₅ (2-6-3)
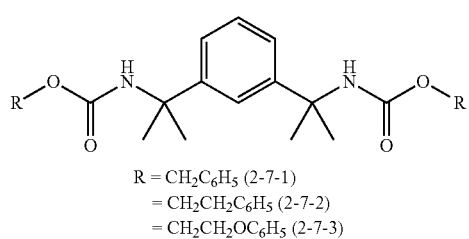
R = CH₂C₆H₅ (2-7-1)
  = CH₂CH₂C₆H₅ (2-7-2)
  = CH₂CH₂OC₆H₅ (2-7-3)
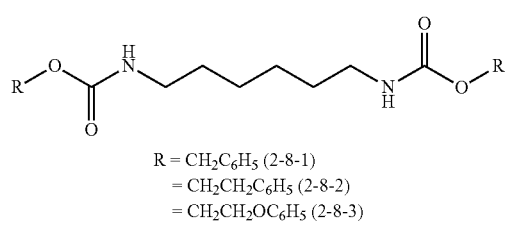
R = CH₂C₆H₅ (2-8-1)
  = CH₂CH₂C₆H₅ (2-8-2)
  = CH₂CH₂OC₆H₅ (2-8-3)
(2-9-1)
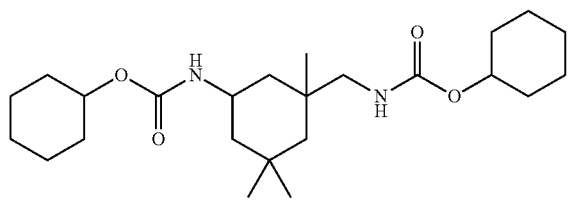
(2-9-2)
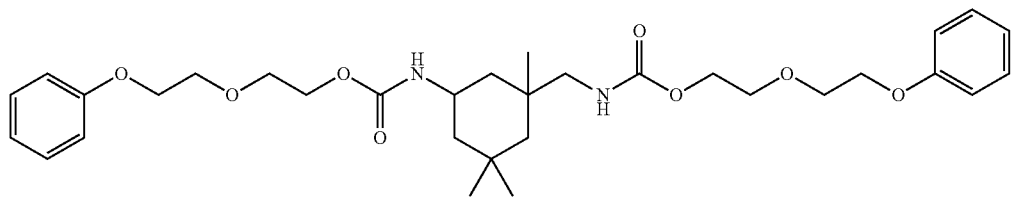
(2-9-3)
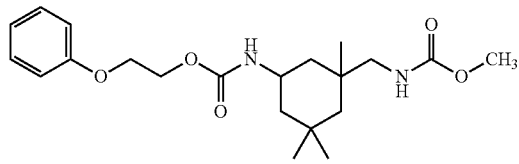
(2-9-4)
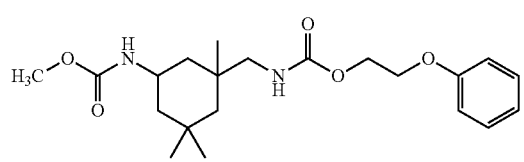
(2-10)
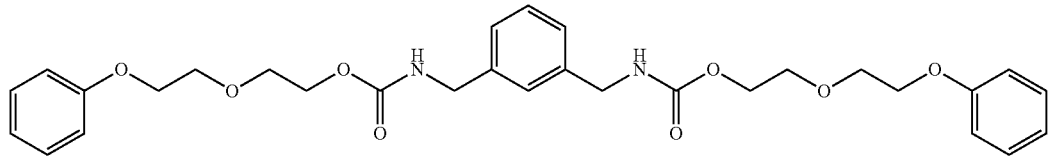

-continued
(2-11)
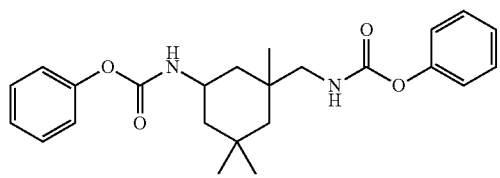
(2-12)
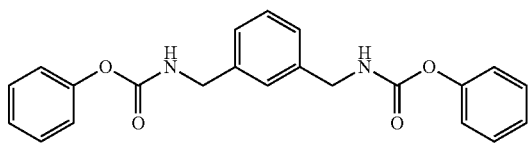
(2-13)
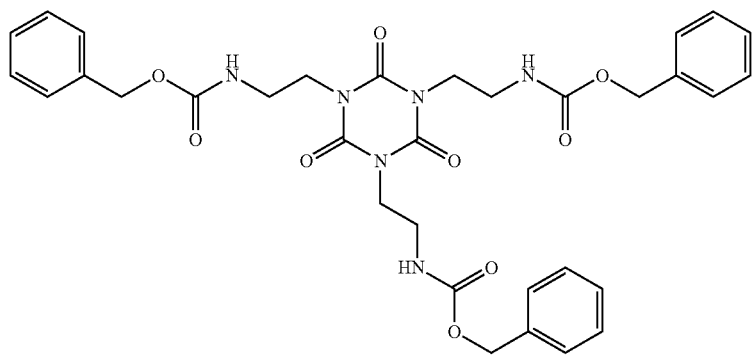
(2-15)
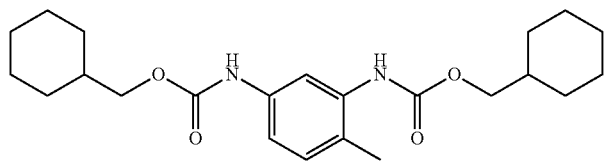
(2-16)
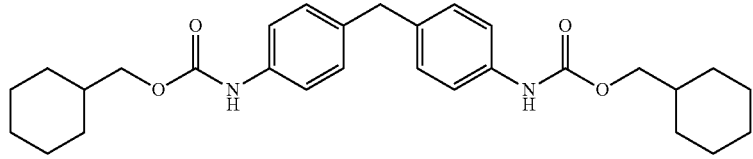
(3-1)
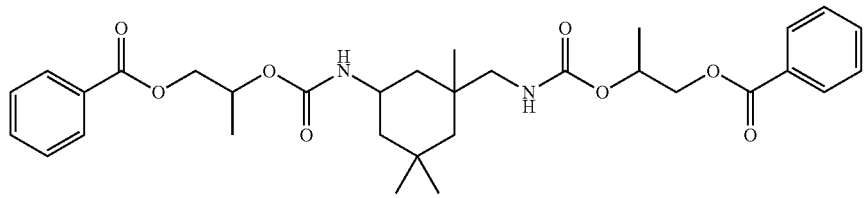
(3-2)
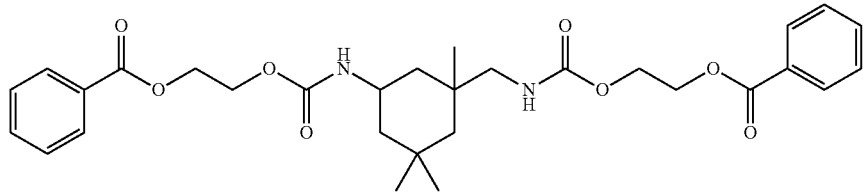
(3-3)
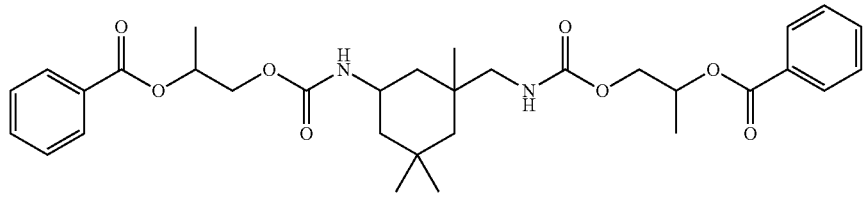

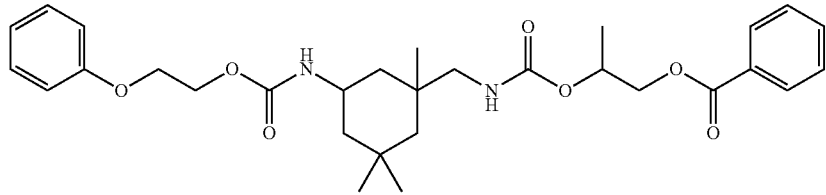
(3-4)
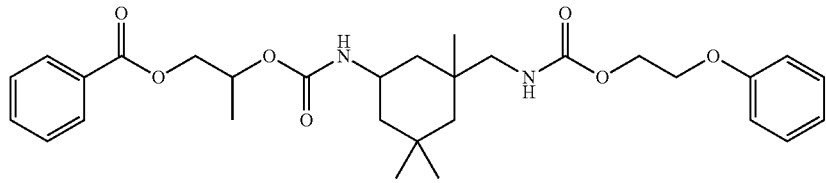
(3-5)
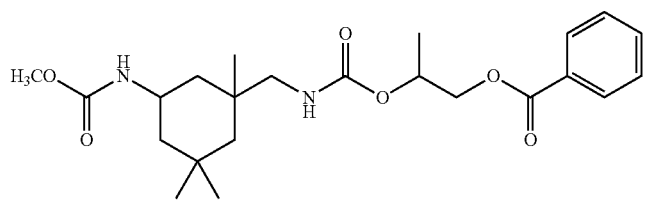
(3-6)
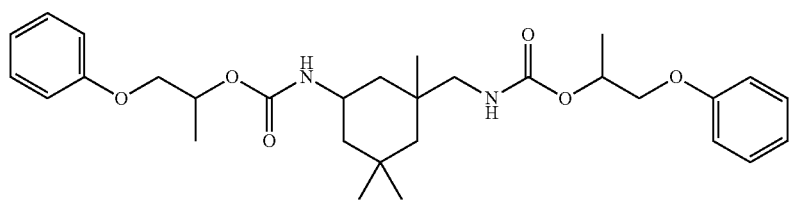
(3-7)
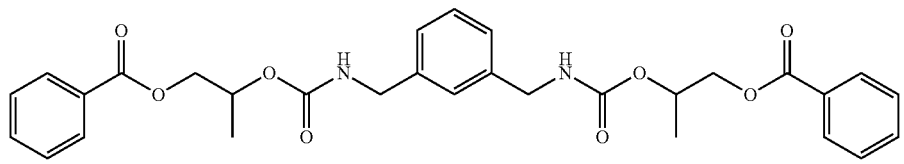
(3-8)
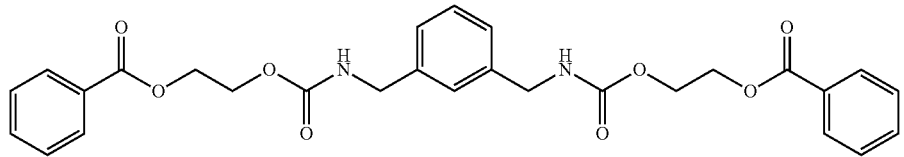
(3-9)
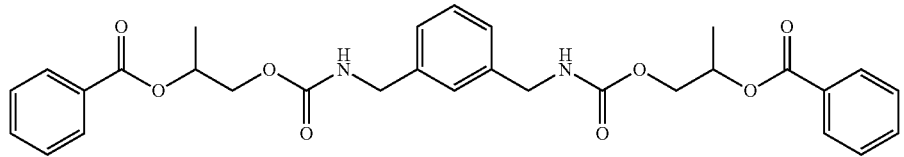
(3-10)
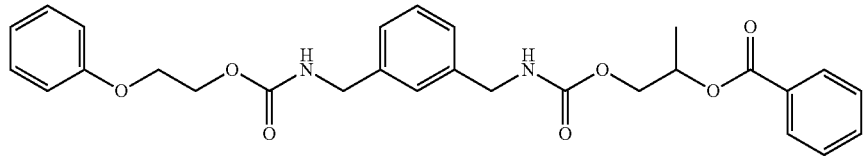
(3-11)

(3-12)
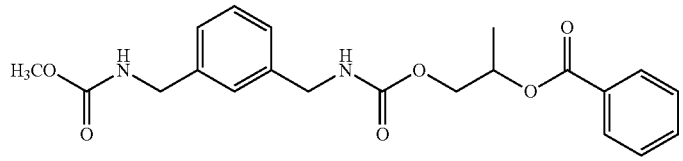
(3-13)
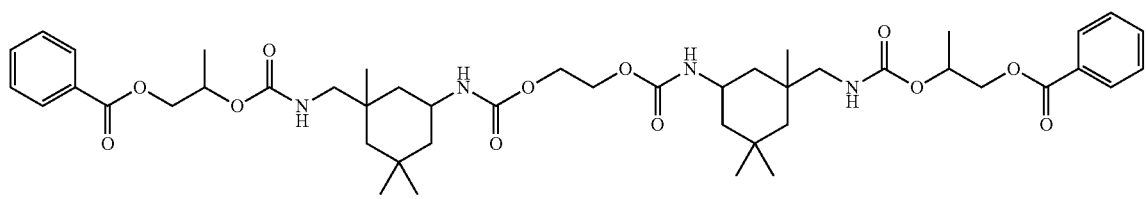
3-14 3-15
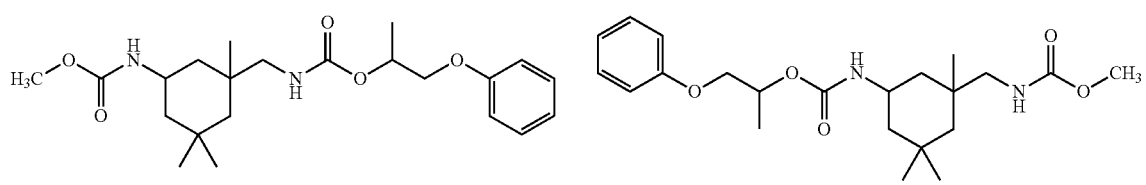
3-16 3-17
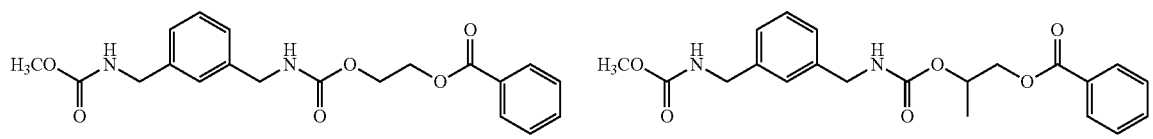
3-18
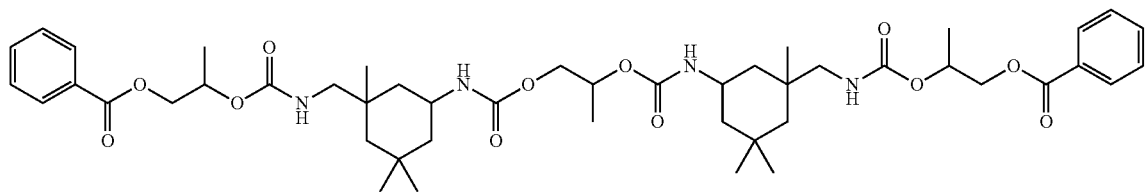
3-19
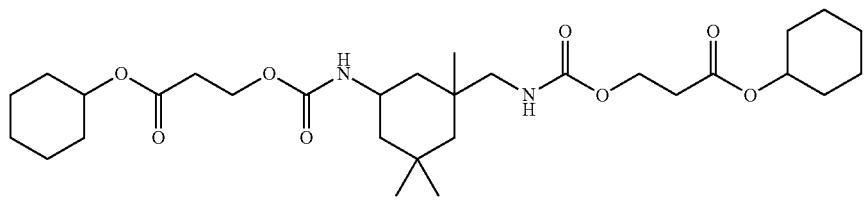
3-20
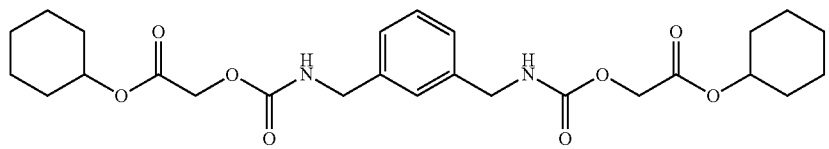
4-1
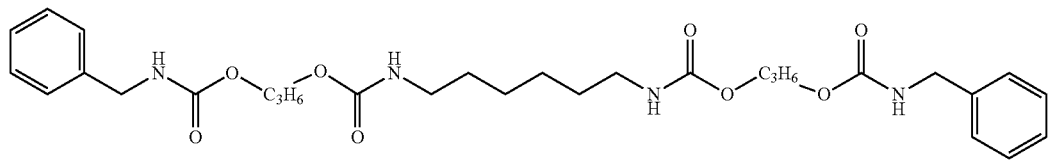

4-2
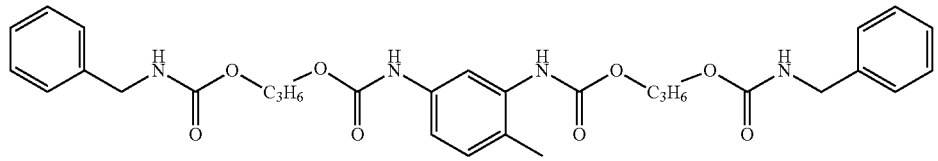
4-3
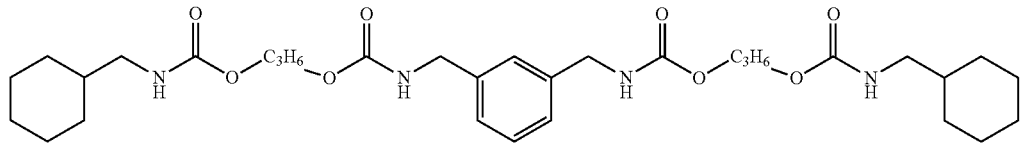
4-4
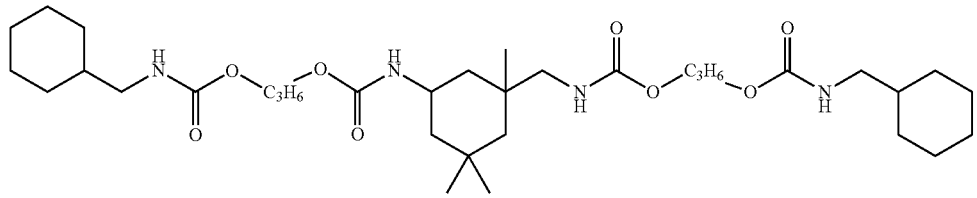
4-5
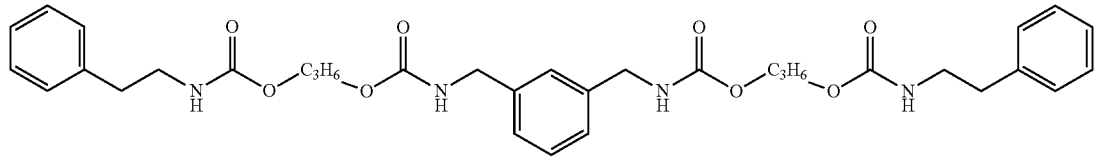
4-6
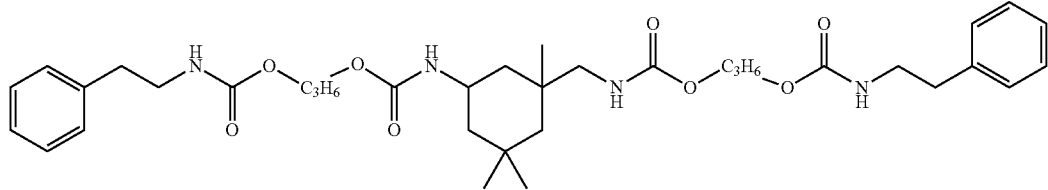
4-7
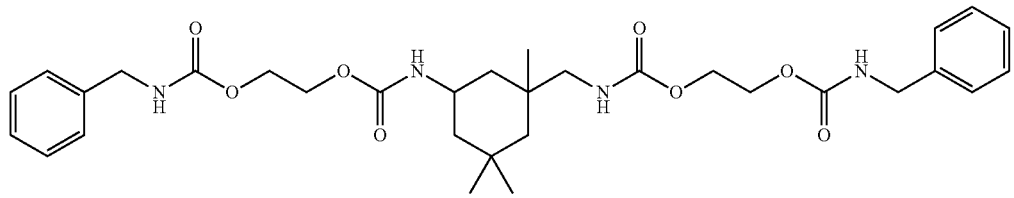
4-8
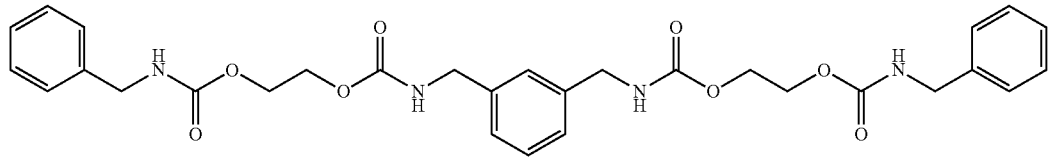
4-9
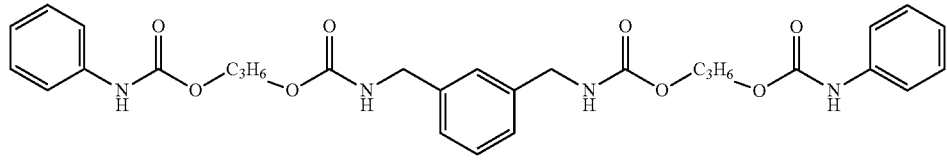

4-10
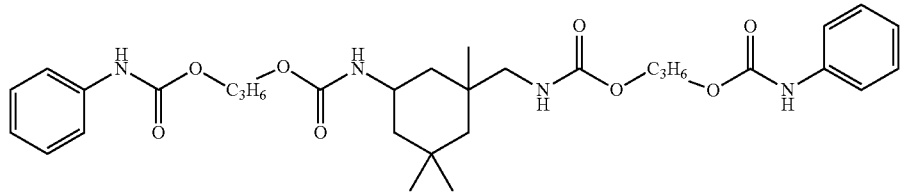
4-11
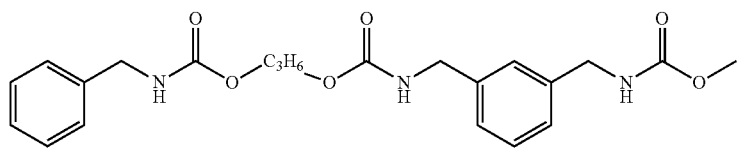
4-12 (mixture)
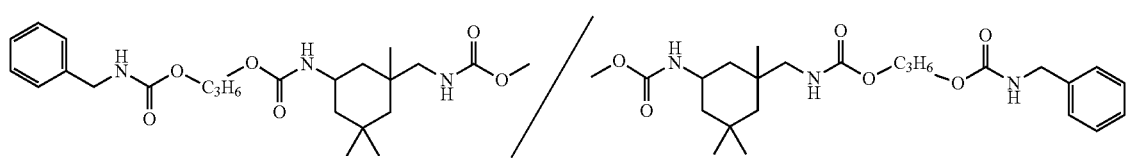
4-13
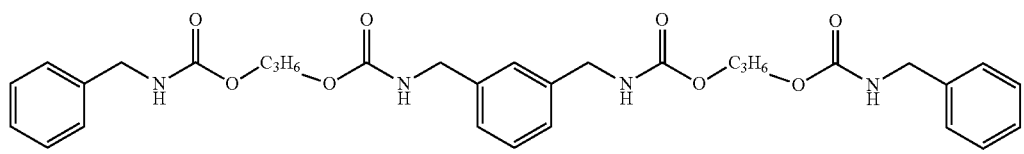
4-14
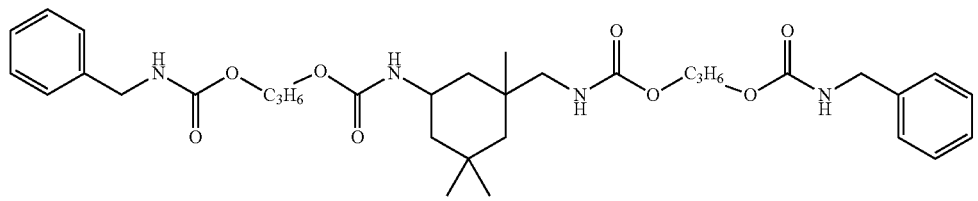
4-15
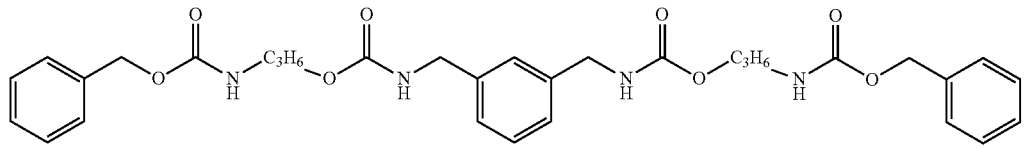
4-16
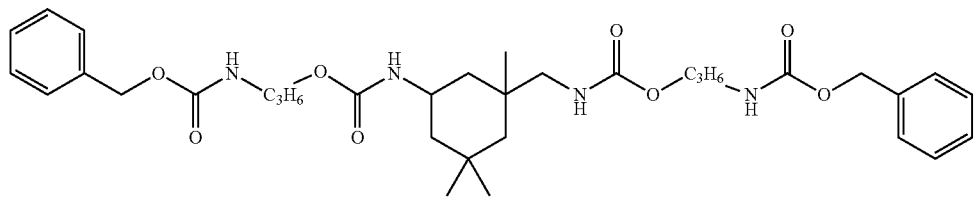
4-17
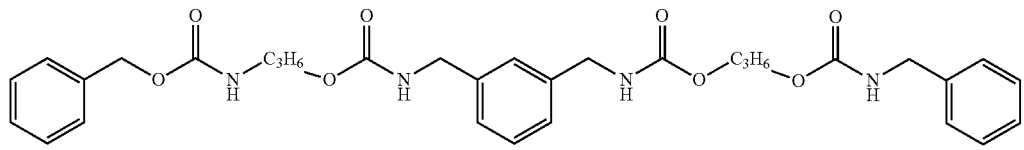

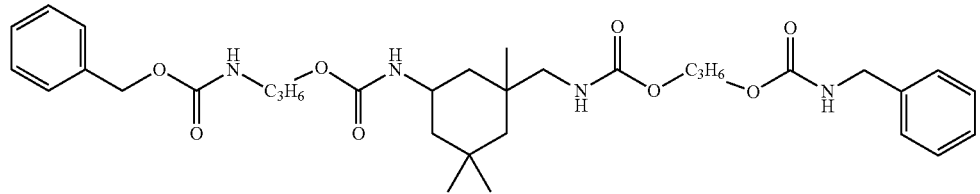
4-18 (mixture)
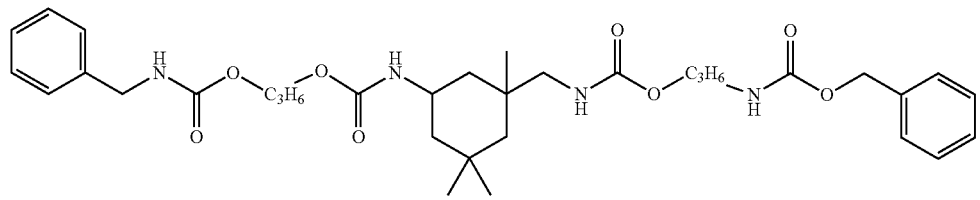
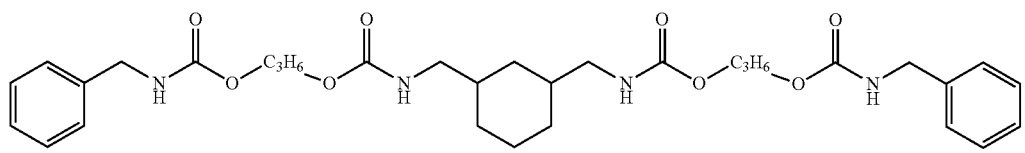
4-19
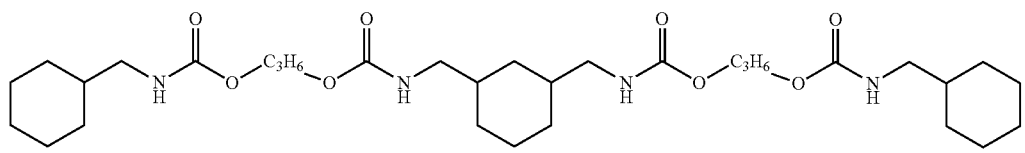
4-20
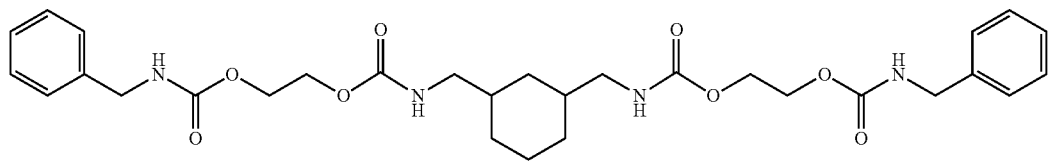
4-21
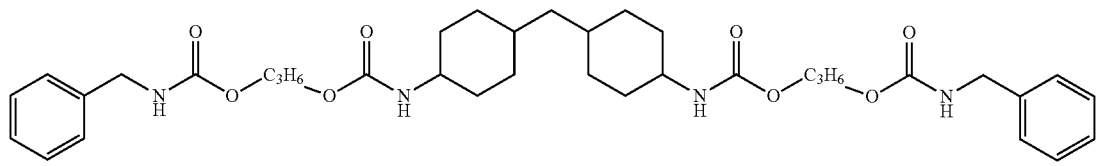
4-22
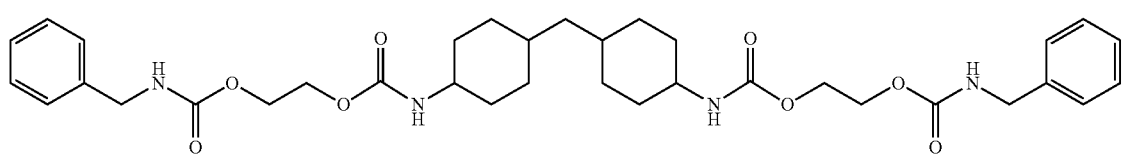
4-23
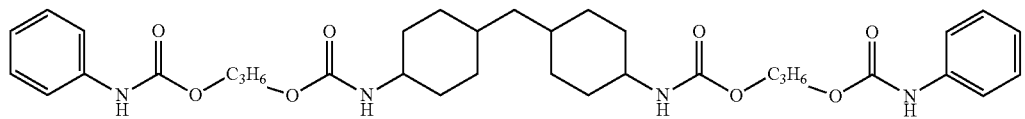
4-24
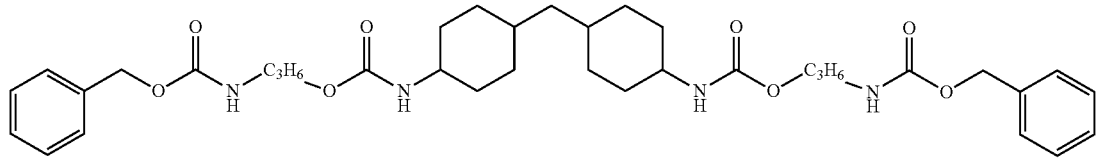
4-25

4-26
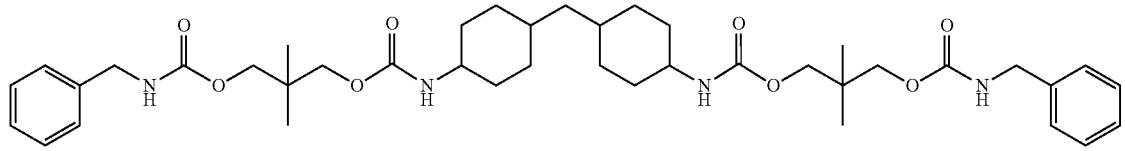
4-27
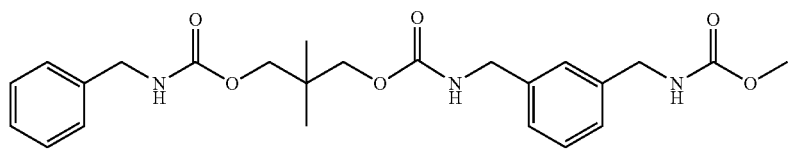
4-28
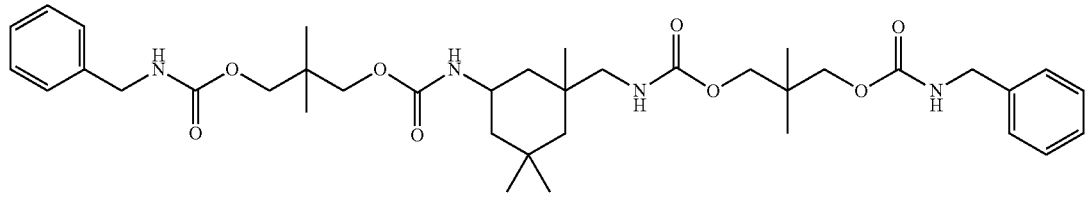
4-29
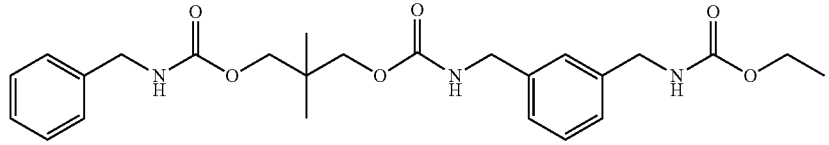
4-30
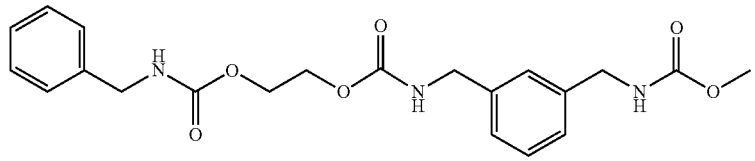
4-31
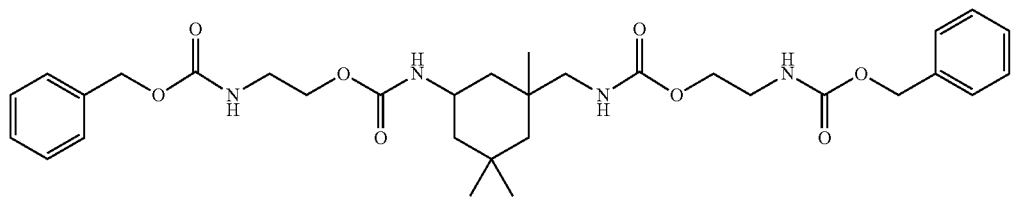
4-32
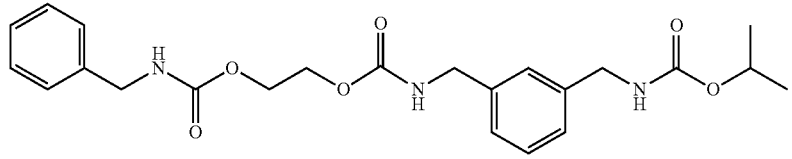
4-33
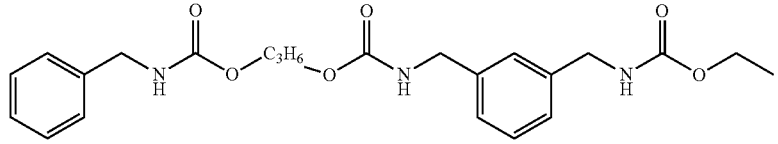
4-34
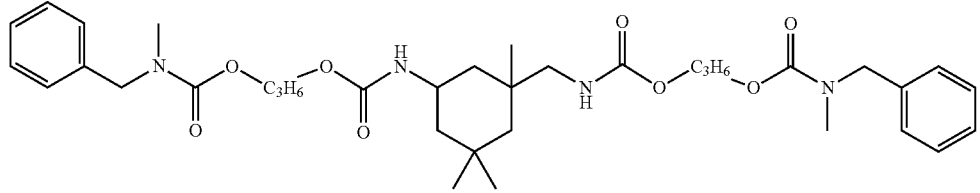

4-35
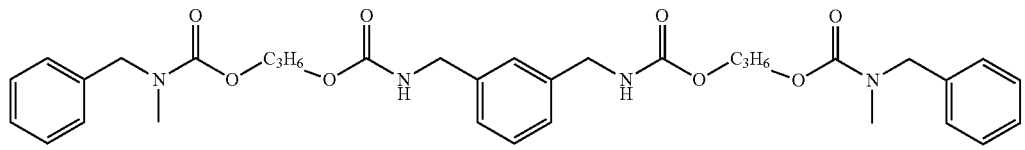
4-36 (mixture)
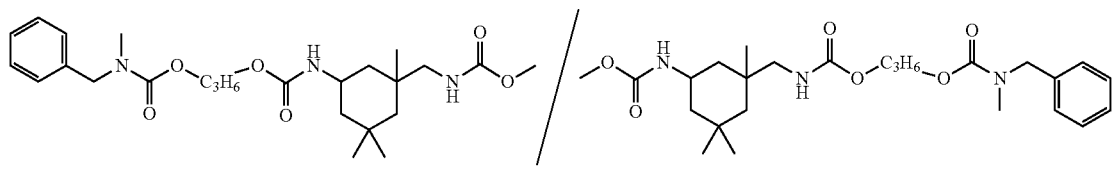
4-37 (mixture)
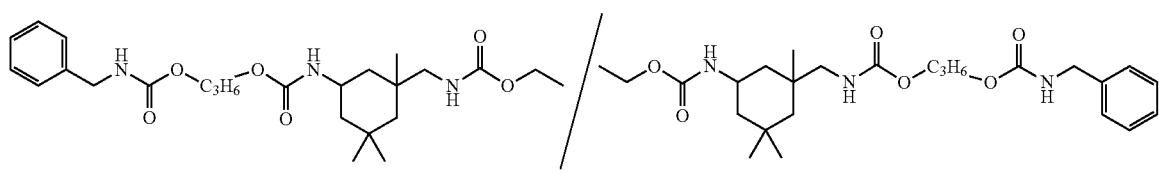
4-38 (mixture)
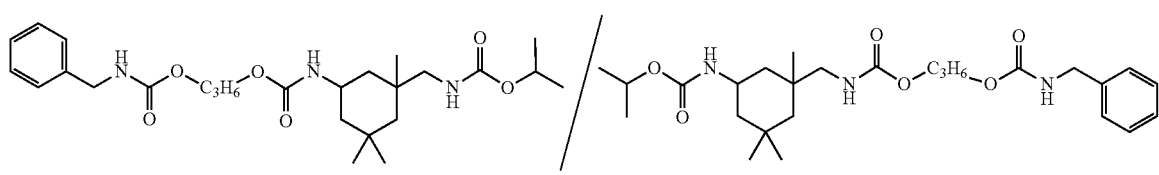
4-39 (mixture)
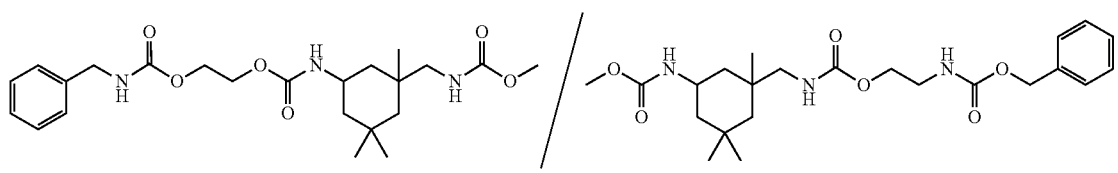
4-40
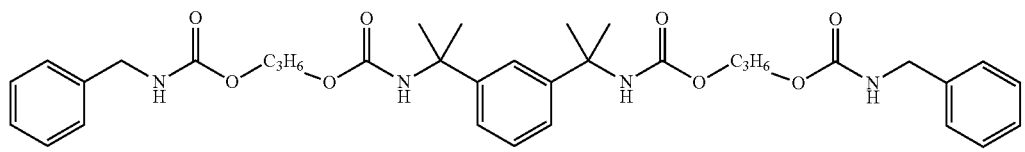
4-41
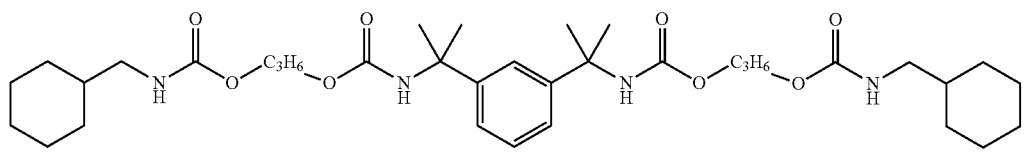
4-42
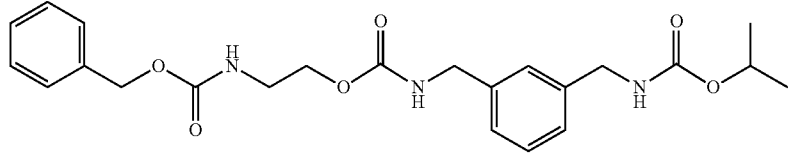
4-43
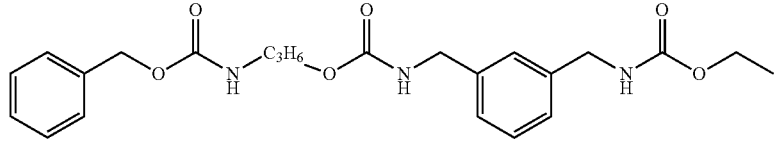

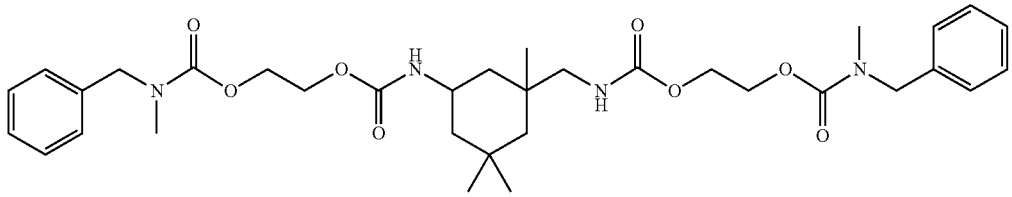

4-44

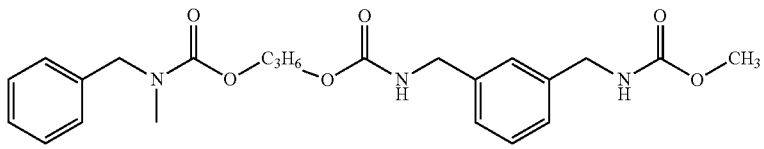

4-45

The compound denoted by general formula (I) can be synthesized by publicy-known methods.

For example, it can be obtained by a reaction that adds an alcohol to an alkyl or an aryl isocyanate, or the condensation reaction of an amine and a carbonate.

In the process of a reaction adding an alcohol to an alkyl or an aryl isocyanate, it is preferable to employ a catalyst. Amines, metal organic acid salts or metal chelate compounds of zinc, tin and the like, organic metal compounds of zinc, tin, or bismuth, or some other conventionally known urethane catalyst can be employed as the catalyst. Examples of urethane catalysts that are preferably employed are dibutyltin dilaurate and dibutyltin diacetate.

A combination of a polyvalent isocyanate (diisocyanate, triisocyanate, or the like) and a monohydric alcohol, and any combination of a polyhydric alcohol and a monovalent isocyanate, is preferably employed as the compound denoted by general formula (I).

Examples of polyvalent isocyanate components are aliphatic diisocyanates such as ethylene diisocyanate, trimethylene diisocyanate, tetramethylene diisocyanate, hexamethylene diisocyanate, and isophorone diisocyanate; aromatic diisocyanates such as p-phenylene diisocyanate, tolylene diisocyanate, p,p'-diphenylmethane diisocyanate, and 1,5-naphthylene diisocyanate; and m-xylylene diisocyanate. However, there is no limitation to these compounds. Of these compounds, from the perspective of inhibiting light tinting, the aliphatic diisocyanates and m-xylylene diisocyanate with a severed conjugation system are preferable.

Examples of monovalent isocyanate components are phenyl isocyanate, benzyl isocyanate, and butyl isocyanate. However, there is no limitation to these compounds.

Examples of polyhydric alcohols are ethylene glycol, diethylene glycol, triethylene glycol, tetraethylene glycol, 1,2-propanediol, 1,3-propanediol, dipropylene glycol, tripopylene glycol, 1,3-butanediol, 1,4-butanediol, 1,5-pentanediol, 1,6-hexanediol, trimethylol propane, trimethylol ethane, and glycerol.

Examples of monohydric alcohols are substituted and unsubstituted alcohols. The alcohol component preferably comprises an aromatic ring; benzyl alcohol, phenethyl alcohol, and phenoxyethanol are examples.

The molecular weight of the compound denoted by general formula (I) preferably falls within a range of 230 to 2,000, more preferably falls within a range of 250 to 1,500, yet more preferably falls within a range of 300 to 1,000, and most preferably, falls within a range of 350 to 800.

When the molecular weight is greater than or equal to 230, there is good inhibition of volatilization from the film. A molecular weight that is less than or equal to 2,000 is preferable in that there is sufficient compatibility with the cellulose acylate and increased haze can be prevented.

The degree to which the compound denoted by general formula (I) is hydrophilic can be denoted as a Log P value. The P in Log P denotes the distribution coefficient in an n-octanol-aqueous system and can be measured using n-octanol and water. However, these distribution coefficients can also be calculated as an estimated C Log P value using a C log P value estimating program (C LOG P program included in PC Models of Daylight Chemical Information Systems Corp.). A C log P of −1.0 to 12.0 is preferable, 1.0 to 10.0 is more preferred, and 2.0 to 8.0 is of most preferable.

Further, the melting point of the compound denoted by general formula (I) is preferably −50 to 250° C., more preferably −30 to 200° C. By remaining within such ranges, the effect of the present invention tends to be more effectively realized.

The method of measuring the melting point is not specifically limited and can be suitably selected from any one of publicy-known methods. An example is the method of conducting measurement with a micro melting point measuring device or the like.

[Cellulose Acylate Film of the Second Aspect]

The cellulose acylate film of the second aspect comprises the compound denoted by general formula (A-100) below. Using such a compound makes it possible to achieve a cellulose acylate film with a hard surface and to reduce the adverse effects of light tinting. In addition, since the above compound can exhibit low volatility, it contributes to providing a film of high transparence.

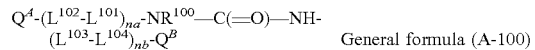

General formula (A-100)

(In general formula (A-100), $R^{100}$ denotes a hydrogen atom or a substituent. Each of $L^{101}$ and $L^{103}$ independently denotes an optionally substituted alkylene group. Each of $L^{102}$ and $L^{104}$ independently denotes a single bond, any one of or any combination of —O—, —NR$^{100a}$—, —S—, and —C(=O)—. $R^{100a}$ denotes a hydrogen atom or a substituent. Each of na and nb independently denotes an integer of 0 to 20; when $L^{101}$, $L^{102}$, $L^{103}$, and $L^{104}$ are present in a plurality of number, the plurality of $L^{101}$, $L^{102}$, $L^{103}$, and $L^{104}$ can be identical or different. Each of $Q^A$ and $Q^B$ independently denotes a substituent, with at least either $Q^A$ or $Q^B$ comprising a ring structure. When na denotes zero and $Q^A$ comprises a ring structure, the ring structure comprised in $Q^A$ can be one that is formed with $R^{100}$ in —NR$^{100}$—.

However, the number of divalent linking groups denoted by —NH—(C=O)—NH— per molecule is 0 or 1.)

The alkylene groups denoted by $L^{101}$ and $L^{103}$ are preferably in the form of alkylene groups having 1 to 20 carbon atoms, more preferably alkylene groups having 1 to 12 carbon atoms, yet more preferably alkylene groups having 1 to 8 carbon atoms, most preferably alkylene groups having 1 to 3 carbon atoms, and ideally methylene groups, ethylene groups, or propylene groups. The alkylene groups can be linear, branched, or cyclic. Specific examples of alkylene groups are methylene groups, ethylene groups, propylene groups, butylene groups, pentylene groups, and hexylene groups. Substituent(s) can be present on the alkylene groups. Substituent group T provides examples of substituents that can be present on the alkylene groups. Of these, preferable substituents on which alkylene groups are present are alkyl groups, acyl groups, aryl groups, alkoxy groups, and carbonyl groups.

Each of $L^{102}$ and $L^{104}$ independently denotes a single bond, any one of or any combination of —O—, —$NR^{100a}$—, —S—, and —C(=O)—. Of these, a single bond or an oxygen atom is preferable. $R^{100a}$ denotes a hydrogen atom or a substituent. Examples of the substituent are an alkyl group, alkenyl group, aryl group, and acyl group. A hydrogen atom, alkyl group having 1 to 8 carbon atoms, alkenyl group having 2 to 8 carbon atoms, alkynyl group having 2 to 8 carbon atoms, or an aryl group having 6 to 18 carbon atoms (such as a group having a benzene ring or naphthalene ring) is preferable, and a hydrogen atom or an alkyl group having 1 to 4 carbon atoms is preferred.

In one embodiment, $L^{102}$ and $L^{104}$ preferably denote single bonds, —O—*, —OC(=O)—*, or —C(=O)O—*. Here, * denotes the position of the bond with $Q^A$ or $Q^B$, or the position of the bond with an adjacent group on the $Q^A$ or $Q^B$ side.

In addition to general formulas (2A) to (2E) below, the structure denoted by general formula (2F) is a specific example of a linking group denoted by ($L^{102}$-$L^{101}$) or ($L^{103}$-$L^{104}$):

—{$R^b_{jb}(CR^aR^c)_{ja}$—O—(C=O)}—*;  General formula (2A)

—{$R^b_{jb}(CR^aR^c)_{ja}$—O}—*;  General formula (2B)

—{$R^b_{jb}(CR^aR^c)_{ja}$—(C=O)O—}—*;  General formula (2C)

—{$R^b_{jb}(CR^aR^c)_{ja}$—$NR^{100a}$(C=O)O—}—*;  General formula (2D)

—{$R^b_{jb}(CR^aR^c)_{ja}$—O—(C=O)$NR^{100a}$}—*;  General formula (2E)

—{$R^b_{jb}(CR^aR^c)_{ja}$—$NR^{100a}$(C=O)$NR^{100a}$}*.  General formula (2F)

(In general formulas (2A) to (2F), * denotes the position of the bond with $Q^A$ or $Q^B$, or the position of the bond with an adjacent group on the $Q^A$ or $Q^B$ side; $R^a$ denotes a hydrogen atom or an alkyl group having 1 to 3 carbon atoms; ja denotes an integer greater than or equal to 1; when $R^a$ $R^a$ are present in a plurality of number, the plurality of $R^a$ and $R^c$ can be identical or different; $R^b$ denotes a cyloalkylene group optionally substituted with one or more alkyl groups having 1 to 3 carbon atoms, and jb denotes 0 or 1. $R^{100a}$ denotes a hydrogen atom or an alkyl group having 1 to 4 carbon atoms; when $R^{100a}$ are present in a plurality of number, the plurality of $R^{100a}$ can be identical or different.)

General formulas (2A) to (2E) are as set forth for the first aspect above. The substituent denoted by $R^1$ in general formulas (2D) and (2E) in the first aspect is denoted by $R^{100a}$ in general formulas (2D) and (2E) in the second aspect.

With regard to general formula (2F), specific examples of the linking group denoted by general formula (2F) are:
-(cyclohexylene group substituted with 1 to 3 alkyl groups having 1 to 3 carbon atoms)-$CH_2$—$NR^{100a}$(C=O)$NR^1$—;
—C($CH_3$)$_2$—$R^1$(C=O)$NR^{100a}$—;
—$CH_2$—$NR^1$(C=O)$NR^{100a}$;
—$CH_2CH_2$—$NR^1$(C=O)$NR^{100a}$—;
—$CH_2CH_2CH_2$—NR(C=O)$NR^{100a}$;
—$CH_2CH(CH_3)$—$NR^1$(C=O)$NR^{100a}$; and
—$CH(CH_3)CH_2$—$NR^1$(C=O)$NR^{100a}$—.

Examples of preferable embodiments of linking groups denoted by ($L^{102}$-$L^{101}$) and ($L^{103}$-$L^{104}$) are alkylene groups and the groups denoted by general formulas (2A) to (2E). In one embodiment, a preferable embodiment is an alkylene group or the group denoted by general formula (2A) or (2B). In another embodiment, preferred embodiments are the groups denoted by general formulas (2D) to (2F). The statement that ($L^{102}$-$L^{101}$) and ($L^{103}$-$L^{104}$) are alkylene groups means that $L^{102}$ and $L^{104}$ denote single bonds and $L^{101}$ and $L^{103}$ denote alkylene groups.

Each of $Q^A$ and $Q^B$ independently denotes a substituent, and at least either $Q^A$ or $Q^B$ comprises a ring structure.

Examples of substituents are provided by substituent group T above. Examples are aryl groups having 6 to 30 (preferably 6 to 20, more preferably 6 to 10) carbon atoms; alkyl groups having 1 to 12 (preferably 1 to 10, more preferably 1 to 6) carbon atoms (it being possible for oxygen atoms to be contained in the alkyl chain, and cycloalkyl groups also being possible); alkenyl groups having 2 to 12 (preferably 2 to 10, more preferably 2 to 5) carbon atoms; alkoxy groups having 1 to 12 (preferably 1 to 10, more preferably 1 to 5) carbon atoms; and hetero ring groups having 1 to 30 (preferably 1 to 12, more preferably 1 to 5) carbon atoms (examples of hetero atoms being nitrogen atoms, oxygen atoms, sulfur atoms; specific examples being piperidyl groups and morpholino groups). It is preferably for one or both of $Q^A$ and $Q^B$ to denote an aryl group having 6 to 10 carbon atoms or an alkyl group having 1 to 10 carbon atoms. $Q^A$ and $Q^B$ can comprise further substituent(s). Specific examples of the substituents are those given in substituent group T above, with aryl groups, alkyl groups, and acyl groups being preferable.

Examples of the ring structure contained in one or both of $Q^A$ and $Q^B$ are aliphatic rings (such as cyclohexane rings), aromatic rings (such as benzene rings or naphthalene rings), and hetero rings (such as piperidine rings and morpholino rings). Multiple types of rings can be present, and the rings can be condensed rings. In one embodiment, the ring structure is preferably not a cyclic imide ring. In another embodiment, it is preferable for at least either $Q^A$ or $Q^B$, preferably both, to not be polar groups. In the present invention, the term "polar group" refers to a substituent with a C log P value of less than or equal to 0.85. The C log P value will be described further below. In the present Specification, the C log P values of $Q^A$ and $Q^B$ are obtained as the C log P values of the compounds in the form of the given substituents connected to hydrogen: $Q^A$-H and $Q^B$-H. It is possible to calculate a C log P value even for a compound with a structure that does not actually exist by estimation using computational chemistry techniques or based on empirical methods. Specific examples of substituents with C log P values that are less than or equal to 0.85 are cyano groups and imide groups.

The ring structure that is contained in one or both of $Q^A$ and $Q^B$ is preferably an aliphatic carbon ring, an aromatic carbon ring, or a hetero ring (preferably a nitrogen-containing six-membered hetero ring), and preferably a cyclohexane ring, benzene ring, or morpholine ring. In general formula (A), when na denotes zero and $Q^A$ contains a ring structure, the ring structure contained in $Q^A$ can be a ring structure (nitrogen-containing hetero ring) formed with R in —NR—. The ring structure thus formed is preferably a nitrogen-containing six-membered hetero ring, more preferably a morpholine ring. The nitrogen-containing hetero ring can be substituted or unsubstituted. An unsubstituted nitrogen-containing hetero ring is preferable. Examples of the substituents in the nitrogen-containing hetero ring are given by substituent group T above. From the perspective of increasing the surface hardness of the cellulose acylate film, the compound denoted by general formula (A) preferably comprises 2 to 4, more preferably 2 or 3, ring structures per molecule.

As set forth above, when na denotes zero and $Q^A$ contains a ring structure in general formula (A-100), the ring structure contained in $Q^A$ can be a ring structure that is formed with $R^{100}$ in —$NR^{100}$—. Embodiments having the above ring structure in the form of the compound denoted by general formula (A) are denoted by general formula (A-100-1) below.

General formula (A-100-1)

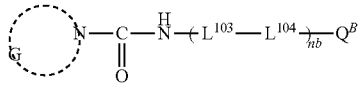

(In general formula (A-100-1), G denotes an atom group forming a ring structure with a nitrogen atom to which the atom group connects. Each of $L^{103}$, $L^{104}$, nb, and $Q^B$ is as defined in general formula (A-100).)

The ring structure (nitrogen-containing hetero ring) formed by G is a substituted or unsubstituted nitrogen-containing hetero ring, preferably in the form of a substituted or unsubstituted nitrogen-containing six-membered ring and more preferably in the form of a substituted or unsubstituted morpholino group. As set forth above, the nitrogen-containing hetero ring is preferably unsubstituted. An embodiment of the compound denoted by general formula (A-100) having an unsubstituted morpholino group is denoted by general formula (A-100-2) below.

General formula (A-100-2)

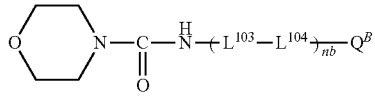

(In general formula (A-100-2), each of $L^{103}$, $L^{104}$, nb, and $Q^B$ is defined as in general formula (A-100).)

Alternatively, $Q^A$ is preferably either a monovalent substituent denoted by general formula (a) below, or a substituent that is bonded to $L^{102}$ through one or more linking groups in the form of this monovalent substituent.

*-$(L^{102}$-$L^{101})_{na}$-$NR^{100}$—C(=O)—NH-
$(L^{103}$-$L^{104})_{nb}$-$Q^B$    General formula (a)

Alternatively, $Q^B$ is preferably either a monovalent substituent denoted by general formula (b) below, or a substituent that is bonded to $L^{104}$ through one or more linking groups in the form of this monovalent substituent.

$Q^A$-$(L^{102}$-$L^{101})_{na}$-$NR^{100}$—C(=O)—NH-
$(L^{103}$-$L^{104})_{nb}$-*    General formula (b)

That is, the compound denoted by general formula (A-100) preferably comprises two or more structure denoted by -$(L^{102}$-$L^{101})_{na}$-$NR^{100}$—C(=O)—NH-$(L^{103}$-$L^{104})_{nb}$- per molecule. In general formulas (a) and (b) above, each of $L^{101}$ to $L^{104}$, na, nb, $Q^A$, and $Q^B$ is as defined in general equation (A-100). Specific embodiments of the compound relating to the above preferable embodiment will be described further below; those described for $Z^{101}$ in general formula (A-101) can serve as examples of the above linking groups.

It suffices for the compound denoted by general formula (A-100) to comprise one or more divalent linking groups denoted by —$NR^{100}$—C(=O)—NH—, while two or more can also be present. Here, $R^{100}$ denotes a hydrogen atom or a substituent. Substituent group T above provides examples of the substituent denoted by $R^{100}$. It is preferably an alkyl group, more preferably an alkyl group having 1 to 3 carbon atoms, and most preferably a methyl group. The alkyl group can comprise substituent(s). A substituent in the form of an aryl group is preferable; an example is a phenyl group.

However, the compound denoted by general formula (A-100) does not comprise two or more of the above divalent linking groups in which $R^{100}$ is a hydrogen atom. That is, in the compound denoted by general formula (A-100), the number of divalent linking groups denoted by —NH—C(=O)—NH— per molecule is 0 or 1. That is because a compound comprising two or more divalent linking groups denoted by —NH—C(=O)—NH— per molecule, despite comprising the structure denoted by general formula (A-100), will have poor compatibility with cellulose acylate.

The compound denoted by general formula (A-100) can contain a divalent linking group denoted by —NH—C(=O)—O— together with the above divalent linking group. The divalent linking group denoted by —$NR^{100}$—C(=O)—O— and the divalent linking group denoted by —NH—C(=O)—O— are groups that can interact with cellulose acylate. The present inventors assume that the fact that these linking groups can interact with local portions of cellulose acylate such as the ester bond and/or the hydroxyl group, as well as the polymer chain, reducing the interspace of the cellulose acylate film, contribute to increasing the surface hardness of the cellulose acylate film.

The compound denoted by general formula (A-100) preferably contains the above linking group in a proportion such that the equivalent U, calculated as U=((molecular weight)/(total number of divalent linking groups denoted by —NH—(C=O)—$NR^{100}$— and divalent linking groups denoted by —NH—C(=O)—O— contained per molecule)), is less than or equal to 515. The lower the value of equivalent U, the greater the content of the above linking group per molecule. As set forth above, the above linking group can contribute to increasing the surface hardness of cellulose acylate by interacting with cellulose acylate; at a proportion at which equivalent U is less than or equal to 515, the compound denoted by general formula (A-100) containing the above linking group can further increase the surface hardness of cellulose acylate. The value of the equivalent U is preferably less than or equal to 450, more preferably less than or equal to 420, and most preferably, less than or equal to 300. The lower limit is not specifically specified, and can be, for example, greater than or equal to 100.

In a preferable embodiment, the compound denoted by general formula (A-100) comprises two or more of the divalent linking groups denoted by —NH—(C=O)—NR$^{100}$— per molecule, preferably two. In another preferable embodiment, it comprises 2 to 4. In yet another preferable embodiment, the compound denoted by general formula (A) contains one or more each of the divalent linking group denoted by —NH—(C=O)—NR— and the divalent linking group denoted by —NH—(C=O)—O—, preferably one each.

In another preferable embodiment, the nitrogen atom is not directly bonded to the aromatic ring in the divalent linking group denoted by —NH—(C=O)—NR$^{100}$— in the compound denoted by general formula (A-100). In yet another preferable embodiment, the divalent linking group denoted by —NH—(C=O)—O— is not directly bonded to the aromatic ring by the nitrogen atom or the oxygen atom, in the compound denoted by general formula (A-100). These preferable embodiments make it possible to more effectively inhibit light tinting. It is preferable for two or more of the divalent linking groups not to be directly bonded to a single aromatic ring. That is, it is preferable for the compound denoted by general formula (A-100) not to comprise the structures denoted by aromatic ring-NH—(C=O)—NR$^{100}$—, —NH—(C=O)—NR$^{100}$-aromatic ring, aromatic ring-NH—(C=O)—O—, and —NH—(C=O)—O— aromatic ring.

Each of na and nb independently denotes an integer of 0 to 20. Both na and nb can denote zero, or either na or nb can denote an integer of greater than or equal to 1. Each of na and nb preferably denotes an integer of 0 to 10, more preferably denotes an integer of 0 to 5, and most preferably denotes an integer of 0 to 3.

The compound denoted by general formula (A-100) is preferably a compound denoted by general formula (A-101) below.

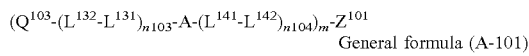
General formula (A-101)

(In general formula (A-101), each of L$^{131}$ and L$^{141}$ independently denotes an optionally substituted alkylene group. Each of L$^{132}$ and L$^{142}$ independently denotes a single bond, any one of or any combination of —O—, —NR$^{100a}$—, —S—, and —C(=O)—. R$^{100a}$ denotes a hydrogen atom or a substituent. Each of n103 and n104 independently denotes an integer of 0 to 20; when L$^{131}$, L$^{132}$, L$^{141}$, and L$^{142}$ are present in a plurality of number, the plurality of L$^{131}$, L$^{132}$, L$^{141}$, and L$^{142}$ can be identical or different. Q$^{103}$ denotes a substituent and Z$^{101}$ denotes a linking group of valence m. A denotes *—NR$^{100}$—C(=O)—NH—, *—NH—C(=O)—NR$^{100}$—, *—O—C(=O)—NH—, or * NH—C(=O)—O—. R$^{100}$ denotes a hydrogen atom or a substituent. * denotes the position of the bond with L$^{141}$ or Z$^{101}$. m2 denotes an integer of 2 to 6; the plurality of Q$^{103}$ and A can be identical or different. However, at least one of A denotes *—NR$^{100}$—C(=O)—NH— or *—NH—C(=O)—NR$^{100}$—. At least either Q$^{103}$ or Z$^{101}$ contains a ring structure. When at least one of n103 denotes zero, Q$^{103}$ denotes a ring structure, and A denotes *—NH—C(=O)—NR$^{100}$, the ring structure that is contained in Q$^{103}$ can be a ring structure formed with the R$^{100}$ in —NR$^{100}$-contained in A. However, the number of divalent linking groups denoted by —NH—(C=O)—NH-per molecule is 0 or 1.)

Each of L$^{131}$ and L$^{141}$ is independently defined identically with L$^{101}$ and L$^{103}$ in general formula (A-100). At least either L$^{131}$ or L$^{141}$ is preferably an alkylene group identically defined with L$^{101}$ or L$^{103}$ in general formula (A-100), and both are more preferably alkylene groups identically defined with L$^{101}$ and L$^{103}$ in general formula (A-100).

Each of L$^{132}$ and L$^{142}$ is independently defined identically with L$^{102}$ and L$^{104}$ in general formula (A-100), and their preferable ranges are identical.

Specifically, the linking group denoted by (L$^{141}$-L$^{142}$) is preferably a single bond or an alkylene group, and the linking group denoted by (L$^{32}$-L$^{31}$) is preferably a single bond, alkylene group, or any of the groups denoted by general formulas (2A) to (2F) below. Details regarding general formulas (2A) to (2F) are as set forth above:

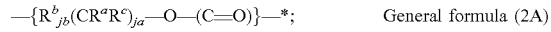   General formula (2A)

   General formula (2B)

   General formula (2C)

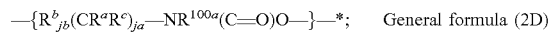   General formula (2D)

   General formula (2E)

   General formula (2F)

(In general formulas (2A) to (2F), * denotes the position of the bond with Q$^{103}$ or the position of the bond with an adjacent group on the Q$^{103}$ side; and R$^a$, R$^c$, R$^b$, ja, and jb are as set forth above.)

n103 and n104 are defined identically with na and nb in general formula (A-100) and have the same preferable ranges.

m is an integer of 2 to 6, preferably an integer of 2 to 3.

Q$^{103}$ denotes a substituent, preferably a linear or branched alkyl group having 1 to 30 carbon atoms or a cyclic group having 6 to 30 carbon atoms. Q$^3$ can further comprise substituent(s). Specific examples of the substituents are provided by substituent group T above; an aryl group, alkyl group, acyl group, or alkoxy group is preferable. However, it is preferable for Q$^3$ not to comprise a substituent.

The cyclic group contained in Q$^{103}$ can be a condensed ring, but monocyclic system is preferable. Specific examples are aliphatic rings (cyclohexane rings and the like), aromatic rings (such as benzene rings and naphthalene rings), and hetero rings (such as morpholine rings, piperidine rings, piperazine rings, pyridine rings, pyrimidine rings, triazine rings, and furan rings).

In general formula (A-101), since m denotes an integer falling within a range of 2 to 6, the compound denoted by general formula (A-101) contains multiple (m) instances of Q$^{103}$. The plurality of Q$^{103}$ can be identical or different. The plurality of Q$^{103}$ can all be ring structures, or can be a combination of a ring structure and an a ring structure such as an alkyl group. The ring structure is preferably contained in the form of an aliphatic cyclic group, aromatic cyclic group, or nitrogen-containing six-membered hetero ring. The cyclic group denoted by Q$^3$ is preferably in the form of a cycloalkyl group having 6 to 30 (preferably 6 to 20, more preferably 6 to 10) carbon atoms, an aryl group having 6 to 30 (preferably 6 to 20, more preferably 6 to 10) carbon atoms, or a nitrogen-containing six-membered hetero ring, and preferably in the form of a cyclohexyl group, phenyl group, or morpholino group.

Further, the acyclic structure is preferably in the form of a linear or branched alkyl group having 1 to 30 carbon atoms, more preferably in the form of an alkyl group having 1 to 3 carbon atoms, and most preferably, in the form of a methyl group or ethyl group.

At least one from among the plurality of Q$^{103}$ or Z$^{101}$ comprises one or more ring structures; it is preferable for Z$^{101}$ and one or more of the plurality of Q$^{103}$ that are present to contain a ring structure. It is preferable for having 2 to 4 ring structures to be present in $Q^{103}$ and $Z^{101}$, and more preferable for having 2 or 3 ring structures to be present.

A denotes *—$NR^{100}$—C(=O)—NH—, *—NH—C(=O)—$NR^{100}$—, *—O—C(=O)—NH—, or *—NH—C(=O)—O—, with * denoting the position of the bond with $L^{141}$ or $Z^{101}$. As set forth above, m denotes an integer of 2 to 6. Thus, multiple (m) instances of A are present in the compound denoted by general formula (A-101). The plurality of A that are present can be identical or different. However, at least one of A denotes *—$NR^{100}$—C(=O)—NH— or *—NH—C(=O)—$NR^{100}$—. $R^{100}$ is as set forth above.

$Z^{101}$ denotes a linking group of valence m. Since m is an integer falling within a range of 2 to 6, $Z^{101}$ is a linking group of valence 2 to 6. It is preferably a linking group of valence 2 to 3, more preferably a divalent linking group. $Z^{101}$ is preferably in the form of a group comprising at least one linear, branched, or alicyclic group or aromatic group, more preferably in the form of a group comprising at least one branched or alicyclic group or aromatic group.

$Z^{101}$ can be comprised of at least one or any combination of a linear, branched, or alicyclic group or aromatic group. It is also preferable for these groups to be combined with oxygen atoms and linear or branched alkylene groups. The aliphatic group that is incorporated as $Z^{101}$ is preferably a saturated aliphatic group.

Employing a group comprising at least one selected from a branched or alicyclic group and an aromatic group results in a rigid structure and tends to increase the surface hardness of the film. The number of carbon atoms constituting $Z^1$ is preferably 3 to 20, more preferably 4 to 15.

$Z^{101}$ can comprise a substituent. Specific examples of the substituent are those provided by substituent group T above. However, it is preferable for no substituent to be present.

Specifically, the linking groups given by way of example below are preferable. * denotes the position of the bond with $L^{142}$ (or the direct bond with A when $L^{141}$ is not present).

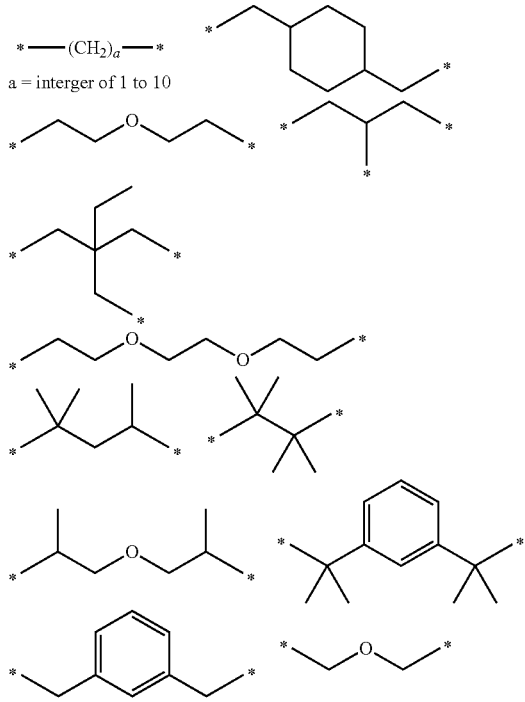

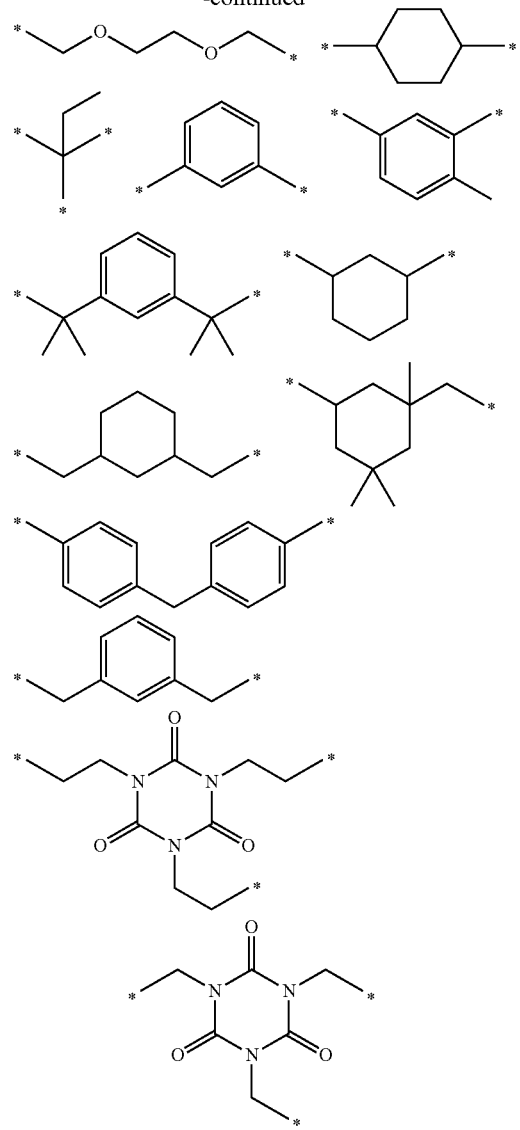

The compound denoted by general formula (A-101) preferably contains a ring structure selected from the group consisting of an aliphatic carbon ring, aromatic carbon ring, and hetero ring. In the compound denoted by general formula (A-101), all of the instances of $Q^{103}$ can have a cyclic group selected from the group consisting of cycloalkyl groups (preferably cyclohexyl groups), aromatic groups (preferably a phenyl group), and nitrogen-containing heterocyclic groups (preferably nitrogen-containing six-membered hetero rings and preferably a morpholino group), and preferably denotes these cyclic groups, or $Z^{101}$ preferably comprises a alicyclic group or aromatic group. The above cycloalkyl group is preferably an unsubstituted cycloalkyl group, more preferably an unsubstituted cyclohexyl group. The above aromatic group is preferably in the form of an unsubstituted aromatic group, more preferably in the form of an unsubstituted phenyl group. It is preferable for a alicyclic group to be present on $Z^{101}$, and more preferable for $Z^{101}$ to be comprised of a alicyclic group.

The embodiment of the above nitrogen-containing hetero ring in the compound denoted by general formula (A-101) can comprise the partial structure given below.

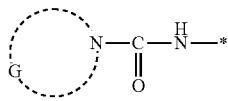

In the above formula, G denotes an atom group forming a ring structure (nitrogen-containing hetero ring) with a nitrogen atom to which the atom group connects, and * denotes the position of the bond with the other structure constituting the compound denoted by general formula (A-101). The nitrogen-containing hetero ring formed by G is preferably a substituted or unsubstituted nitrogen-containing hetero ring in the form of a substituted or unsubstituted nitrogen-containing six-membered hetero ring and more preferably in the form of a substituted or unsubstituted morpholino group. The nitrogen-containing hetero ring is preferably unsubstituted. The embodiment of the compound denoted by general formula (A-101) comprising an unsubstituted morpholino group can comprise the following partial structure. In the following partial structure, * denotes the position of the bond with the other structure constituting the compound denoted by general formula (A-101).

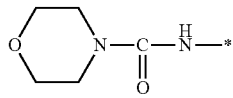

The compound denoted by general formula (A-101) is preferably the compound denoted by general formula (A-102) below.

General formula (A-102)

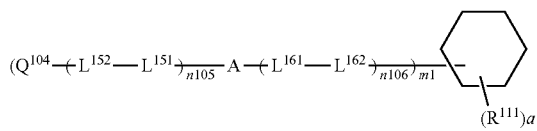

(In general formula (A-102), each of $L^{151}$ and $L^{161}$ independently denotes an optionally substituted alkylene group. Each of $L^{152}$ and $L^{162}$ independently denotes a single bond; any one of or any combination of —O—, —NR$^1$—, —S—, and —C(=O)—. $R^{100a}$ denotes a hydrogen atom or a substituent. Each of n105 and n106 independently denotes an integer of 0 to 20; when $L^{151}$, $L^{152}$, $L^{161}$, and $L^{162}$ are present in a plurality of number, the plurality of $L^{151}$, $L^{152}$, $L^{161}$, and $L^{162}$ can be identical or different. $Q^{104}$ denotes a substituent. A denotes *—NR$^{100}$—C(=O)—NH—, *—NH—C(=O)—NR$^{100}$—, *—O—C(=O)—NH—, or *—NH—C(=O)—O—. $R^{100}$ denotes a hydrogen atom or a substituent. * denotes the position of the bond with a cyclohexane ring optionally substituted with $(R^{111})a$. $R^{111}$ denotes an alkyl group having 1 to 3 carbon atoms. m1 denotes 2 or 3. The plurality of $Q^{104}$ and A can be identical or different. However, at least any one of A denotes *—NR$^{100}$—C(=O)—NH— or *—NH—C(=O)—NR—. Further, when at least any one of n105 denotes zero, $Q^{104}$ contains a ring structure, and A denotes *—NH—C(=O)—NR$^{100}$, the ring structure contained in $Q^{104}$ can be a ring structure that is formed with the $R^{100}$ in the —NR$^{100}$— that is contained in A. However, the number of divalent linking groups denoted by —NH—(C=O)—NH-per molecule is 0 or 1. a denotes an integer falling within a range of 0 to 10. When a is greater than or equal to 1, the plurality of $R^{111}$ that are present can be identical or different.)

$Q^{104}$ denotes a substituent, is identically defined with $Q^4$ in general formula (A-100), and has the same preferable range.

Each of $L^{51}$ and $L^{161}$ is independently defined identically with $L^{101}$ and $L^{103}$ in general formula (A-100) and has the same preferable range.

Each of $L^{152}$ and $L^{162}$ is independently defined identically with $L^{102}$ and $L^{104}$ in general formula (A-100) and has the same preferable range.

Each of n105 and n106 is independently defined identically with na and nb in general formula (A-100) and has the same preferable range.

The linking group denoted by ($L^{152}$-$L^{151}$) is identical to the linking group denoted by ($L^{32}$-$L^{31}$) in general formula (A-101) and has the same preferable range.

The linking group denoted by ($L^{161}$-$L^{162}$) is identical to the linking group denoted by ($L^{141}$-$L^{142}$) in general formula (A-101) and has the same preferable range.

$R^{111}$ denotes an alkyl group having 1 to 3 carbon atoms, such as a methyl group, ethyl group, propyl group, or isopropyl group. $R^{111}$ is preferably a methyl group.

m1 denotes 2 or 3, and is preferably 2. a denotes an integer of 0 to 10, more preferably 0 to 5, yet more preferably 0 to 3, and most preferably, 1 to 3.

Specific examples of the positions of the two or three side chain bonds in the cyclohexane ring in general formula (A-102) are given below.

Below, * denotes the position at which the cyclohexane ring connects to the following structure.

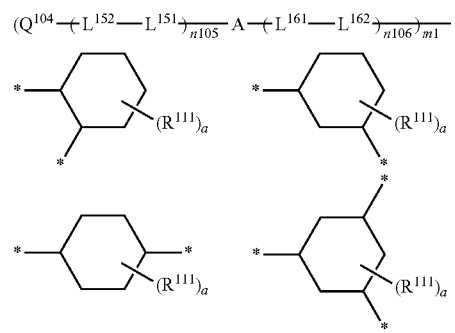

The above cyclohexane ring is preferably the structure indicated below.

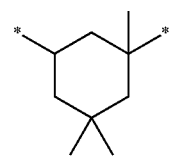 [SMILES: *C1CC(*)(C)CC(C)(C)C1]

The compound denoted by general formula (A-103) below is an example of a preferable form of the compound denoted by general formula (A-101).

General formula (A-103)

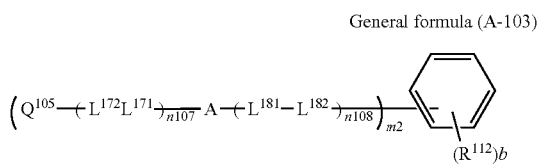

(In general formula (A-103), each of $L^{171}$ and $L^{181}$ independently denotes an optionally substituted alkylene group. Each of $L^{172}$ and $L^{182}$ independently denotes a single bond; any combination of —O—, —NR$^{100}$—, —S—, and —C(=O)—. $R^{100a}$ denotes a hydrogen atom or a substituent. Each of n107 and n108 independently denotes an integer of 0 to 20; when $L^{171}$, $L^{172}$, $L^{181}$, and $L^{182}$ are present in a plurality of number, the plurality of $L^{171}$, $L^{172}$, $L^{181}$, and $L^{182}$ can be identical or different. $Q^{105}$ denotes a substituent. A denotes *—NR$^{100}$—C(=O)—NH—, *—NH—C(=O)—NR$^{10}$—, *—O—C(=O)—NH—, or *—NH—C(=O)—O—. $R^{100}$ denotes a hydrogen atom or a substituent. * denotes the position of the bond with $L^{181}$ or with a cyclohexane ring optionally substituted with $(R^{112})b$. $R^{112}$ denotes an alkyl group having 1 to 3 carbon atoms. m2 denotes 2 or 3. The plurality of $Q^{105}$ and A can be identical or different. However, at least one of A denotes *—NR$^{100}$—C(=O)—NH— or *—NH—C(=O)—NR—. Further, when at least one of n107 denotes zero, $Q^{105}$ contains a ring structure, and A denotes *—NH—C(=O)—NR$^{100}$, the ring structure contained in $Q^{105}$ can be a ring structure that is formed with the $R^{100}$ in the —NR$^{100}$— that is contained in A. However, the number of divalent linking groups denoted by —NH—(C=O)—NH-per molecule is 0 or 1. b denotes an integer falling within a range of 0 to 5. When b is greater than or equal to 1, the plurality of $R^{112}$ can be identical or different.)

$Q^{105}$ denotes a substituent, is defined identically with $Q^A$ in general formula (A-100), and has the same preferable range.

Each of $L^{171}$ and $L^{181}$ is independently defined identically with $L^{101}$ and $L^{103}$ in general formula (A-100) and has the same preferable range.

Each of $L^{172}$ and $L^{182}$ is independently defined identically with $L^{102}$ and $L^{104}$ in general formula (A-100) and has the same preferable range.

Each of n107 and n108 is independently defined identically with na and nb in general formula (A-100) and has the same preferable range.

The linking group denoted by $(L^{72}-L^{71})$ is identical to the linking group denoted by $(L^{132}-L^{131})$ in general formula (A-101) and has the same preferable range.

The linking group denoted by $(L^{181}-L^{182})$ is identical to the linking group denoted by $(L^{141}-L^{142})$ in general formula (A-101) and has the same preferable range.

$R^{112}$ denotes an alkyl group having 1 to 3 carbon atoms, such as a methyl group, ethyl group, propyl group, or isopropyl group. $R^{112}$ is preferably a methyl group.

m2 denotes 2 or 3, and is preferably 2.

b denotes an integer of 0 to 5, preferably 0 to 3, and more preferably, 0.

Specific examples of the position of the bonds of the two or three side chains in the benzene ring in general formula (A-103) are given below.

Below, * denotes the position at which the benzene ring connects to the following structure.

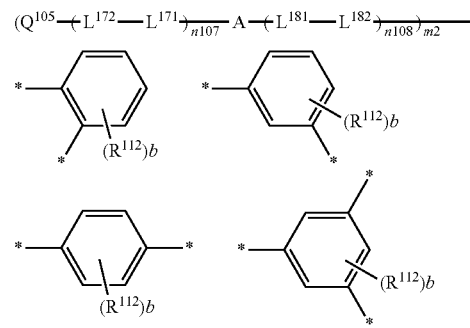

The compound denoted by general formula (A-103) set forth above preferably comprises the following partial structure.

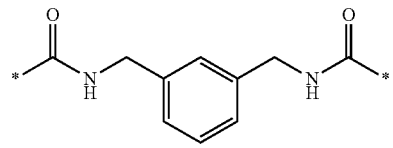

(In the above, * denotes the position of a bond with other structure constituting the compound denoted by general formula (A-103)).

Further, the compound denoted by general formula (A-102) and the compound denoted by general formula (A-103) preferably comprise the partial structure containing a nitrogen-containing hetero ring set forth above.

Examples of preferable embodiments of the compound denoted by general formula (A-100) are the compound denoted by general formula (A-104-A) below, the compound denoted by general formula (A-104-B), below, and the compound denoted by general formula (A-105) below.

General formula (A-104-A)

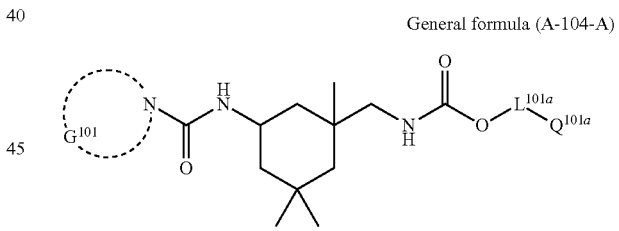

General formula (A-104-B)

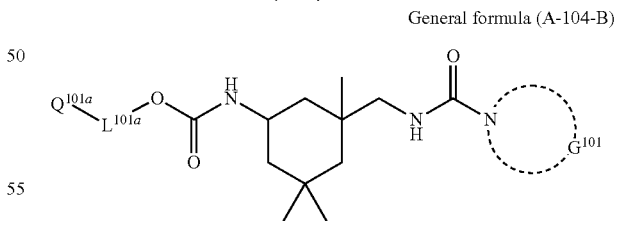

In general formulas (A-104-A) and (A-104-B), $L^{101a}$ denotes a single bond, alkylene group, any one of the groups denoted by general formulas (2A) to (2F) below, or a group comprised of a combination of two or three groups denoted by any of general formulas (2A) to (2F) below and an alkylene group. Details regarding general formulas (2A) to (2F) are as set forth above.

—{$R^b_{jb}(CR^aR^c)_{ja}$—O—(C=O)}—*  General formula (2A)

—{$R^b_{jb}(CR^aR^c)_{ja}$—O}—*  General formula (2B)

—{R$^b_{jb}$(CR$^a$R$^c$)$_{ja}$—(C=O)O—}—*  General formula (2C)

—{R$^b_{jb}$(CR$^a$R$^c$)$_{ja}$—NR$^{100a}$(C=O)O—}—*  General formula (2D)

—{R$^b_{jb}$(CR$^a$R$^c$)$_{ja}$—O—(C=O)NR$^{100a}$}—*  General formula (2E)

—{R$^b_{jb}$(CR$^a$R$^c$)$_{ja}$—NR$^{100a}$(C=O)NR$^{100a}$}—*
General formula (2F)

(In general formulas (2A) to (2F), * denotes the position of the bond with Q$^{101a}$ or the position of the bond with an adjacent group on the Q$^{101a}$ side; each of R$^a$ and R$^c$ independently denotes a hydrogen atom or an alkyl group having 1 to 3 carbon atoms; ja denotes an integer greater than or equal to 1; when R$^a$ and R$^c$ are present in a plurality of number, the plurality of R$^a$ and R$^c$ can be identical or different; R$^b$ denotes a cyloalkylene group optionally substituted with one or more alkylene groups having 1 to 3 carbon atoms; jb denotes 0 or 1; R$^{100a}$ denotes a hydrogen atom or an alkyl group having 1 to 4 carbon atoms; when R$^{100a}$ are present in a plurality of number, the plurality of R$^{100a}$ can be identical or different. However, the number of divalent linking groups denoted by —NH—C(=O)—NH—) per molecule is 0 or 1.)

L$^{101a}$ preferably denotes a single bond, methylene group, ethylene group, a single group denoted by any one of general formulas (2A) to (2F), or a group comprising a combination of two or three groups denoted by any of (2A) to (2F) and an alkylene group.

Q$^{101a}$ denotes a substituent. Details regarding Q$^{101a}$ are as set forth for Q$^A$ in general formula (A-100).

G$^{101}$ denotes an atom group forming a ring structure with a nitrogen atom to which the atom group connects. Details regarding G$^{101}$ are as set forth for G in the partial structure that can be contained in general formula (A-1).

In one embodiment, in general formulas (A-104-A) and (A-104-B), L$^{101a}$ denotes a single bond, alkylene group, any one of the groups denoted by general formulas (2A-1) to (2F-1) below, a group comprising a combination of two or more groups denoted by any of general formulas (2A-1) to (2F-1) below, or a group comprising a combination of one or more alkylene group and one or more group denoted by any of general formulas (2A-1) to (2F-1) below. These combinations can be, for example, combinations of two or three of the above groups.

—{(CR$^a$R$^c$)$_{ja}$—O—(C=O)}—*  General formula (2A-1)

—{(CR$^a$R$^c$)$_{ja}$—O}—*  General formula (2B-1)

—{(CR$^a$R$^c$)$_{ja}$—(C=O)O—}—*  General formula (2C-1)

—{(CR$^a$R$^c$)$_{ja}$—NR$^{100a}$(C=O)O—}—*  General formula (2D-1)

—{(CR$^a$R$^c$)$_{ja}$—O—(C=O)NR$^{100a}$}—*  General formula (2E-1)

—{(CR$^a$R$^c$)$_{ja}$—NR$^1$(C=O)NR$^{100a}$}—*  General formula (2F-1)

(In general formulas (2A-1) to (2F-1), * denotes the position of the bond with Q$^{1a}$ or Q$^{1b}$, or the position of the bond with an adjacent group on the Q$^{1a}$ or Q$^{1b}$ side; each of R$^a$ and R$^c$ independently denotes a hydrogen atom or an alkyl group having 1 to 3 carbon atoms; ja denotes an integer greater than or equal to 1; when R$^a$ and R$^c$ are present in a plurality of number, the plurality of R$^a$ and R$^c$ can be identical or different. R$^{100a}$ denotes a hydrogen atom or an alkyl group having 1 to 4 carbon atoms; when R$^{100a}$ are present in a plurality of number, the plurality of R$^{100a}$ can be identical or different.)

L$^{101a}$ preferably denotes a single bond, an alkylene group, or a group comprising a combination of two groups denoted by any of general formulas (2A-1) to (2F-1); and more preferably denotes a single bond, an alkylene group, or a group denoted by any of general formulas (2A-1) to (2C-1).

General formula (A-105)

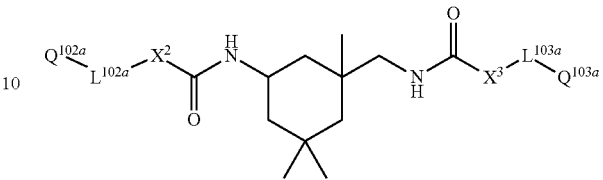

In general formula (A-105), each of L$^{102a}$ and L$^{103a}$ independently denotes a single bond; an alkylene group, a group comprising a combination of two or more groups denoted by any one of general formulas (2A) to (2F) below, or a group comprising a combination of one or more alkylene groups and one or more groups denoted by any of general formulas (2A) to (2F) below. The above combination is, for example, a combination comprising two or three of the above groups. Details regarding general formulas (2A) to (2F) are as set forth above.

—{R$^b_{jb}$(CR$^a$R$^c$)$_{ja}$—O—(C=O)}—*  General formula (2A)

—{R$^b_{jb}$(CR$^a$R$^c$)$_{ja}$—O}—*  General formula (2B)

—{R$^b_{jb}$(CR$^a$R$^c$)$_{ja}$—(C=O)O—}—*  General formula (2C)

—{R$^b_{jb}$(CR$^a$R$^c$)$_{ja}$—NR$^{100a}$(C=O)O—}—*  General formula (2D)

—{R$^b_{jb}$(CR$^a$R$^c$)$_{ja}$—O—(C=O)NR$^{100a}$}—*  General formula (2E)

—{R$^b_{jb}$(CR$^a$R$^c$)$_{ja}$—NR$^{100a}$(C=O)NR$^{100a}$}—*
General formula (2F)

(In general formulas (2A) to (2F), * denotes the position of the bonds with Q$^{102a}$ and Q$^{103a}$ or the position of the bonds with adjacent groups on the Q$^{102a}$ and Q$^{103a}$ sides; each of R$^a$ and R$^c$ independently denotes a hydrogen atom or an alkyl group having 1 to 3 carbon atoms; ja denotes an integer greater than or equal to 1; when R$^a$ and R$^c$ are present in a plurality of number, the plurality of R$^a$ and R$^c$ can be identical or different; R$^b$ denotes a cyloalkylene group optionally substituted with one or more alkyl groups having 1 to 3 carbon atoms; jb denotes 0 or 1; and R$^{100a}$ denotes a hydrogen atom or an alkyl group having 1 to 4 carbon atoms; when R$^{100a}$ are present in a plurality of number, the plurality of R$^{100a}$ can be identical or different. However, the number of divalent linking groups denoted by —NH—(C=O)—NH-per molecule is 0 or 1.)

Each of L$^{102a}$ and L$^{103a}$ independently denotes preferably a single bond, methylene group, ethylene group, single group denoted by any one of general formulas (2A) to (2F), or a group comprising a combination of two or three groups denoted by any of general formulas (2A) to (2F) and one or more alkylene groups.

Each of Q$^{102a}$ and Q$^{103a}$ independently denotes a substituent. Details regarding Q$^{102a}$ and Q$^{103a}$ are as set forth for Q$^A$ in general formula (A-100).

Each of X$^2$ and X$^3$ independently denotes —NR$^{100}$— or —O—. In one embodiment, X$^2$ and X$^3$ both denote —NR$^{100}$—. In another embodiment, either X$^2$ or X$^3$ denotes —NR$^{100}$— and the other denotes —O—. In still another embodiment, both X$^2$ and X$^3$ denote —O—. R$^{100}$ denotes a hydrogen atom or substituent. R$^{100}$ is as described for R$^{100}$ in general formula (A-100). However, when both X$^2$ and X$^3$ denote —O—, one or both of $L^{102a}$ and $L^{103a}$ comprise a divalent linking group denoted by —$NR^{100a}$—C(=O)—NH—. $R^{100a}$ denotes a hydrogen atom or an alkyl group having 1 to 4 carbon atoms. As set forth above, the number of divalent linking groups denoted by —NH—(C=O)—NH— per molecule is 0 or 1.

In one embodiment, in general formula (A-105), each of $L^{102a}$ and $L^{103a}$ independently denotes a single bond, an alkylene group, a group denoted by any of general formulas (2A-1) to (2F-1) below, a group comprising a combination of two or more groups denoted by any of general formulas (2A-1) to (2F-1), or a group comprising a combination of one or more alkylene groups and one or more groups denoted by any of general formulas (2A-1) to (2F-1). The above combination can be comprised of two or three of the above groups.

—{$(CR^aR^c)_{ja}$—O—(C=O)}—*  General formula (2A-1)

—({$(CR^aR^c)_{ja}$—O}—*  General formula (2B-1)

—{$(CR^aR^c)_{ja}$—(C=O)O—}—*  General formula (2C-1)

—{$(CR^aR^c)_{ja}$—$NR^{100a}$(C=O)O—}—*  General formula (2D-1)

—{$(CR^aR^c)_{ja}$—O—(C=O)$NR^{100a}$}—*  General formula (2E-1)

—{$(CR^aR^c)_{ja}$—$NR^1$(C=O)$NR^{100a}$}—*  General formula (2F-1)

(In general formulas (2A-1) to (2F-1), * denotes the position of the bond with $Q^{102a}$ or $Q^{103a}$ or the position of the bond with an adjacent group on the $Q^{102a}$ or $Q^{103a}$ side; each of $R^a$ and $R^c$ independently denotes a hydrogen atom or an alkyl group having 1 to 3 carbon atoms; ja denotes an integer greater than or equal to 1; when $R^a$ and $R^c$ are present in a plurality of number, the plurality of $R^a$ and $R^c$ can be identical or different; and $R^{100a}$ denotes a hydrogen atom or an alkyl group having 1 to 4 carbon atoms; when $R^{100a}$ are present in a plurality of number, the plurality of $R^{100a}$ can be identical or different.)

Each of $L^{102a}$ and $L^{103a}$ independently denotes preferably a single bond, alkylene group, or a group comprised of a combination of two divalent linking groups denoted by any of general formulas (2A-1) to (2F-1).

In one embodiment, each of $L^{102a}$ and $L^{103a}$ independently denotes a group denoted by any of general formulas (2A-1) to (2F-1) below, a group comprising a combination of two or more groups denoted by any of general formulas (2A-1) to (2F-1) below, or a group comprising a combination of one or more alkylene groups and one or more groups denoted by any of general formulas (2A-1) to (2F-1) below. The above combination can be comprised of two or three of the above groups.

The compounds set forth above are all useful as additives for cellulose acylate films.

Examples of the compound denoted by general formula (A-100) that are preferably employed in the present invention are given below. However, the present invention is not limited to these compounds.

TABLE 1

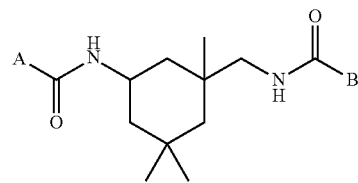

| Compound No. | A | B |
|---|---|---|
| 101-1-A | *—$NHC_2H_5$ | *—$OCH_2CH_2OPh$ |
| 101-2-A | *—$N(C_2H_5)_2$ | *—$OCH_2CH_2OPh$ |
| 101-3-A | *—$NHCH_2Ph$ | *—$OCH_2CH_2OPh$ |
| 101-4-A | *—NH—cHex | *—$OCH_2CH_2OPh$ |
| 101-5-A | *—$N(CH^3)CH_2Ph$ | *—$OCH_2CH_2OPh$ |
| 101-6-A | *—$N(CH_3)_2$ | *—$OCH_2CH_2OPh$ |
| 101-7-A | *—$N(C_3H_7)_2$ | *—$OCH_2CH_2OPh$ |
| 101-8-A | *—NHPh | *—$OCH_2CH_2OPh$ |
| 101-9-A | *—N(morpholino) | *—$OCH_2CH_2OPh$ |
| 101-10-A | *—$NHCH_2Ph$ | *—$OCH(CH_3)CH_2OCOPh$ |
| 101-11-A | *—$NHCH_2Ph$ | *—OCH2CH2OCOPh |
| 101-12-A | *—$NHCH_2Ph$ | *—$N(C_2H_5)_2$ |
| 101-13-A | *—N(morpholino) | *—NH—cHex |
| 1-1-B | *—$OCH_2CH_2OPh$ | *—$NHC_2H_5$ |
| 1-2-B | *—$OCH_2CH_2OPh$ | *—$N(C_2H_5)_2$ |
| 1-3-B | *—$OCH_2CH_2OPh$ | *—$NHCH_2Ph$ |
| 1-4-B | *—$OCH_2CH_2OPh$ | *—NH—cHex |
| 1-5-B | *—$OCH_2CH_2OPh$ | *—$N(CH^3)CH_2Ph$ |
| 1-6-B | *—$OCH_2CH_2OPh$ | *—$N(CH_3)_2$ |
| 1-7-B | *—$OCH_2CH_2OPh$ | *—$N(C_3H_7)_2$ |
| 1-8-B | *—$OCH_2CH_2OPh$ | *—NHPh |
| 1-9-B | *—$OCH_2CH_2OPh$ | *—N(morpholino) |
| 1-10-B | *—$OCH(CH_3)CH_2OCOPh$ | *—$NHCH_2Ph$ |
| 1-11-B | *—$OCH_2CH_2OCOPh$ | *—$NHCH_2Ph$ |
| 1-12-B | *—$N(C_2H_5)_2$ | *—$NHCH_2Ph$ |
| 1-13-B | *—NH—cHex | *—N(morpholino) |

(In the table, Ph: phenyl group, cHex: cyclohexyl group, *: bonding position)

101-20
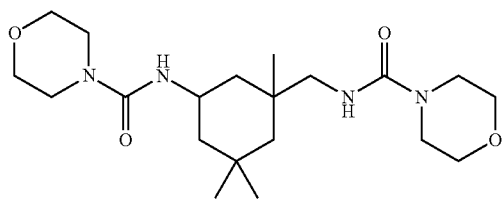
101-21
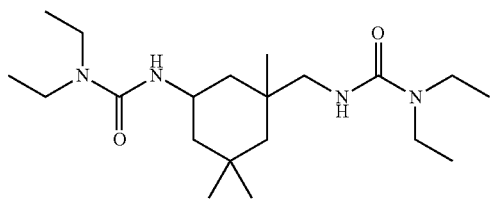
101-22
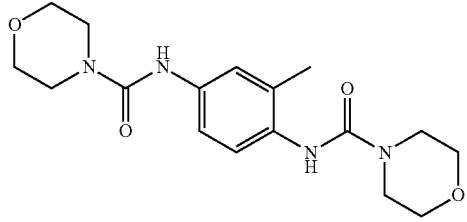
101-23
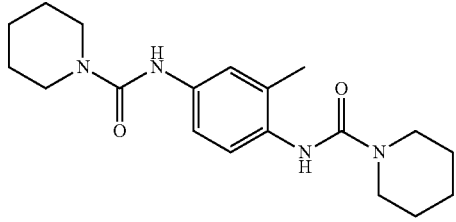
101-24
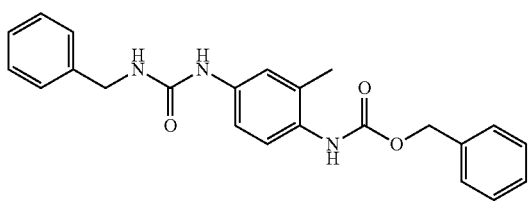
101-25
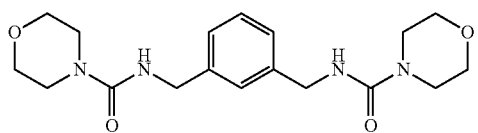
101-26
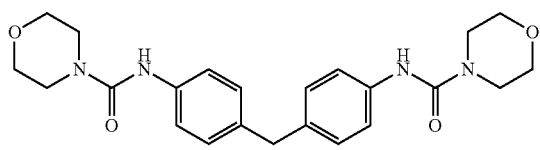
101-27
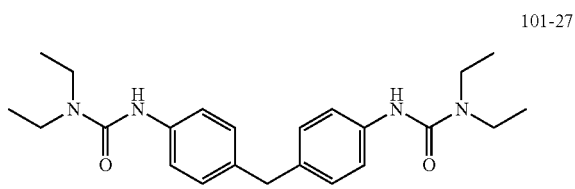
101-28
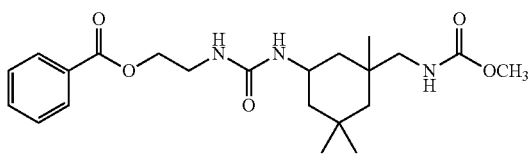
101-29
101-30
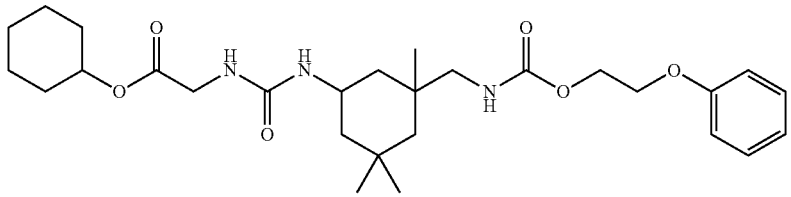
102-1
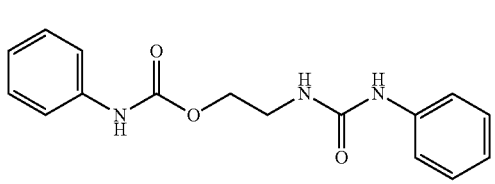
102-2
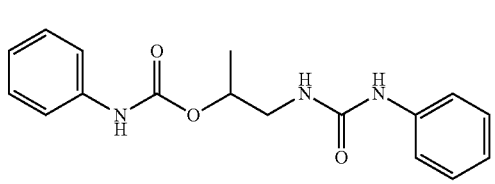
102-3
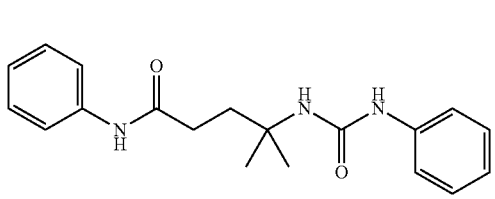
102-4
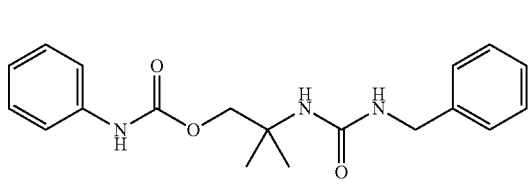

-continued
102-5
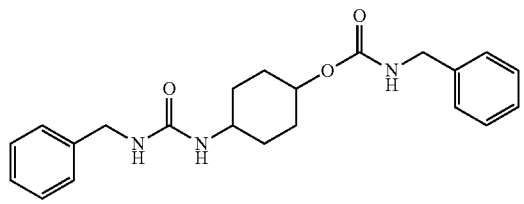
102-6
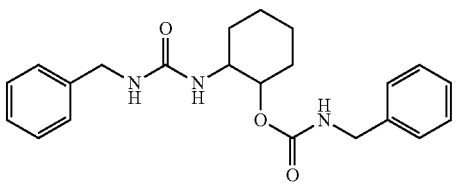
102-7
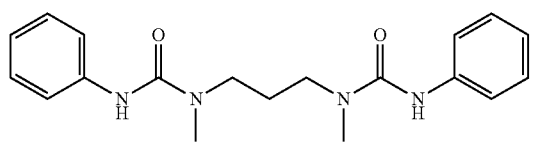
103-1
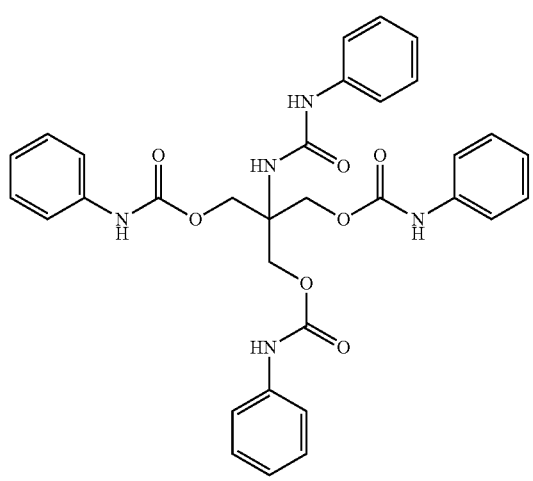
103-2
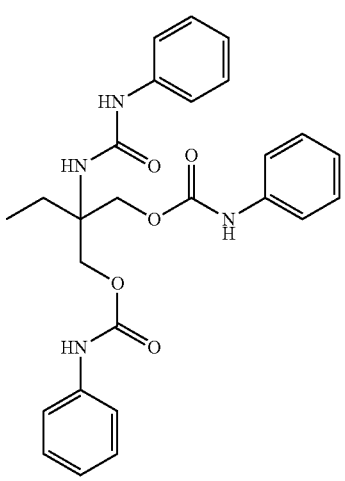
103-3
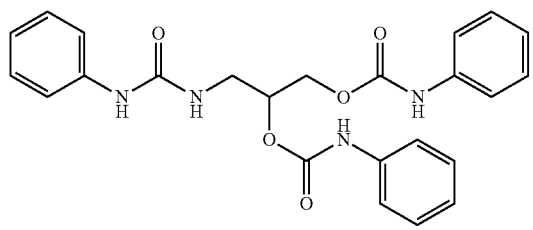
104-1
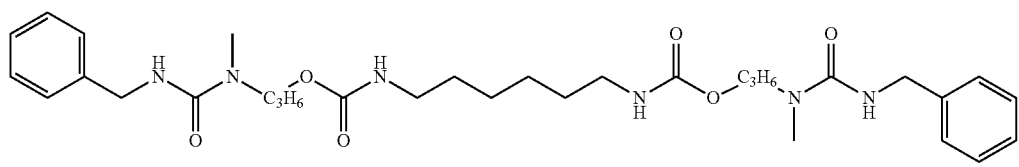
104-2
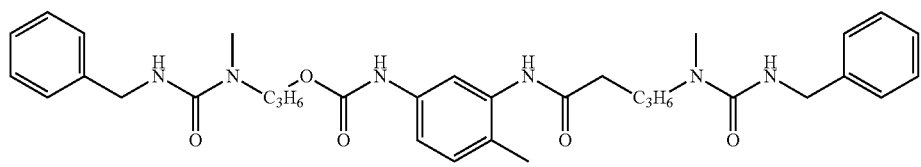
104-3
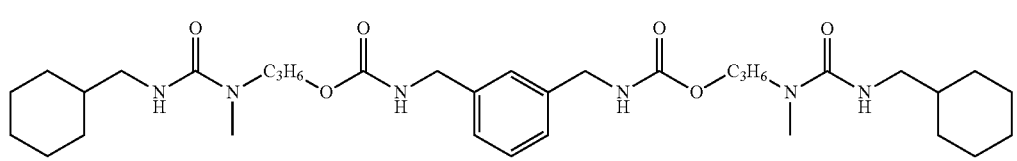

-continued
104-4
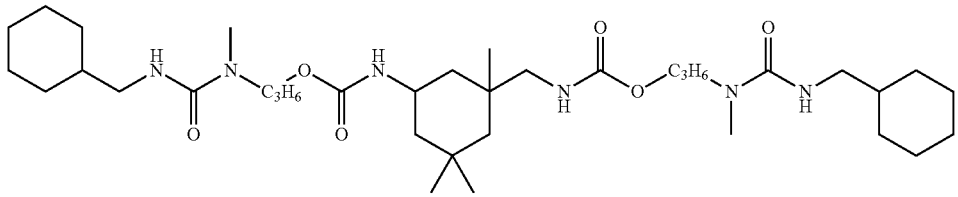
104-5
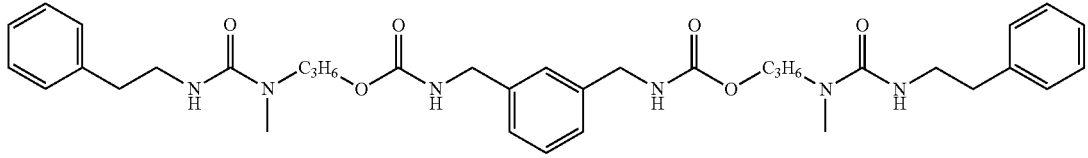
104-6
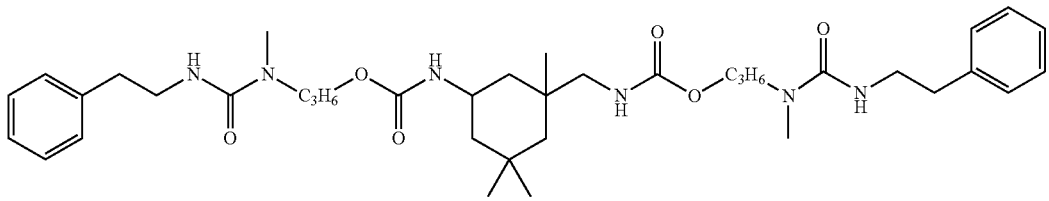
104-7
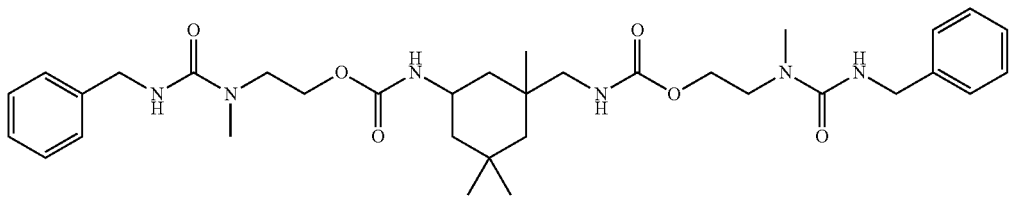
104-8
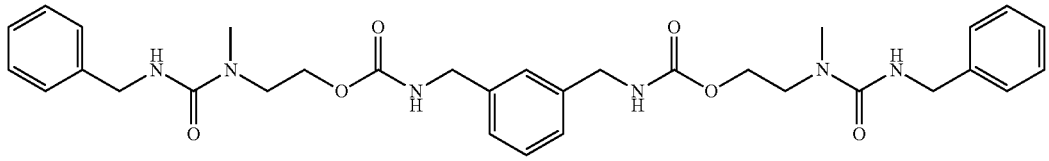
104-9
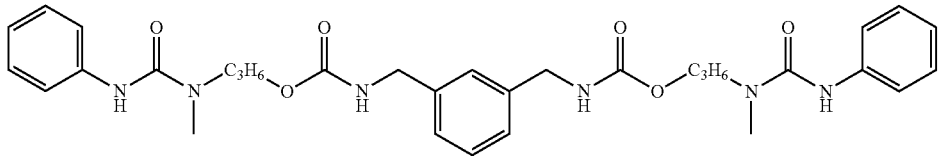
104-10
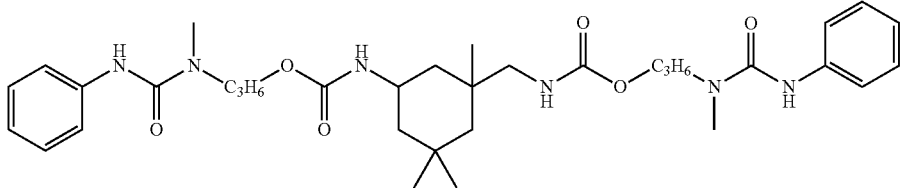
104-11
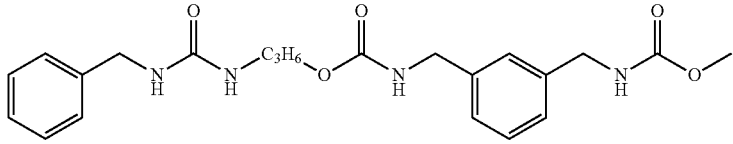

104-12 (mixture)
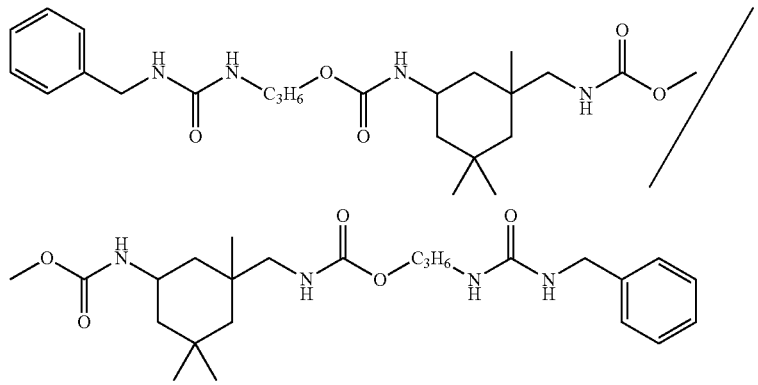
104-13
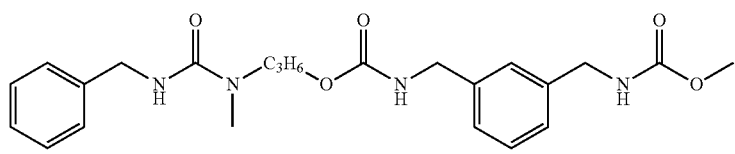
104-14 (mixture)
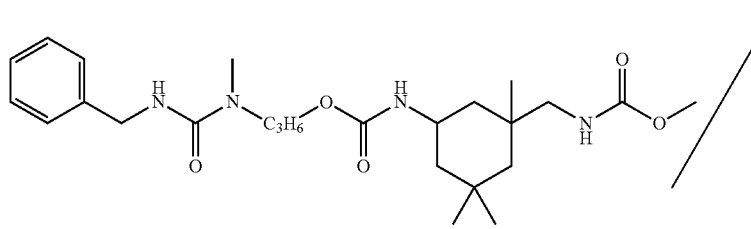
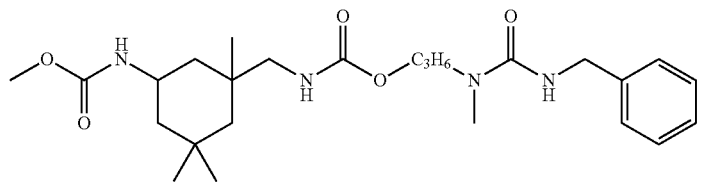
104-15
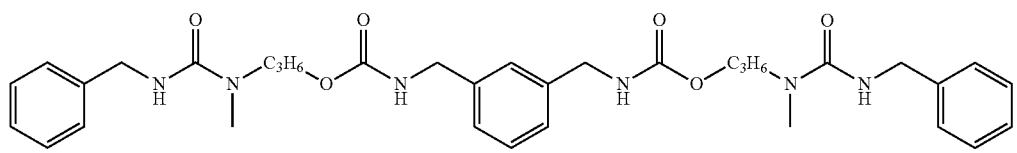
104-16
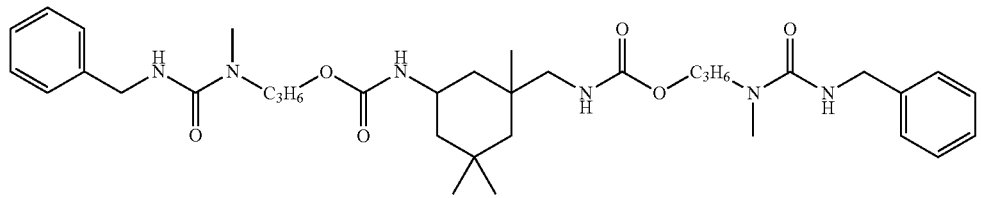
104-17
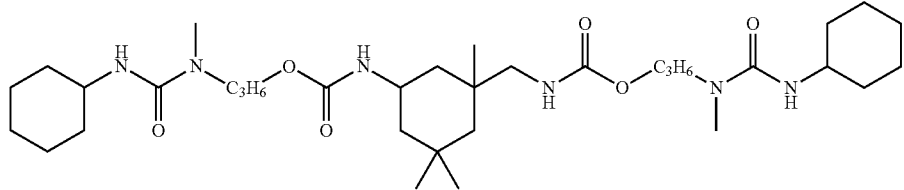

104-18
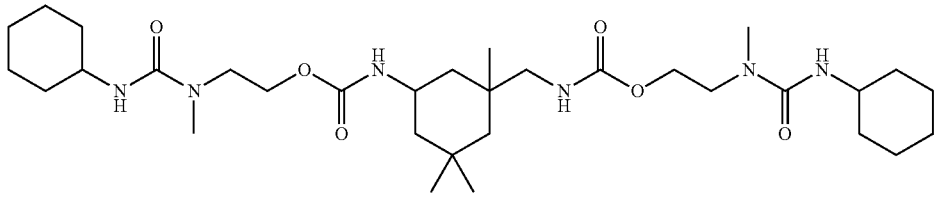
104-19
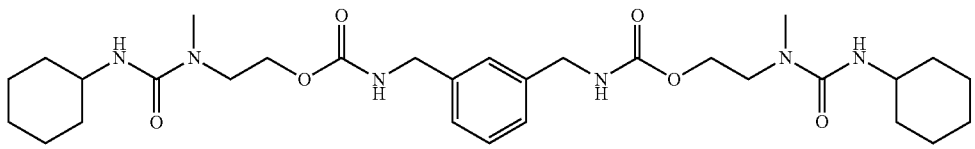
104-20
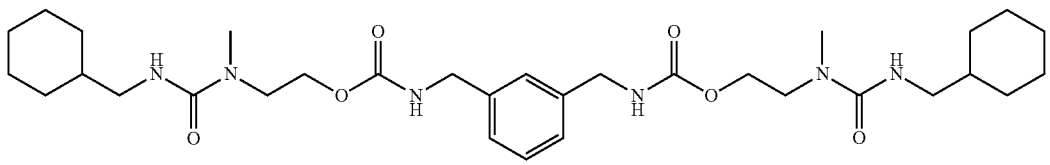
104-21
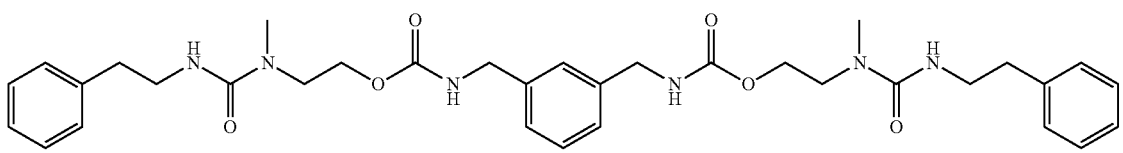
104-22
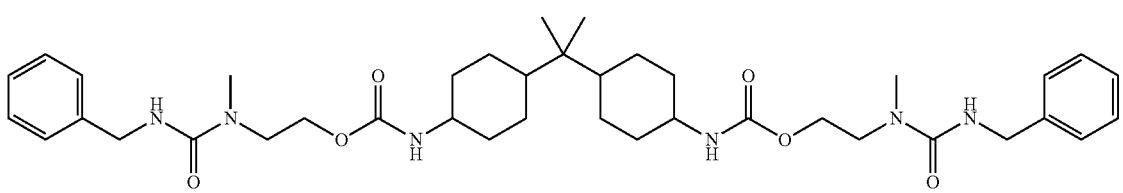
104-23
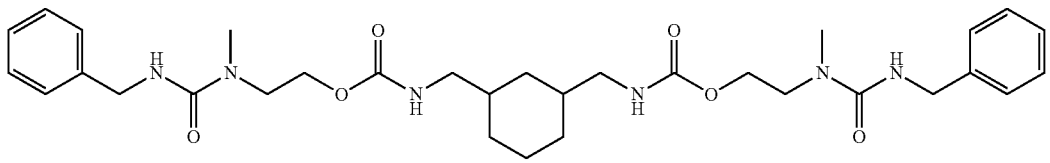
104-24
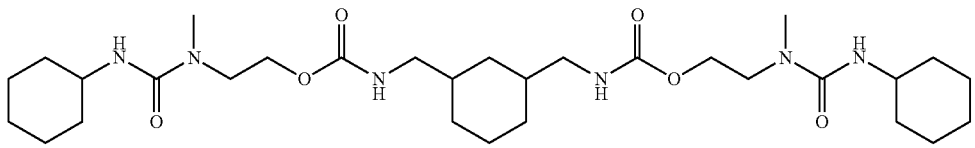
104-25
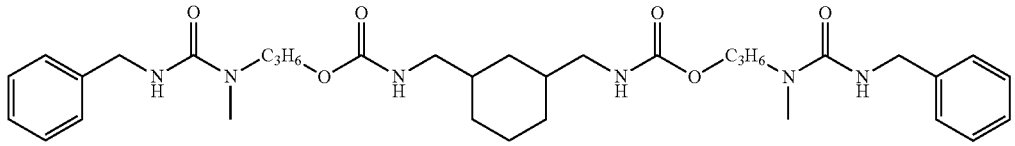
104-26
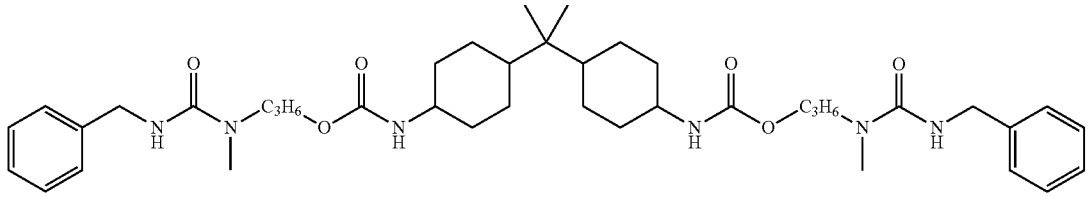

104-27
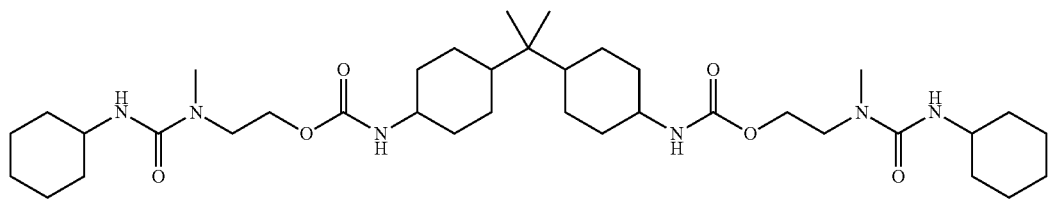
104-28
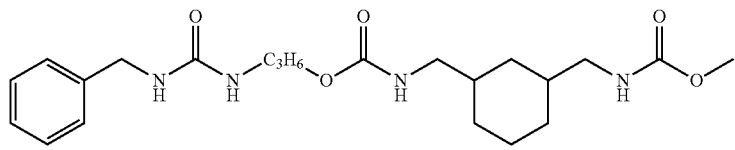
104-29
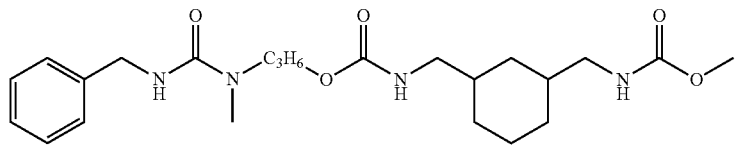
104-30
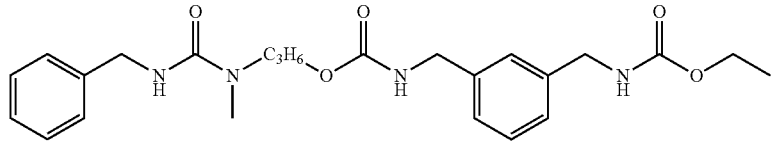
104-31
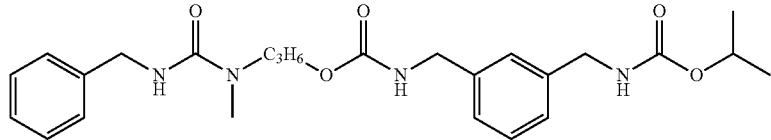
104-32
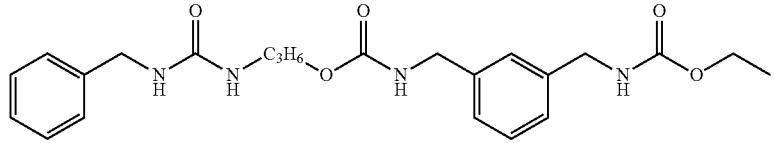
104-33
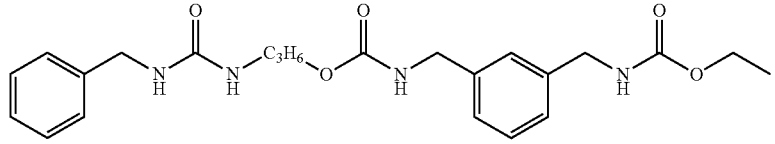
104-34
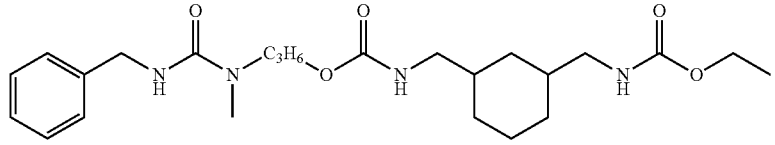
104-35
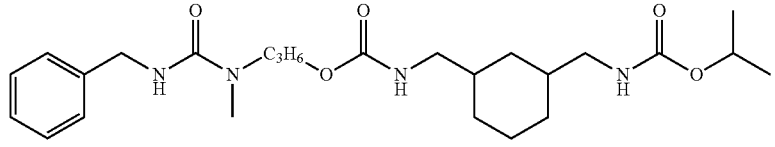
104-36
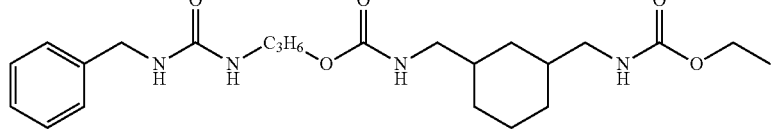

-continued
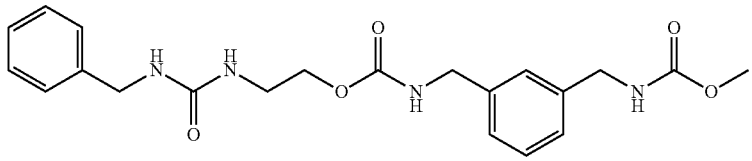
104-37
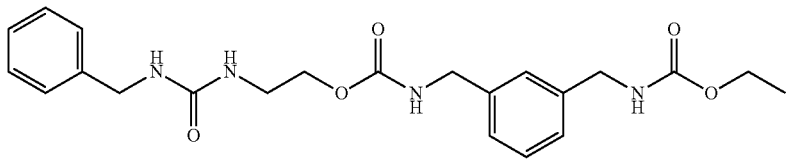
104-38
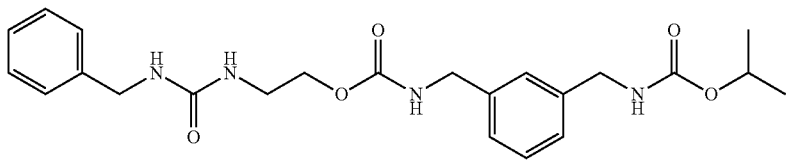
104-39
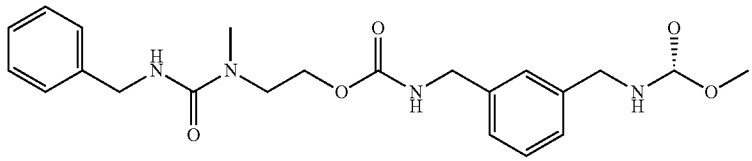
104-40
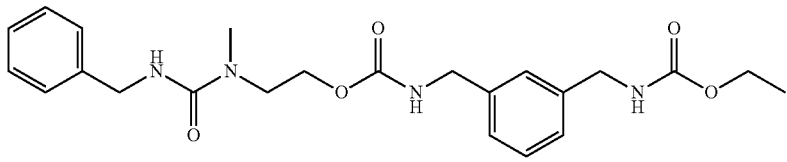
104-41
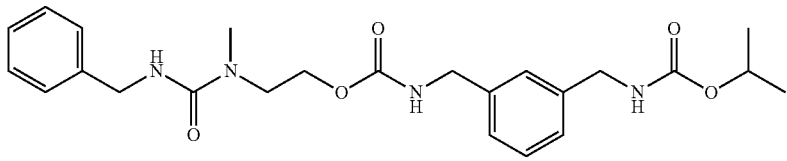
104-42
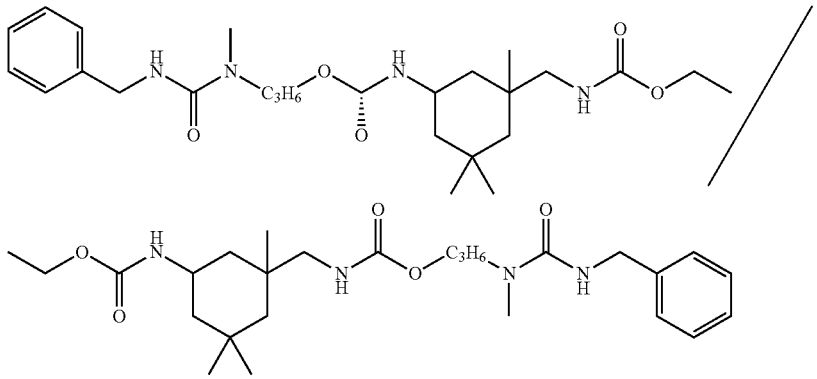
104-43 (mixture)
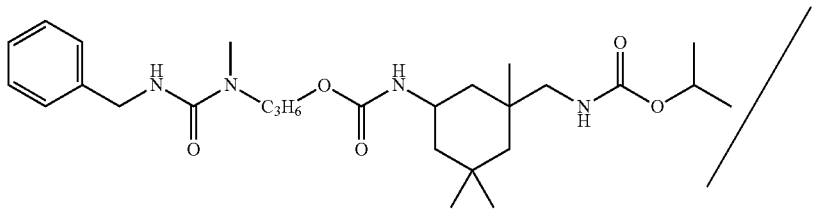
104-44 (mixture)

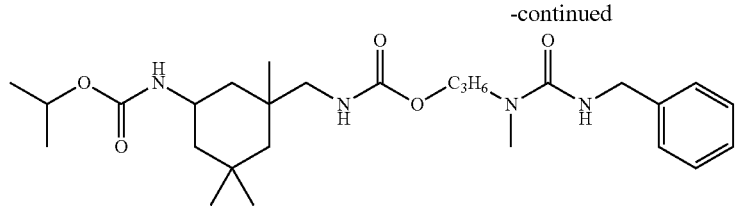
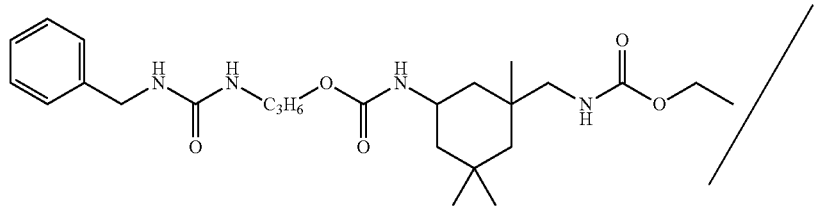
104-45 (mixture)
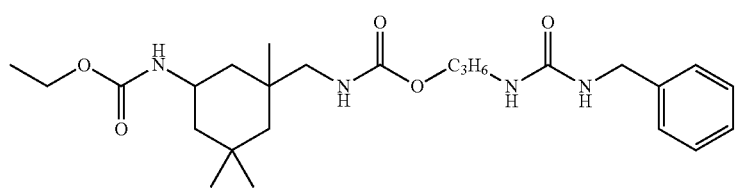
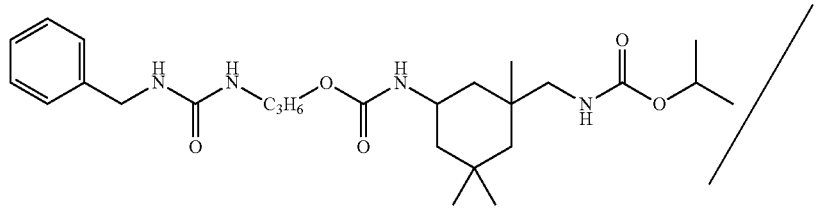
104-46 (mixture)
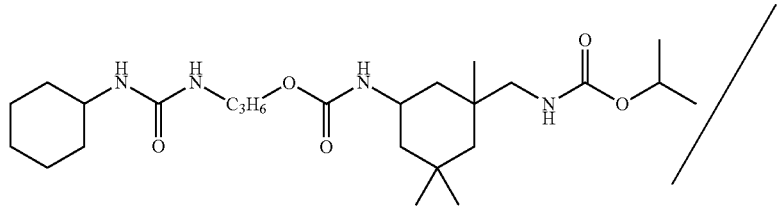
104-47 (mixture)
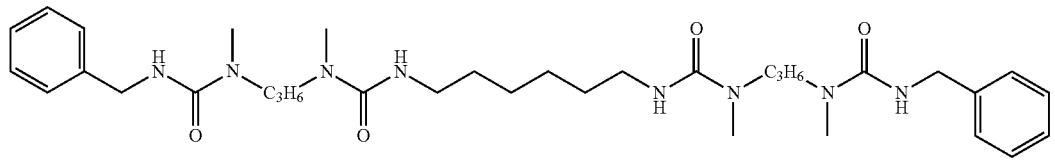
105-1

105-2
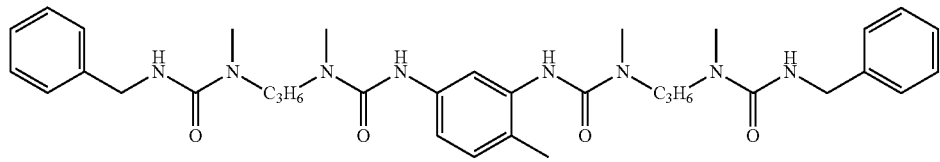
105-3
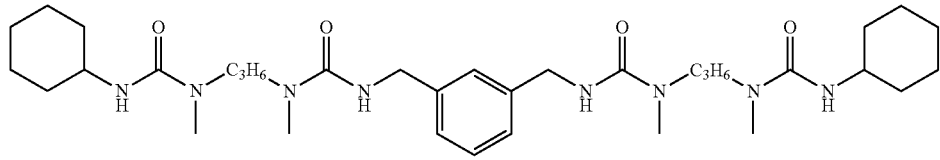
105-4
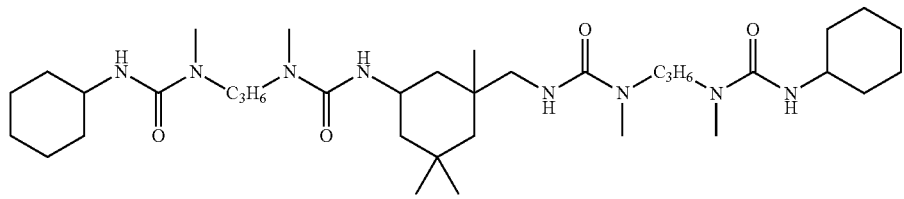
105-5
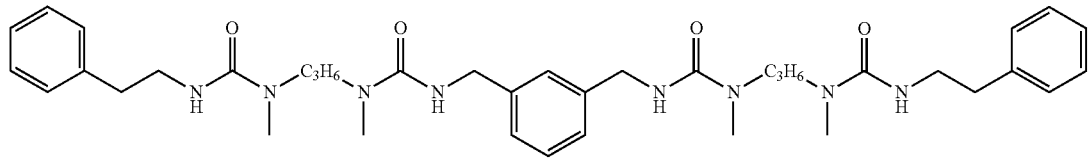
105-6
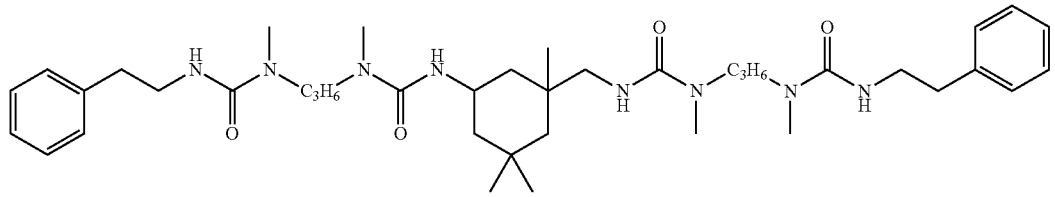
105-7
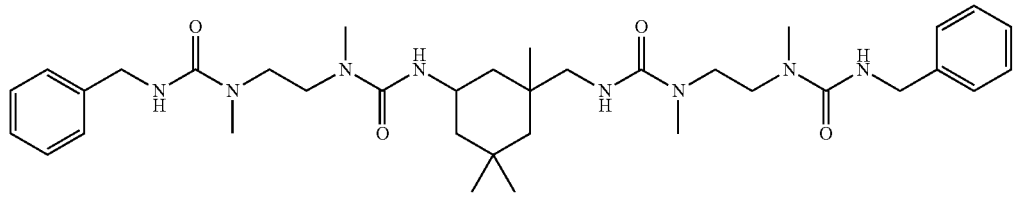
105-8
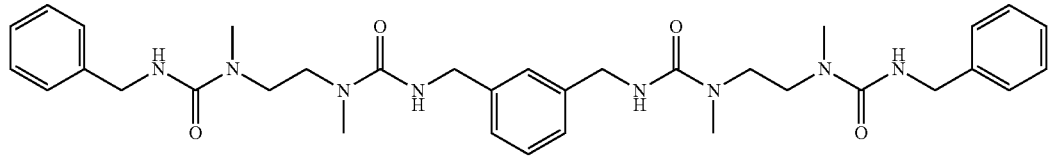
105-9
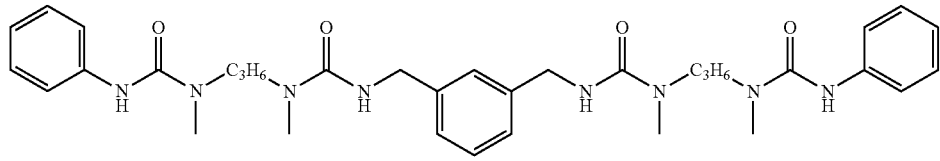

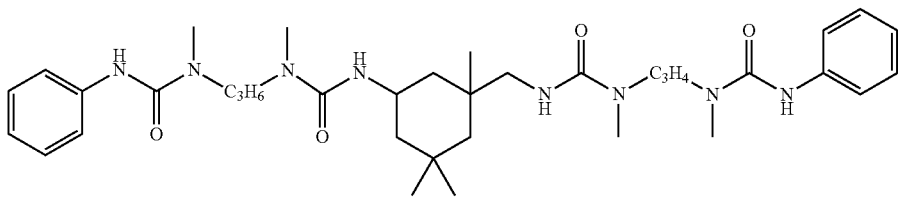
105-10
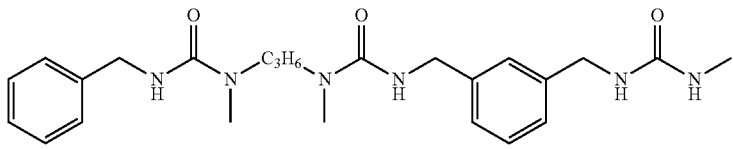
105-11
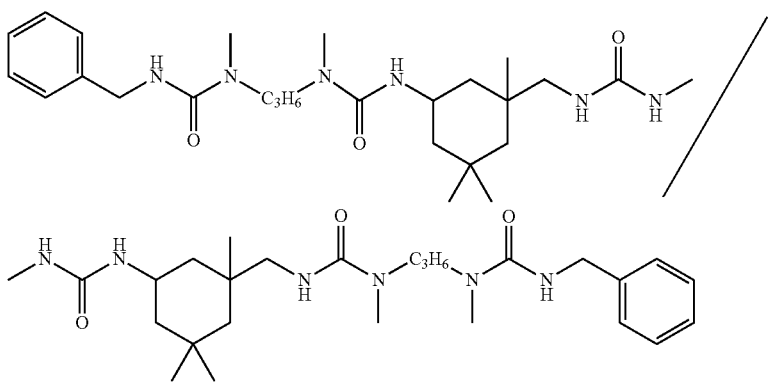
105-12 (mixture)
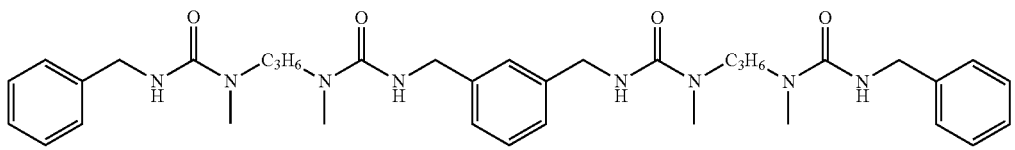
105-13
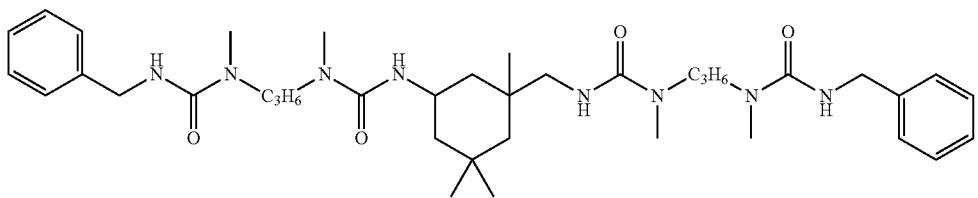
105-14
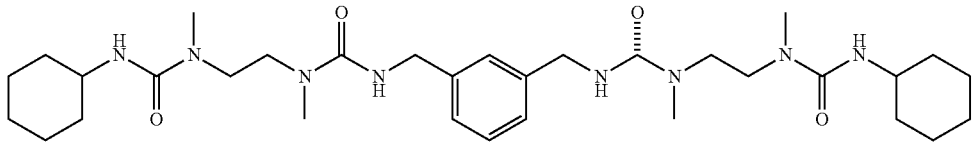
105-15
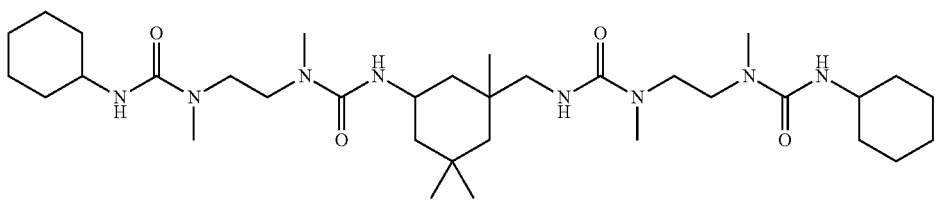
105-16
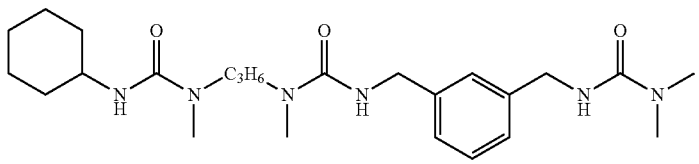
105-17

105-18
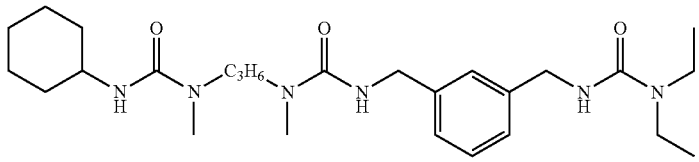
105-19
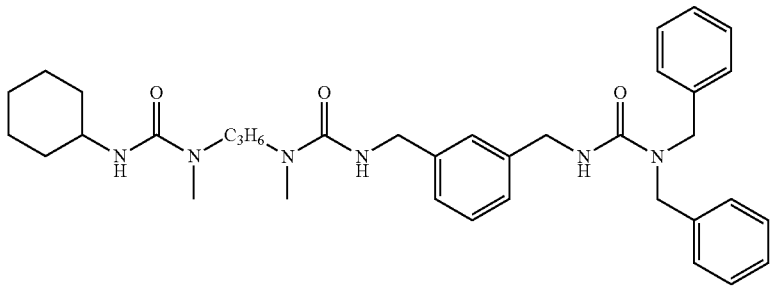
105-20
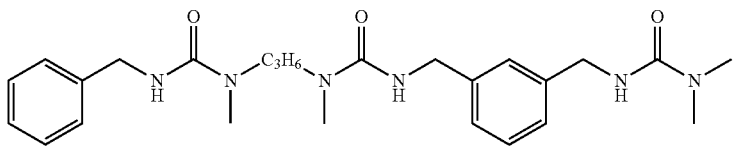
105-21
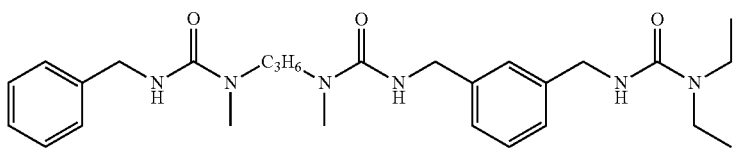
105-22
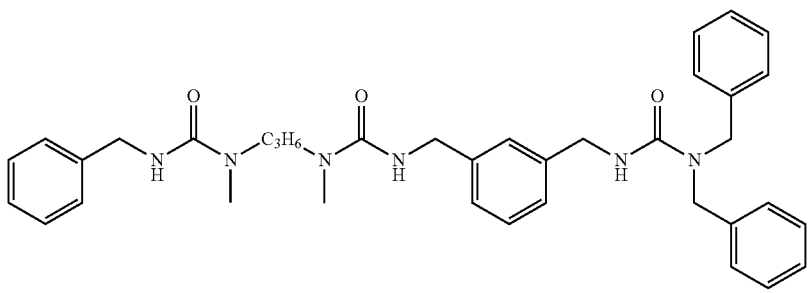
105-23 (mixture)
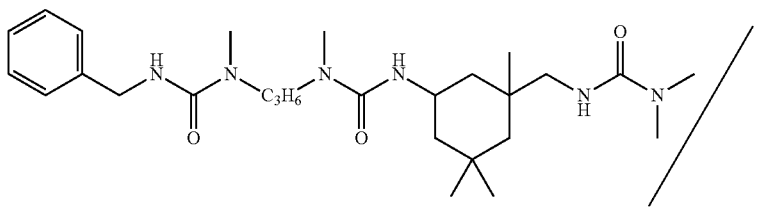
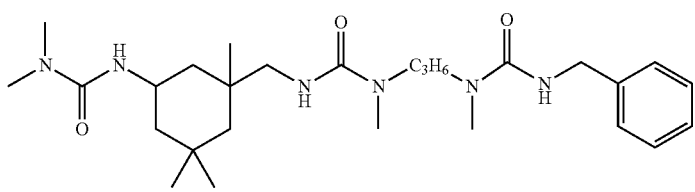

-continued

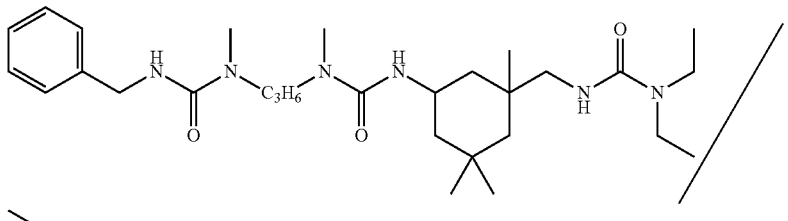

105-24 (mixture)

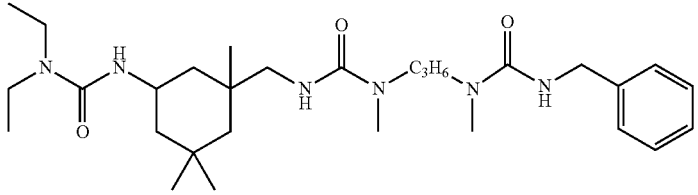

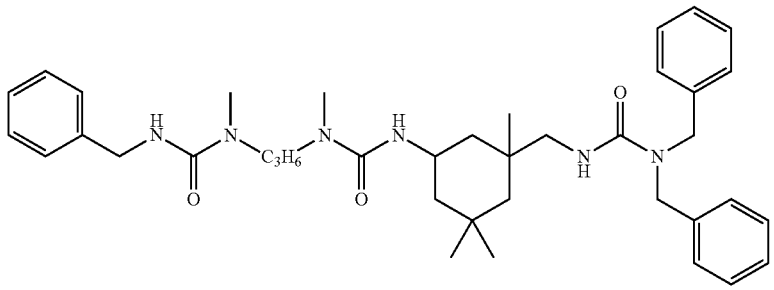

105-25 (mixture)

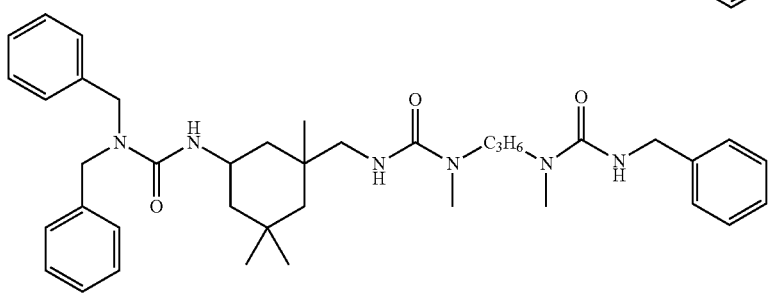

The above compounds can be synthesized by publicly-known methods.

For example, they can be obtained by reactions that add amines to alkyl or aryl isocyanates.

In the process of a reaction adding an amine to an alkyl or aryl isocyanate, it is preferable to employ a catalyst. Amines, metal organic acid salts or metal chelate compounds of zinc, tin and the like; organic metal compounds of zinc, tin, bismuth and the like, or some other conventionally known urethane catalyst can be employed as the catalyst. Examples of urethane catalysts that are preferably employed are dibutyltin dilaurate and dibutyltin diacetate.

When a component for introducing a divalent linking group denoted by —NH—(C=O)—O— and a component for introducing a divalent linking groups denoted by —NH—(C=O)—NR— are employed in combination when synthesizing the above compound, a compound having a structure comprising one or more instances of just the divalent linking group denoted by —NH—(C=O)—NR— among the two types of linking groups and a compound having a structure comprising one or more of each of the two will sometimes be obtained. A mixture of compounds with differing numbers of the above linking groups that are introduced will also sometimes be obtained. In the present invention, it is possible to use a mixture of the various compounds set forth above to manufacture a cellulose acylate film. It is also possible to use a known method to purify a compound of targeted structure from the mixture and employ it as a single product.

Either a combination of a polyvalent isocyanate (diisocyanate, triisocyanate, or the like) and a monovalent amine or a combination of a polyvalent amine and a monovalent isocyanate is preferably employed as the compound denoted by general formula (A-100).

Examples of polyvalent isocyanate components and examples of monovalent isocyanate components are as set forth above for the compound denoted by general formula (I).

Examples of polyvalent amines are ethylene diamine, xylylene diamine, and 4,4'-diaminodiphenylmethane.

Examples of monovalent amines are substituted and unsubstituted amines, such as methylamine, dimethylamine, diethylamine, aniline, benzylamine, cyclohexylamine, morpholine, and piperidine.

Aminoalcohols can also be employed. Examples are 2-aminoethanol and 1-amino-2-propanol.

The molecular weight of the compound denoted by general formula (A-100) preferably falls within a range of 230 to 2,000, more preferably falls within a range of 250 to 1,500, yet more preferably falls within a range of 300 to 1,000, and most preferably, falls within a range of 350 to 800.

When the molecular weight is greater than or equal to 230, there is good inhibition of volatilization from the film. A molecular weight that is less than or equal to 2,000 is preferable in that there is sufficient compatibility with the cellulose acylate and increased haze can be prevented.

The degree to which the compound denoted by general formula (A-100) is hydrophilic can be denoted as a Log P value. The P in Log P denotes the distribution coefficient in an n-octanol-aqueous system and can be measured using n-octanol and water. However, these distribution coefficients can also be calculated as an estimated c Log P value using a c log P value estimating program (C LOG P program included in PC Models of Daylight Chemical Information Systems Corp.). A C log P of −1.0 to 12.0 is preferable, 1.0 to 10.0 is more preferable, and 2.0 to 8.0 is most preferable.

Further, the melting point of the compound denoted by general formula (A-100) is preferably −50 to 250° C., more preferably −30 to 200° C. By remaining within such ranges, the effect of the present invention tends to be more effectively realized.

The method of measuring the melting point is as set forth above.

(Cellulose Acylate)

The degree of substitution of cellulose acylate means the ratio of acylation of the three hydroxyl groups present on the structural unit ((β) 1,4-glycoside-bonded glucose) of cellulose. The degree of substitution (acylation degree) can calculated by measuring the amount of bonded fatty acid per structural unit mass of cellulose. In the present invention, the degree of substitution of the cellulose material can be determined by dissolving the cellulose material in a solvent such as dimethylsulfoxide that has been substituted with heavy hydrogen, conducting $^{13}$C-NMR spectral measurement, and calculating the degree of substitution from the peak intensity ratio of the carbonyl carbon in the acyl groups. Once the residual hydroxyl groups of cellulose acylate have been replaced with acyl groups different from the acyl groups that are present in the cellulose acylate itself, determination is possible by $^{13}$C-NMR measurement. A detailed description of the measurement method is given by Tezuka et al. (Carbohydrate Res., 273 (1995) 83-91).

The substitution degree of the cellulose acylate employed in the present invention is preferably greater than or equal to 1.5 and less than or equal to 3.0, more preferably 2.00 to 2.97, yet more preferably greater than or equal to 2.50 but less than 2.97, and most preferably, 2.70 to 2.95.

In cellulose acylate employing just acetyl groups as the acyl groups of cellulose acylate, from the perspective of achieving major improvement in the degree of surface hardness of the film due to the compound denoted by general formula (I), the degree of substitution is preferably greater than or equal to 2.0 and less than or equal to 3.0, more preferably 2.3 to 3.0, yet more preferably 2.60 to 3.0, much more preferably 2.6 to 2.97, and most preferably, 2.70 to 2.95.

Acetyl groups, propionyl groups, and butyryl groups are preferred, and acetyl groups are of greater preference as the acyl groups in cellulose acylate that can be employed in the present invention.

Mixed fatty acid esters comprising two or more types of acyl groups are also preferably employed as the cellulose acylate in the present invention. In this case, acetyl groups and acyl groups having 3 or 4 carbon atoms are preferably as the acyl groups. When employing mixed fatty acid esters, the degree of substitution when acyl groups are contained in the form of acetyl groups is preferably less than 2.5 and more preferably less than 1.9. The degree of substitution when acyl groups having 3 or 4 carbon atoms are contained is preferably 0.1 to 1.5, more preferably 0.2 to 1.2, and most preferably, 0.5 to 1.1.

In the present invention, two different types of cellulose acylate with different substituents and/or different degrees of substitution can be combined and mixed for use, and the co-casting method, described further below, or the like can be used to form a film comprised of multiple layers of different types of cellulose acylate.

The mixed acid esters comprising substituted or unsubstituted aromatic acyl groups and fatty acid acyl groups described in JP-A-No. 2008-20896, paragraphs 0023 to 0038, is also preferably employed in the present invention.

The cellulose acylate employed in the present invention preferably has an average degree of polymerization of 250 to 800, more preferably an average degree of polymerization of 300 to 600. The cellulose acylate that is employed in the present invention preferably has a weight average molecular weight of 40,000 to 230,000, more preferably a weight average molecular weight of 60,000 to 230,000, and most preferably, a weight average molecular weight of 75,000 to 200,000.

The cellulose acylate employed in the present invention can be synthesized using an acid anhydride or an acid chloride as the acylating agent. When the acylating agent is an acid anhydride, an organic acid (such as acetic acid) or methylene chloride is employed as the reaction solvent. A protonic catalyst such as sulfuric acid can be employed as a catalyst. When the acylating agent is an acid chloride, a basic compound can be employed as a catalyst. The most common synthesis method industrially is to esterify the cellulose with mixed organic acid components in the form of organic acids (acetic acid, propionic acid, butyric acid) or their anhydrides (acetic anhydride, propionic anhydride, butyric anhydride) corresponding to the acetyl group and other acyl group to synthesize cellulose acylate.

In the above method, cellulose such as cotton linter or wood pulp is activation treated with an organic acid such as acetic acid. A mixed solution of organic acid components such as those set forth above is then often used to conduct esterification in the presence of a sulfuric acid catalyst. The organic acid anhydride component is generally used in an excess quantity relative to the quantity of hydroxyl groups present in the cellulose. In this esterification treatment, a hydrolysis reaction (depolymerization reaction) takes place on the cellulose main chain ((β) 1,4-glycoside bond) in addition to the esterification reaction. As hydrolysis of the main chain progresses, the degree of polymerization of the cellulose acylate decreases and the physical properties of the cellulose acylate film that is manufactured deteriorate. Thus, reaction conditions such as the reaction temperature are preferably determined by taking into account the molecular weight and degree of polymerization of the cellulose acylate that is to be obtained.

Quantities Added

The compound denoted by general formula (I) described in the first aspect and the compound denoted by general formula (A-100) described in the second aspect can be used singly, or in combinations of any two or more differing compounds. When these compounds are employed in combination, the ratio of the compound denoted by general formula (I) and the compound denoted by general formula (A-100) is preferably from 25/75 to 75/25 as the weight ratio (compound denoted by general formula (I)/general formula (A-100)). The quantities of these compounds that are added are not specifically limited. However, 0.1 to 50 mass parts are preferable, 0.5 to 30 mass parts are more preferable, 1 to 20 mass parts are yet more preferable, and 2 to 15 mass parts per 100 mass parts of cellulose acylate are most preferable. In embodiments in which two or more compounds are employed in combination, the above quantities added refer to the combined quantity of the multiple compounds.

In addition to the cellulose acylate and the one or more compounds set forth above, other additives can be contained in the cellulose acylate film of the present invention. Examples of these additives are known plasticizers, organic acids, pigments, polymers, retardation regulators, ultraviolet radiation absorbing agents, oxidation inhibitors, and matting agents. For a description of these additives, JP-A-No. 2012-155287, paragraphs 0062 to 0097, can be referred, the entire contents of which are hereby incorporated by reference. The total blended quantity of these additives is preferably less than or equal to 50 mass %, more preferably less than or equal to 30 mass %, of the cellulose acylate.

<Method of Manufacturing the Cellulose Acylate Film>

The method of manufacturing the cellulose acylate film of the present invention is not specifically limited. The manufacturing is preferably done by the melt film-forming method or solvent casting method, and more preferably done by the solvent casting method. For examples of manufacturing cellulose acylate films by the solvent casting method, each specification of U.S. Pat. Nos. 2,336,310, 2,367,603, 2,492,078, 2,492,977, 2,492,978, 2,607,704, 2,739,069, and 2,739,070; UK patents 640,731 and 736,892; Japanese Examined Patent Publication (KOKOKU) Showa Nos. 45-4554 and 49-5614; JP-A-Nos. Showa 60-176834, 60-203430, and 62-115035, can be referred. Cellulose acylate films can also be subjected to stretching treatment. JP-A-Showa No. Showa 62-115035 and Heisei Nos. 4-152125, 4-284211, 4-298310, 11-48271, and the like, can be referred.

(Casting Methods)

Solution casting methods exist in the form of the method of uniformly extruding a prepared dope onto a metal support member through a pressure die; the method based on a doctor blade consisting of adjusting the film thickness of a dope that has been cast onto a metal support member with a blade; the method based on a reverse roll coater of adjustment with a roll rotating in reverse; and the like. The method based in a pressure die is preferred. Examples of a pressure die include a coat hanger type and a T-die type. Any of them is preferably employed. In addition to the examples of methods given here, various conventionally known methods of casting films with cellulose acylate solutions can be applied. The various conditions can be set by taking into account differences in the boiling point and the like of the solvent employed.

Co-Casting

Accumulation flow casting methods such as the co-casting method, sequential casting method, and coating method are preferably employed to form cellulose acylate films. Use of the simultaneous co-casting method is particularly preferable from the perspective of stable manufacturing and reduced production costs.

In manufacturing by the co-casting and sequential casting methods, a cellulose acylate solution (dope) is first prepared for each layer. The co-casting method (simultaneous lamination casting) is a casting method in which the casting dopes of the individual layers (three layers, or even more) are simultaneously extruded through separate slits with a casting gisa to simultaneously cast all the layers on a casting support (band or drum). At a suitable time, the film is separated from the support and dried to mold a film. Using a co-casting gisa, it is possible to simultaneously extrude and cast the three layers of outer layer dopes and a core layer dope on a casting support.

The sequential casting method is a casting method in which a first layer casting dope is first extruded and cast through a casting gisa onto a casting support and, with or without drying, the second layer casting dope is extruded and cast with the casting gisa over the first layer. The dopes of the third, and subsequent layers are sequentially cast and laminated by this procedure as needed. At a suitable time, the film is separated from the support and dried to form a cellulose acylate film. The coating method is a method generally in which a core layer film is formed into a film form by a solution film-forming method, the coating liquid that will be coated on the outer layer is prepared, and a suitable coating apparatus is employed to coat and dry the coating liquid on each of, or simultaneously on both of surfaces of the core layer, thereby molding a cellulose acylate film of laminate structure.

A cellulose acylate film of high surface hardness can be obtained by incorporating the above compounds into any one or more of these layers, or all of the layers.

(Stretch Processing)

A step of stretching the film is preferably included in the method of manufacturing the cellulose acylate film. The direction in which the cellulose acylate film is stretched is preferably either the direction of conveyance of the cellulose acylate film (MD direction) or the direction perpendicular to the direction of conveyance (TD direction). Making it the direction perpendicular to the direction of conveyance of the cellulose acylate film (TD direction) is preferred from the perspective of subsequent polarizing plate processing using the cellulose acylate film.

TD direction stretching methods are described in, for example, the publications of JP-A-Showa No. 62-115035 and Heisei Nos. 4-152125, 4-284211, 4-298310, and 11-48271. When conducting stretching in the MD direction, for example, the speed of the conveyor rollers of the cellulose acylate film is adjusted so that the winding rate of the cellulose acylate film is greater than the peeling rate of the cellulose acylate film, thereby stretching the cellulose acylate film. When conducting stretching in the TD direction, the cellulose acylate film is conveyed while holding the width with a tenter, and gradually widening the width of the tenter to stretch the cellulose acylate film. After drying the cellulose acylate film, stretching can be conducted with a stretching apparatus (preferably uniaxial stretching with a Long stretching apparatus).

When employing a cellulose acylate film as a protective film on a polarizer, to inhibit leakage of light when viewing the polarizing plate diagonally, it is necessary to dispose the transmission axis of the polarizer and the in-plane slow axis of the cellulose acylate film in parallel. Since the transmission axis of a polarizer in the form of a continuously manufactured roll film is generally parallel to the width direction of the roll film, the continuously adhesion of a protective film comprised of a cellulose acylate film in the form of a roll film on the polarizer in the form of a roll film requires that the in-plane slow axis of the protective film in the form of a roll film be parallel to the width direction of the cellulose acylate film. Accordingly, greater stretching is preferable in the TD direction. The stretch processing can be conducted during the film manufacturing process, or the film can be manufactured and the wound raw sheet can be stretch processed.

The stretching in the TD direction is preferably 5 to 100%, preferably 5 to 80%, and more preferably, 5 to 40%. The term "unstretched" means stretched by 0%. The stretch processing can be conducted during the film manufacturing process, or the film can be manufactured and the wound raw sheet can be stretch processed. In the former case, stretching can be conducted with a quantity of residual solvent present. Stretching is preferably conducted so that the quantity of residual solvent, which is equal to (mass of residual volatized fraction/mass of film after heat treatment)×100%, is 0.05 to 50%. It is preferable to conduct 5 to 80% stretching with the quantity of residual solvent being 0.05 to 5%.

Subjecting the cellulose acylate film containing the compound set forth above to stretch processing can further increase the surface hardness of the film.

<Physical Properties of the Cellulose Acylate Film>

Surface Hardness:

Incorporating the above compound into the cellulose acylate film of the present invention can impart high surface hardness. The surface hardness of the cellulose acylate film can be adjusted by adjusting the type or content of compound denoted by general formula (A). The Knoop hardness can be employed as an indicator of the surface hardness of the cellulose acylate film. The Knoop hardness is measured by the method indicated in Examples further below.

Modulus of Elasticity:

The cellulose acylate film exhibits a modulus of elasticity that is adequate in practical terms. The range of the modulus of elasticity is not specifically limited. From the perspective of suitability to manufacturing and handling properties, it is preferably 1.0 to 6.0 GPa, more preferably 2.0 to 5.0 GPa. Adding the above compound to the cellulose acylate film has the effect of increasing the modulus of elasticity by rendering the cellulose acylate film hydrophobic, which is another advantage afforded by the present invention.

Photo-Elastic Coefficient:

The absolute value of the photo-elastic coefficient of the cellulose acylate film is preferably less than or equal to $8.0 \times 10^{-12}$ $m^2/N$, more preferably less than or equal to $6.0 \times 10^{-12}$ $m^2/N$, and more preferably, less than or equal to $5 \times 10^{-12}$ $m^2/N$. Keeping the photo-elastic coefficient of the cellulose acylate film low can inhibit the generation of nonuniformity at high temperature and high humidity when the cellulose acylate film of the present invention is incorporated into a liquid crystal display device as a protective film on a polarizing plate. The photo-elastic coefficient is calculated by the following measurement method unless specifically stated otherwise.

The lower limit of the photo-elastic coefficient is not specifically limited, but is greater than or equal to $0.1 \times 10^{-12}$ $m^2/N$ in practical terms.

The photo-elastic coefficient is obtained by cutting cellulose acylate into 3.5 cm×12 cm pieces; measuring the Re at loads of zero, 250 g, 500 g, 1000 g, and 1,500 g with a ellipsometer (M150, JASCO (Ltd.)); and calculating the photo-elastic coefficient from the slope of the line of the change in Re relative to stress.

Water Content:

The water content of the cellulose acylate film can be evaluated by measuring the equilibrium water content at a certain temperature and humidity. The equilibrium water content is determined by placing the sample for 24 hours at the above temperature and humidity, measuring the quantity of water in the sample that has reached equilibrium by the Karl Fischer method, and dividing the quantity of water (g) by the mass of the sample (g).

The water content of the cellulose acylate film at 25° C. and 80% relative humidity is preferably less than or equal to 5 mass %, more preferably less than or equal to 4 mass %, and most preferably, less than 3 mass %. Keeping the water content of the cellulose acylate film low can cause display nonuniformity not to occur in liquid crystal display devices at high temperature and high humidity when the cellulose acylate film of the present invention is incorporated as a protective film on a polarizing plate in a liquid crystal display device. The lower limit of the water content is not specifically defined, but is greater than or equal to 0.1 mass % in practical terms.

Moisture Permeability:

The moisture permeability of the cellulose acylate film can be evaluated by measuring the mass of water vapor passing through a sample during 24 hours in an atmosphere with a temperature of 40° C. and a relative humidity of 90% RH according to the JIS Z0208 Moisture Permeability Test (Cup method) and converting it to a value per $m^2$ of sample area.

The moisture permeability of the cellulose acylate film is preferably 500 to 2,000 $g/m^2 \cdot day$, more preferably 900 to 1,300 $g/m^2 \cdot day$, and most preferably, 1,000 to 1,200 $g/m^2 \cdot day$.

Haze:

The cellulose acylate film preferably has haze of less than or equal to 1%, more preferably less than or equal to 0.7%, and most preferably, less than or equal to 0.5%. Keeping the haze to less than the upper limit set forth above affords the advantages of increasing the transparency of the cellulose acylate film and rendering it easier to use as an optical film. Unless specifically stated otherwise, the haze is calculated based on measurement by the following method. The lower limit of haze is not specifically limited, but is greater than or equal to 0.001% in practical terms.

The haze is measured for a 40 mm×80 mm sample of cellulose acylate film in accordance with JIS K7136 with a hazemeter (HGM-2DP, Suga Test Instruments) in an environment of 25° C. and 60% relative humidity.

Film Thickness:

The average film thickness of the cellulose acylate film can be suitably determined based on the application. As an example, it is 20 to 100 μm. The average film thickness of the cellulose acylate film is preferably 10 to 100 μm, more preferably 15 to 80 μm, and most preferably, 20 to 70 μm. Keeping it to greater than or equal to 20 μm is preferable to enhance handling properties when fabricating a web-like film. Keeping it to less than or equal to 70 μm tends to facilitate response to changes in humidity and maintain optical characteristics.

When the cellulose acylate film has a laminate structure with three or more layers, the thickness of the core layer is preferably 3 to 70 μm, more preferably 5 to 60 μm. The thickness of each of skin layer A and skin layer B is preferably 0.5 to 20 μm, more preferably 0.5 to 10 μm, and optimally, 0.5 to 3 μm. The core layer refers to the middle portion in a three-layer structure, and the skin layers refer to the outermost layers in a three-layer structure.

Width:

The width of the cellulose acetylate film is preferably 700 to 3,000 mm, more preferably 1,000 to 2,800 mm, and most preferably, 1,300 to 2,500 mm.

(Saponification)

The above cellulose acylate film can be subjected to an alkali saponification treatment to impart adhesion to the material of a polarizer such as polyvinyl alcohol, permitting use as the protective film of a polarizing plate.

The method described in JP-A-No. 2007-86748, paragraphs 0211 and 0212, can be employed as the saponification method.

For example, the alkali saponification treatment of the cellulose acylate film is preferably conducted in a cycle of immersing the film surface in an alkali solution followed by neutralization with an acidic solution, washing with water, and drying. Examples of the alkali solution are a potassium hydroxide solution and sodium hydroxide solution. The concentration of the hydroxide ions preferably falls within a range of 0.1 to 5.0 mol/L, more preferably within a range of 0.5 to 4.0 mol/L. The temperature of the alkali solution preferably falls within a range of room temperature to 90° C., more preferably within a range of 40 to 70° C.

Adhesion-enhancing processing such as is described in JP-A-Heisei Nos. 6-94915 and 6-118232 can be conducted instead of an alkali saponification treatment.

[Polarizing Plate]

The polarizing plate of the present invention comprises the above cellulose acylate film and a polarizer.

In one embodiment, the cellulose acylate film of the present invention is present on the polarizing plate as a protective film. The polarizing plate according to this embodiment comprises a polarizer and two polarizing plate protection films (transparent films) that protect the two surfaces thereof, and comprises the cellulose acylate film of the present invention as at least one of the polarizing plate protection films thereof.

The cellulose acylate film of the present invention is preferably employed as the protective film on the viewer-side of upper polarizing plate 10. In FIG. 1, which is a schematic view of an embodiment of the positional relation between the polarizing plate of the present invention and a liquid crystal display device, 1 denotes the cellulose acylate film of the present invention, 2 denotes the polarizer, 3 denotes a phase-difference film, and 4 denotes a liquid crystal cell. The upper side of FIG. 1 is the viewer-side.

As shown in FIG. 1, phase-difference film 3 is preferably employed as the polarizing plate protective film on the side on which the cellulose acylate film of the present invention is not employed. Examples of the phase-difference film are films obtained by blending various additives into the cellulose acylate film and stretching it to obtain a phase-difference film exhibiting the desired phase-difference and a phase-difference film comprising an optically anisotropic layer comprised of a liquid crystal composition on a support surface. Specifically, the description given in JP-A-No. 2008-262161 can be referred, the entire contents of which are hereby incorporated by reference.

For example, a polyvinyl alcohol film that has been immersed in an iodine solution and stretched can be employed as a polarizer. When employing a polarizer obtained by immersing a polyvinyl alcohol film in an iodine solution and stretching it, the surface-treated side of the cellulose acylate film of the present invention can be directly bonded to at least one side of the polarizer with adhesive. The adhesive employed can be an aqueous solution of a polyvinyl alcohol or polyvinyl acetal (such as polyvinyl butyral), or the latex of a vinyl polymer (such as polybutyl acrylate). The aqueous solution of a fully saponified polyvinyl alcohol is a preferred adhesive.

The polarizing plate protective film in the present invention is preferably bonded to the polarizer in such a manner that the transmission axis of the polarizer is essentially parallel to the slow axis of the polarizing plate protective film. The slow axis can be measured by various known measurement methods. For example, it can be measured with a birefringence meter (KOBRA DH, made by Oji Scientific Instruments (Ltd.)).

Here, the term "essentially parallel" means that the misalignment between the direction of the main refractive index nx of the polarizing plate protective film and the direction of the transmission axis of the polarizing plate is less than or equal to 50. This misalignment is preferably less than or equal to 10, more preferably less than or equal to 0.5°. A misalignment of less than or equal to 1° is preferable in that light leakage tends not to occur and the degree of polarization performance of the polarizing plate in crossed-nicols tends not to decrease.

<Functionalization of Polarizing Plate>

To the extent that no departure is made from the spirit of the present invention, the polarizing plate of the present invention is preferably employed as a functionalized polarizing plate which is combined with a view-enhancing antireflective film, brightness enhancement film, and/or an optical film having functional layer(s) such as a hard coat layer, forward-scattering layer, and antiglare layer. For details in this regard, the descriptions given in JP-A-No. 2012-082235, paragraphs 0229 to 0242, 0249, and 0250, and JP-A-No. 2012-215812, paragraphs 0086 to 0103, can be referred, the entire contents of which are hereby incorporated by reference.

<Hard Coat Layer>

The hard coat layer that is provided as desired on the cellulose acylate film is a layer for imparting hardness and scratch resistance to the polarizing plate of the present invention. For example, a coating composition can be coated on the cellulose acylate film to cure it, forming a hard coat layer on the cellulose acylate film. By adding fillers and additives to the hard coat layer, it is possible to impart physical properties such as mechanical, electrical, and optical properties, and chemical properties such as water and oil repellence, to the hard coat layer itself. The thickness of the hard coat layer preferably falls within a range of 0.1 to 6 μm, more preferably within a range of 3 to 6 μm. The presence of a thin hard coat layer falling within this range makes it possible to obtain a polarizing plate containing a hard coat layer with improved physical properties such as toughness, inhibiting of curling, reduced weight, and lowered production cost.

The hard coat layer is preferably formed by curing a curable composition. The curable composition is preferably prepared as a liquid coating composition. An example of the coating composition is one that contains a matrix-forming binder-use monomer, oligomer, or polymer and an organic solvent. By coating and then curing this coating composition, it is possible to form a hard coat layer. A cross-linking reaction or polymerization reaction can be used for curing. For details in this regard, the description in JP-A-No. 2012-215812, paragraphs 0088 to 0101, can be referred, the entire contents of which are hereby incorporated by reference.

A composition containing a (meth)acrylate compound, such as is employed in Examples further below, is a particularly suitable curable composition for forming the hard coat layer.

The curable composition is preferably prepared as a coating liquid. The coating liquid can be prepared by dissolving and/or dispersing the above components in an organic solvent.

(Properties of the Hard Coat Layer)

The hard coat layer that is formed on the cellulose acylate film is preferably highly adhesive to the cellulose acylate film. In the hard coat layer that is formed with a suitable curable composition on the cellulose acylate film containing the above compound, the curable composition can work in conjunction with the above compound to exhibit great adhesion to the cellulose acylate film. By comprising such a cellulose acylate film and hard coat layer, the polarizing plate of the present invention is capable of maintaining adhesion between the cellulose acylate film and the hard coat layer even if subjected to irradiation with light or the like, and thus can exhibit good light durability.

The hard coat layer preferably has good scratch resistance. Specifically, when conducting the pencil hardness test which serves as an indicator of scratch resistance, greater than or equal to 3 H is preferably achieved.

[Liquid Crystal Display Device]

The liquid crystal display device of the present invention is characterized by comprising at least one polarizing plate of the present invention. For details regarding liquid crystal display devices, JP-A-No. 2012-082235, paragraphs 0251 to 0260, can be referred, the entire contents of which are hereby incorporated by reference.

EXAMPLES

The present invention is specifically described below through Examples. The materials, use quantities, ratios, processing contents, processing procedures, and the like that are indicated in Examples below can be suitably modified without departing from the spirit of the present invention. Accordingly, the scope of the present invention is not limited to the specific examples given below.

All compounds that were synthesized were identified by $^1$H-NMR (300 MHz) or MALDI-TOF-MS. The melting points were measured with a micro melting point measuring apparatus (MP-500D, made by Yanako).

Synthesis Example 1

Synthesis of Compound 1-1-3

A 15.7 g quantity of 1,3-propanediol, 95 mg of n-dibutyltin diacetate, and 200 mL of THF were weighed out into a one-liter three-necked flask equipped with mechanical stirrer, temperature gauge, cooling tube, and dropping funnel. After adding dropwise 52.9 g of phenyl isocyanate with ice cooling to the three-necked flask, the mixture was reacted for 2 hours at room temperature. The reaction mixture was concentrated, n-hexane was added, and the white solid that precipitated was removed by filtration and dried, yielding 52 g (78% yield) of targeted Compound 1-1-3.

$^1$H-NMR (300 MHz, CDCl$_3$): δ2.05 (m, 2H), 4.29 (m, 4H), 6.69 (br, 2H), 7.06 (m, 2H), 7.24-7.42 (m, 8H)

Melting point: 140° C., molecular weight: 314

Synthesis Example 1-2

Synthesis of Compound 1-2

A 25 g quantity of 2-methylpentane-2,4-diol, 90 mg of n-dibutyltin diacetate, and 500 mL of THF were weighed out into a one-liter three-necked flask equipped with mechanical stirrer, temperature gauge, cooling tube, and dropping funnel. After adding dropwise 52.9 g of phenyl isocyanate with ice cooling to the three-necked flask, the mixture was reacted for 2 hours at 40° C. The reaction mixture was concentrated and purified by silica gel column chromatography (solvent: ethyl acetate/n-hexane). The white solid obtained was dried, yielding 40 g (53% yield) of targeted Compound 1-2.

$^1$H-NMR (300 MHz, CDCl$_3$): δ1.31 (d, 3H), 1.52 (s, 3H), 1.58 (s, 3H), 1.88 (d, 1H), 2.51 (dd, 1H), 5.26 (m, 1H), 6.44 (s, 1H), 6.52 (s, 1H), 7.03 (m, 2H), 7.20-7.25 (m, 8H)

Melting point: 139° C., molecular weight: 356

Synthesis Example 1-3

Synthesis of Compound 1-3

With the exception that the 2-methylpentane-2,4-diol was replaced with catechol, Compound 1-3 was synthesized (as a white solid) in the same manner as in Synthesis Example 1-2.

$^1$H-NMR (300 MHz, DMSO-d6): δ1.60 (d, 12H), 6.96 (t, 2H), 7.25 (t, 4H), 7.45 (m, 4H), 9.34 (br, 2H)

Molecular weight: 356

Synthesis Example 1-4

Synthesis of Compound 1-11

A 13.8 g quantity of glycerin, 100 mg of n-dibutyltin diacetate, and 200 mL of THF were weighed out into a 500 mL three-necked flask equipped with mechanical stirrer, temperature gauge, cooling tube, and dropping funnel. After adding dropwise 51.2 mL of phenyl isocyanate with ice cooling to the three-necked flask, the mixture was reacted for 2 hours at 40° C. The reaction mixture was concentrated, n-hexane was added, and the white solid that precipitated was removed by filtration. The white solid obtained was then recrystallized from methanol/water and dried, yielding 54 g (80% yield) of targeted Compound 1-11.

$^1$H-NMR (300 MHz, DMSO-d6): δ4.3 (m, 2H), 4.46 (m, 2H), 5.23 (m, 1H), 7.00 (t, 3H), 7.27 (t, 6H), 7.46 (m, 6H), 9.76 (br, 2H), 9.80 (br, 1H)

Melting point 186° C., Molecular weight: 449

Synthesis Example 1-5

Synthesis of Compound 1-12

With the exception that glycerin was replaced with trimethylolpropane, Compound 1-12 was synthesized (as a white solid, yield 75%) in the same manner as in Synthesis Example 1-4.

$^1$H-NMR (300 MHz, DMSO-d6): δ 0.94 (t, 3H), 1.54 (m, 2H), 4.15 (s, 6H), 6.98 (t, 3H), 7.27 (t, 6H), 7.46 (m, 6H), 9.64 (br, 3H)

Melting point 104° C., molecular weight 491

Synthesis Example 1-6

Synthesis of Compound 1-5

With the exception that the 2-methylpentane-2,4-diol was replaced with ethylene glycol, Compound 1-5 was synthesized in the same manner as in Synthesis Example 1-2.

Melting point 115° C., molecular weight: 372

Synthesis Example 1-7

Synthesis of a Mixture of Compounds 1-14 and 1-15

A 13.8 g quantity of glycerin, 90 mg of n-dibutyltin diacetate, and 200 mL of THF were weighed out into a 500 mL three-necked flask equipped with mechanical stirrer, temperature gauge, cooling tube, and dropping funnel. After adding dropwise 34.1 mL of phenyl isocyanate with ice cooling to the three-necked flask, the mixture was reacted for 2 hours at 40° C. The reaction mixture was concentrated, n-hexane was added, and the oily substance that separated out was separated by decantation and employed in the next step without alternation. The oily substance was charged to a 500 mL three-necked flask equipped with mechanical stirrer, temperature gauge, cooling tube, and dropping funnel and 200 mL of THF and 23.0 mL of triethylamine were added. With ice cooling, 19.32 mL of benzoyl chloride was gradually added dropwise. Subsequently, the mixture was reacted for 2 hours at 40° C. and cooled to room temperature. Ethyl acetate and water were then added and the organic phase was fractionated. The organic phase was purified with 1N hydrochloric aqueous solution and brine and dried with magnesium sulfate, after which the solvent was distilled off under reduced pressure. The mixture was purified by silica gel column chromatography (eluent: ethyl acetate/n-hexane (1/4)) and solidified with n-hexane, yielding 25 g of a mixture of the targeted Compounds 1-14 and 1-15 in the form of a white solid.

Melting point: 103° C.; molecular weight of 1-14: 362; molecular weight of 1-15: 434

Synthesis Example 1-8

Synthesis of Compound 1-22

With the exception that the phenyl isocyanate was replaced with benzyl isocyanate, Compound 1-22 was synthesized in the same manner as in Synthesis Example 1-2.

Melting point 99° C., molecular weight: 384

Synthesis Example 1-9

Synthesis of Compound 1-25

With the exceptions that the phenyl isocyanate was replaced with benzyl isocyanate and the 2-methylpentane-2,4-diol was replaced with hydroquinone, Compound 1-25 was synthesized in the same manner as in Synthesis Example 1-2.

Molecular weight: 376

Synthesis Example 1-10

Synthesis of Compound 1-26

A 22.8 g quantity of bisphenol A, 90 mg of n-dibutyltin diacetate, and 200 mL of THF were weighed out into a 500 mL three-necked flask equipped with mechanical stirrer, temperature gauge, cooling tube, and dropping funnel. After adding dropwise 26.6 g of benzyl isocyanate with ice cooling to the three-necked flask, the mixture was reacted for 2 hours at 40° C. The reaction mixture was concentrated and purified by silica gel column chromatography (solvent: ethyl acetate/n-hexane), yielding 31 g (63% yield) of targeted Compound 1-6.

Molecular weight: 494

Synthesis Example 2-1

Synthesis of Compound 2-3-3

A 157.1 g quantity of phenoxyethanol, 150 mg of n-dibutyltin diacetate, and 500 mL of THF were weighed out into a two-liter, three-necked flask equipped with mechanical stirrer, temperature gauge, cooling tube, and dropping funnel. A solution of 136.9 g of isophorone diisocyanate in 100 mL of THF was added dropwise over 30 minutes at room temperature to the three-necked flask. Subsequently, the mixture was reacted for 4 hours at 40° C. The reaction mixture was concentrated and purified by silica gel column chromatography (solvent: ethyl acetate/n-hexane), yielding 238 g (84% yield) of Compound 2-3-3 in the form of a white solid.

$^1$H-NMR (300 MHz, DMSO-d6): δ0.75-1.16 (m, 13H), 1.43 (br, 2H), 2.71 (br, 2H), 3.60 (br, 1H), 4.12 (m, 4H), 4.25 (m, 4H), 6.93 (m, 6H), 7.28 (m, 4H), 7.08-7.35 (m, 2H)

Melting point 96° C., molecular weight: 499

Synthesis Example 2-2

Synthesis of Compound 2-3-1

A 64.9 mL quantity of benzyl alcohol, 50 mg of n-dibutyltin diacetate, and 400 mL of THF were weighed out into a one-liter, three-necked flask equipped with mechanical stirrer, temperature gauge, cooling tube, and dropping funnel. A solution of 62.9 g of isophorone diisocyanate in 75 mL of THF was added dropwise over 30 minutes at room temperature to the three-necked flask. Subsequently, the mixture was reacted for 4 hours at 40° C. The reaction liquid was returned to room temperature, and then added to 500 mL of ethyl acetate and 1,000 mL of brine. Extraction was conducted with ethyl acetate. The mixture was cleaned twice with brine and dried with magnesium sulfate. The solvent was then distilled off under reduced pressure.

The reaction mixture was concentrated and purified by silica gel column chromatography (solvent: ethyl acetate/n-hexane), The white solid obtained was dispersed and cleaned with hexane, filtered, and dried, yielding 70 g (53% yield) of Compound 2-3-1.

$^1$H-NMR (300 MHz, DMSO-d6): δ0.88-1.15 (m, 13H), 1.48 (br, 2H), 2.74 (d, 2H), 3.61 (br, 1H), 5.00 (m, 4H), 7.12 (br, 1H), 7.30-7.36 (m, 11H)

Melting point 105° C., molecular weight: 426

Synthesis Example 2-3

Synthesis of Compounds 2-3-2, 2-9-1, and 2-11

With the exceptions that the phenoxyethanol in Synthesis Example 2-1 was replaced with phenethyl alcohol, cyclohexanol, and phenol, Compounds 2-3-2, 2-9-1, and 2-11 were synthesized in the same manner.
(2-3-2) Glassy solid, molecular weight: 467
(2-9-1) Melting point 155° C., molecular weight 422
(2-11) Melting point 168° C., molecular weight: 410

Synthesis Example 2-4

Synthesis of Compound 2-1-1

With the exception that isophorone diisocyanate was replaced with toluene diisocyanate in Synthesis Example 2-1, 2-1-1 was synthesized in the same manner.

Melting point 141° C., molecular weight: 449

Synthesis Example 2-5

Synthesis of Compound 2-2-3

With the exceptions that isophorone diisocyanate was replaced with 4,4'-diphenylmethane diisocyanate and phenoxyethanol was replaced with 1-methoxy-2-propanol in Synthesis Example 2-1, Compound 2-2-3 was synthesized in the same manner.
Molecular weight: 416

Synthesis Example 2-6

Synthesis of Compound 2-2-4

With the exceptions that the isophorone diisocyanate was replaced with 4,4'-diphenylmethane diisocyanate and the phenoxyethanol was replaced with t-butanol in Synthesis Example 2-1, Compound 2-2-4 was synthesized in the same manner.
Molecular weight: 398

Synthesis Example 2-7

Synthesis of Compound 2-1-2

With the exceptions that the isophorone diisocyanate was replaced with tolylene diisocyanate and the phenoxyethanol was replaced with benzyl alcohol in Synthesis Example 2-1, Compound 2-1-2 was synthesized in the same manner.
Melting point 98° C., molecular weight: 451

Synthesis Example 2-8

Synthesis of Compound 2-7-1

With the exception that the isophorone diisocyanate was replaced with 1,3-bis(2-isocyanato-2-propyl) and the phenoxyethanol was replaced with benzyl alcohol in Synthesis Example 2-1, Compound 2-7-1 was synthesized in the same manner.
$^1$H-NMR (300 MHz, CDCl$_3$): δ 1.62 (s, 12H), 5.00 (s, 4H), 5.09 (br, 2H), 7.23-7.40 (m, 14H)
Melting point 78° C., molecular weight: 460

Synthesis Example 2-9

Synthesis of Compound 2-6-3

With the exception that the isophorone diisocyanate was replaced with 1,3-xylylene diisocyanate in Synthesis Example 2-1, Compound 2-6-3 was synthesized in the same manner.
$^1$H-NMR (300 MHz, CDCl$_3$): δ4.15 (m, 4H), 4.32 (m, 4H), 4.45 (m, 4H), 5.09 (br, 2H), 6.85-6.98 (m, 6H), 7.12-7.30 (m, 8H)
Molecular weight: 465

Synthesis Example 2-10

Synthesis of Compound 2-4-3

With the exception that the isophorone diisocyanate was replaced with 1,3-bis(isocyanatomethyl)cyclohexane in Synthesis Example 2-1, Compound 2-4-3 was synthesized in the same manner.
Molecular weight: 471

Synthesis Example 2-11

Synthesis of Compound 2-5-3

With the exception that the isophorone diisocyanate was replaced with 1,3-cyclohexylene diisocyanate in Synthesis Example 2-1, Compound 2-5-3 was synthesized in the same manner.
Molecular weight: 443

Synthesis Example 2-12

Synthesis of Compound 2-9-2

With the exception that the phenoxyethanol was replaced with diethylene glycol monophenyl ether in Synthesis Example 2-1, Compound 2-9-2 was synthesized in the same manner.
Molecular weight: 586

Synthesis Example 2-13

Synthesis of a mixture of Compounds 2-9-3 and 2-9-4

A 27.6 g quantity of phenoxyethanol, 100 mg of n-dibutyltin diacetate, and 100 mL of THF were weighed out into a 500 mL, three-necked flask equipped with mechanical stirrer, temperature gauge, cooling tube, and dropping funnel. A 44.4 g quantity of isophorone diisocyanate was added dropwise at room temperature to the three-necked flask. Subsequently, the mixture was reacted for 2 hours at 40° C., 50 mL of methanol was added, and the mixture was reacted for another 2 hours. The reaction mixture was concentrated and purified by silica gel column chromatography (solvent: ethyl acetate/n-hexane), yielding a mixture (34 g) of Compounds 2-9-3 and 2-9-4 in the form of a transparent, viscous liquid (yield 45%).
Molecular weight: 392

Synthesis Example 2-14

Synthesis of Compound 2-6-1

With the exceptions that the isophorone diisocyanate was replaced with xylylene diisocyanate and the phenoxyethanol was replaced with benzyl alcohol in Synthesis Example 2-1, Compound 2-6-1 was synthesized in the same manner.
$^1$H-NMR (300 MHz, CDCl$_3$): δ 4.38 (m, 4H), 5.07 (br, 2H), 5.16 (s, 4H), 7.16-7.40 (m, 14H)
Melting point 138° C., molecular weight: 404

Synthesis Example 2-15

Synthesis of Compound 3-7

With the exception that the phenoxyethanol was replaced with 2-phenoxypropanol in Synthesis Example 2-1, Compound 3-7 was synthesized in the same manner.
MALDI-TOFMS M+Na: 549

Synthesis Example 2-16

Synthesis of a Mixture of Compounds 3-1, 3-2, 3-4, and 3-5

With the exception that the phenoxyethanol was replaced with 1-benzoyloxy-2-propanol and 1-benzoyloxyethanol in Synthesis Example 2-1, Compounds 3-1 and 3-2 were synthesized in the same manner.
Compound 3-1 MALDI-TOFMS M+Na: 605
Compound 3-2 MALDI-TOFMS M+Na: 577

Synthesis Example 2-17

With the exception that the phenoxyethanol was replaced with a mixture of phenoxyethanol and 1-benzoyloxy-2- propanol in Synthesis Example 2-1, a mixture of Compounds 3-4 and 3-5 was synthesized in the same manner.

Mixture of Compounds 3-4 and 3-5 MALDI-TOFMS M+Na: 563

Synthesis Example 2-18

Synthesis of Compound 3-8

With the exception that the phenoxyethanol was replaced with 1-benzoyloxy-2-propanol and the isophorone diisocyanate was replaced with xylylene diisocyanate in Synthesis Example 2-1, Compound 3-8 was synthesized in the same manner.

MALDI-TOFMS M+Na: 571
$^1$H-NMR (300 MHz, DMSO-d6): δ1.25 (d, 6H), 4.10 (d, 4H), 4.22 (m, 2H), 5.05 (m, 2H), 7.03 (m, 2H), 7.50 (t, 4H), 7.63 (m, 4H), 7.95 (d, 4H)

Synthesis Example 2-19

Synthesis of Compound 3-9

With the exception that the phenoxyethanol was replaced with 1-benzoyloxyethanol and the isophorone diisocyanate was replaced with xylylene diisocyanate in Synthesis Example 2-1, Compound 3-9 was synthesized in the same manner.

Compound 3-9 MALDI-TOFMS M+Na: 543

Synthesis Example 2-20

Synthesis of Mixture of Compounds 3-14 and 3-15

With the exception that the phenoxyethanol was replaced with 1-benzoyloxy-2-propanol in Synthesis Example 2-13, a mixture of Compounds 3-14 and 3-15 was synthesized in the same manner.

Compound 3-16 MALDI-TOFMS M+Na: 429

Synthesis Example 2-20

Synthesis of Compound 3-16

With the exception that the phenoxyethanol was replaced with 1-benzoyloxyethanol and the isophorone diisocyanate was replaced with xylylene diisocyanate in Synthesis Example 2-13, Compound 3-16 was synthesized in the same manner.

Compound 3-16 MALDI-TOFMS M+Na: 409

Synthesis Example 2-21

Synthesis of Compound 4-13

A 57.64 g quantity of propylene carbonate and 55.00 g of benzylamine were added to a one-liter, three-necked flask equipped with mechanical stirrer, temperature gauge, cooling tube, and dropping funnel and the mixture was reacted for 6 hours at 90° C. The mixture was cooled to room temperature, 210 mL of toluene, 130 mL of water, and 2 mL of 12N hydrochloric acid were added and a liquid separation operation was conducted. A further liquid separation operation was conducted with 140 mL of water. The organic layer obtained was concentrated, yielding a mixture (107.4 g) of 1-hydroxypropane-2-yl=benzyl carbamate and 2-hydroxypropyl=benzyl dicarbamate.

Next, the mixture (38 g) of 1-hydroxypropane-2-yl=benzyl carbamate and 2-hydrooxypropyl=benzyl dicarbamate synthesized above, an organic tin catalyst (Neostan U-830, made by Nitto Kasei Corp.) (0.32 g), 262 mL of ethyl acetate, and 158 mL of hexane were added to a 500 mL, three-necked flask equipped with mechanical stirrer, temperature gauge, cooling tube, and dropping funnel and the mixture was cooled to an internal temperature of 5° C. To this was added dropwise m-xylylene diisocyanate (17.5 g). Once the dropwise addition had been completed, the mixture was reacted for 2 hours at 70° C. Subsequently, the internal temperature was lowered to 60° C. and 8 mL of methanol was added. The mixture was reacted for 1 hour, cooled to 45° C., and filtered. The mixture was cleaned with 175 mL of hexane and dried, yielding white solid 4-13 (56 g).

Compound 4-13 $^1$H-NMR (300 MHz, DMSO): δ1.1-1.3 (m, 6H), 3.9-4.3 (m, 12H), 4.8 (m, 2H), 7.0-7.3 (m, 14H), 7.6-7.8 (m, 4H).

Synthesis Example 2-22

Synthesis of Compound 4-14

The mixture (20.4 g) of 1-hydroxypropane-2-yl=benzyl carbamate and 2-hydrooxypropyl=benzyl dicarbamate synthesized above, an organic tin catalyst (Neostan U-830, made by Nitto Kasei Corp.) (0.15 g), and 50 mL of ethyl acetate were added to a 500 mL, three-necked flask equipped with mechanical stirrer, temperature gauge, cooling pipe, and dropping funnel and the internal temperature was cooled to 5° C. Isophorone diisocyanate (11.1 g) was added dropwise. When the dropwise addition had ended, the mixture was reacted for 5 hours at 70° C. Subsequently, the mixture was cooled to room temperature, concentrated, and isolation purified by silica gel column chromatography, yielding viscous solid 4-14 (18 g).

Compound 4-14 $^1$H-NMR (300 MHz, DMSO): δ0.7-1.6 (m, 21H), 2.6-2.7 (m, 2H), 3.5-3.7 (m, 1H), 3.9-4.1 (m, 4H), 4.1-4.2 (m, 4H), 4.7-5.0 (m, 2H), 6.9-7.4 (m, 12H), 7.6-7.7 (m, 2H).

The other compounds shown in Table 2 were also synthesized according to the above synthesis method. The fact that the targeted compounds had been obtained was confirmed by either $^1$H-NMR (300 MHz) or MALDI-TOF-MS.

Synthesis Example 101

Synthesis of Compound 101-20

A 44.3 g (0.20 mol) quantity of isophorone diisocyanate and 150 mL of THF were weighed out into a three-necked flask equipped with mechanical stirrer, temperature gauge, cooling tube, and dropping funnel. A solution of 44.8 g of morpholine in 50 mL of THF was added dropwise to the three-necked flask over 60 minutes with ice cooling at less than or equal to 20° C. Subsequently, the mixture was reacted at room temperature for 2 hours. When the reaction had ended, hexane was added and the solid obtained was filtered out. This rough material was liquid separated with ethyl acetate and saturated brine. The organic layer was concentrated and purified by recrystallization, yielding 35 g of Compound 101-20 (44% yield).

MALDI-TOF-MS M+Na: 419

Synthesis Example 102

Synthesis of a Mixture of Compounds 101-9-A and 101-9-B

A 44.4 g (0.20 mol) of isophorone diisocyanate and 150 ML of THF were weighed out into a three-necked flask equipped with mechanical stirrer, temperature gauge, cooling tube, and dropping funnel. A solution of 21.78 g (0.25 mol) of morpholine in 50 mL of THF was added dropwise at 10° C. with ice cooling. Subsequently, the mixture was stirred for 2 hours at room temperature, 10 mg of n-dibutyltin diacetate and 20.7 g (0.15 mol) of phenoxyethanol were added dropwise at room temperature. The mixture was then reacted for another four hours at 40° C. When the reaction had ended, the solvent was concentrated and the product was purified by silica gel column chromatography (solvent: ethyl acetate/n-hexane), yielding 37 g of a mixture of Compounds 101-9-A and 101-9-B in the form of a glassy solid (yield 40%).

MALDI-TOF-MS M+Na: 470

Synthesis Example 103

The morpholine was replaced with ethylamine, benzylamine, cyclohexylamine, dimethylamine, dipropylamine, and aniline, respectively, to synthesize a mixture of Compounds 101-1-A/101-1-B, a mixture of Compounds 101-3-A/101-3-B, a mixture of Compounds 101-4-A/101-4-B, a mixture of 101-6-A/101-6-B, a mixture of 101-7-A/101-7-B, and a mixture of 101-8-A/101-8-B.

Compounds 101-25, 102-6, 101-24, and 102-4 were synthesized by the same synthesis method, The other compounds shown in Table 3 were also synthesized in accordance with the above synthesis method. The fact that the targeted compounds had been obtained was confirmed by either $^1$H-NMR (300 MHz) or MALDI-TOF-MS.

Example 1

Forming a Cellulose Acylate Film (Preparation of Cellulose Acylate Solution)

The composition indicated below was charged to a mixing tank and stirred to dissolve the various components, and a cellulose acylate solution was prepared.

| Composition of cellulose acylate solution | |
|---|---|
| Cellulose acylate with degree of acetyl substitution 2.87 and degree of polymerization 370 | 100.0 mass parts |
| Compound indicated in Table 2 below | 10.0 mass parts |
| Methylene chloride (First solvent) | 353.9 mass parts |
| Methanol (Second solvent) | 89.6 mass parts |
| n-Butanol (Third solvent) | 4.5 mass parts |

Using a drum casting device, the cellulose acylate solution prepared above was cast. Peeling was conducted in a state where the amount of residual solvent in the dope was about 70 mass % and drying was conducted in a state where the amount of residual solvent was 3 to 5 mass %. Subsequently, the product was conveyed between the rolls of a heat treatment device to conduct further drying, yielding the cellulose acylate film of Example 1. The thickness of the cellulose acylate film that had been manufactured was 60 μm. The other films were also fabricated in the same manner.

—Measurement of Surface Hardness of Cellulose Acylate Film—

A "Fischerscope H100 V p-type hardness meter" made by Fischer Instruments (Ltd.) was employed. By means of a Knoop indenter disposed such that the short axis of the indenter was oriented parallel to the direction of conveyance (longitudinal direction; test direction in the pencil hardness test) during formation of the cellulose acylate film, the surface of a sample fixed on a glass substrate was measured under conditions of a load time of 10 s, a creep time of 5 s, a load removal time of 10 s, and a maximum load of 50 mN. The hardness was calculated from the relation between the contact area of the sample with the indenter as determined from the pressing depth, and the maximum load. The average of values from 5 points was adopted as the surface hardness.

Further, employing a "Fischerscope H100 V p-type hardness meter" made by Fischer Instruments (Ltd.), the sample surface fixed on a glass substrate was measured in accordance with the method of JIS Z 2251 under conditions of a load time of 10 s, a creep time of 5 s, a load removal time of 10 s, and an indentation load of 50 mM. The hardness was calculated from the relation between the contact area of the sample with the indenter as determined from the pressing depth, and the maximum load. JIS Z 2251 is a Japanese Industrial Standard created based on ISO4545.

At the same indentation position, the Knoop indenter was rotated by increments of 10° and measurements were taken at a total of 18 equally spaced angular rotations to measure the Knoop hardness in all directions. When the minimum value was obtained, it matched the surface hardness that was measured when the orientation of the short axis of the Knoop indenter was disposed parallel to the conveyance direction (longitudinal direction: test direction in the pencil hardness test) during forming of the cellulose acylate film.

The results of evaluation on the scale given below are given in the table in units of N/mm².

A+: Knoop hardness of greater than or equal to 220 N/mm$^2$
A: Knoop hardness of greater than or equal to 210 N/mm$^2$ but less than 220 N/mm$^2$
B: Knoop hardness of greater than or equal to 200 N/mm$^2$ but less than 210 N/mm$^2$
C: Knoop hardness of greater than or equal to 190 N/mm$^2$ but less than 200 N/mm$^2$
D: Knoop hardness of less than 190 N/mm$^2$ —Method of Evaluating Inhibition of Light Tinting—

A Super Xenon Weather Meter (SX75, made by Suga Test Instruments Co., Ltd.) was used to irradiate the various cellulose acylate films obtained above with light for 96 hours. Whether light tinting was present was evaluated based on the change in hue b* before and after irradiation. The evaluation was conducted based on the scale given below and the results are given in the table.

The film hue b* was determined with a UV3150 spectrophotometer made by Shimadzu Corporation. As the value of the hue b* becomes increasingly negative, the blueness of the transmitted light increases, and as the value becomes increasingly positive, the yellowness increases. Films exhibiting light tinting of a degree of an evaluation score of D have pronounced yellowish in actual use.

A: The amount of change in b* before and after irradiation was less than or equal to 0.1
B: The amount of change in b* before and after irradiation was more than 0.1 but less than or equal to 0.25
C: The amount of change in b* before and after irradiation was more than 0.25 but less than or equal to 0.40

D: The amount of change in b* before and after irradiation was more than 0.40

—Method of Evaluating Volatility—

A TG/DTA measurement device (TG/DTA 7200 made by SII Nanotechnologies Corp.) was employed. Each compound was heated from room temperature to 140° C., the change in weight of the compound when maintained for one hour at 140° C. was measured, and the volatility was determined under the following conditions.

A change in weight determined by measurement that was less than or equal to 0.1% was denoted as "None," and any change greater than that was denoted as "Present" in the table.

TABLE 2

| | Additive | | Film performance | | | Additive Structure | | | |
| | Type, content | | Surface | Inhibition | | | Number of divalent linking group denoted by | | |
| Film No. | Compound No. | Content (wt %*) | hardness (N/mm²) | of light tinting | Volatility | Molecular weight | —O—C(=O)—NH— per molecule | Equivalent U | Remarks |
|---|---|---|---|---|---|---|---|---|---|
| 101 | 1-1-3 | 10 | 209 | B | B | None | 314 | 2 | 157 | Ex. |
| 102 | 1-2 | 10 | 224 | A+ | B | None | 356 | 2 | 178 | Ex. |
| 103 | 1-3 | 10 | 214 | A | B | None | 356 | 2 | 178 | Ex. |
| 104 | 1-5 | 10 | 204 | B | B | None | 372 | 2 | 186 | Ex. |
| 105 | 1-11 | 10 | 225 | A+ | B | None | 449 | 3 | 150 | Ex. |
| 106 | 1-12 | 10 | 211 | A | B | None | 491 | 3 | 164 | Ex. |
| 107 | (1-14/1-15) | 10 | 224 | A+ | B | None | 362, 434 | 2 | 181, 217 | Ex. |
| 108 | 1-22 | 10 | 204 | B | A | None | 384 | 2 | 192 | Ex. |
| 109 | 1-25 | 10 | 209 | A | A | None | 376 | 2 | 188 | Ex. |
| 110 | 1-26 | 10 | 207 | B | A | None | 494 | 2 | 247 | Ex. |
| 112 | 2-1-1 | 10 | 224 | A+ | C | None | 449 | 2 | 225 | Ex. |
| 113 | 2-1-2 | 10 | 226 | A+ | C | None | 451 | 2 | 226 | Ex. |
| 114 | 2-2-3 | 10 | 208 | B | B | None | 499 | 2 | 250 | Ex. |
| 115 | 2-2-4 | 10 | 205 | B | B | None | 398 | 2 | 199 | Ex. |
| 116 | 2-3-1 | 10 | 213 | A | A | None | 426 | 2 | 213 | Ex. |
| 117 | 2-3-2 | 10 | 213 | A | A | None | 467 | 2 | 234 | Ex. |
| 118 | 2-3-3 | 10 | 219 | A | A | None | 499 | 2 | 250 | Ex. |
| 119 | 2-4-3 | 10 | 212 | A | A | None | 471 | 2 | 236 | Ex. |
| 120 | 2-5-3 | 10 | 220 | A+ | A | None | 443 | 2 | 222 | Ex. |
| 121 | 2-6-1 | 10 | 202 | B | A | None | 404 | 2 | 202 | Ex. |
| 122 | 2-7-1 | 10 | 205 | B | A | None | 460 | 2 | 230 | Ex. |
| 123 | 2-9-1 | 10 | 203 | B | A | None | 422 | 2 | 211 | Ex. |
| 124 | 2-11 | 10 | 222 | A+ | A | None | 443 | 2 | 222 | Ex. |
| 125 | 2-9-2 | 10 | 211 | A | A | None | 586 | 2 | 293 | Ex. |
| 126 | (2-9-3/2-9-4) | 10 | 207 | B | A | None | 392 | 2 | 196 | Ex. |
| 126 | 3-1 | 10 | 223 | A+ | A | None | 583 | 2 | 292 | Ex. |
| 127 | 3-2 | 10 | 222 | A+ | A | None | 555 | 2 | 278 | Ex. |
| 128 | 3-8 | 10 | 225 | A+ | A | None | 549 | 2 | 275 | Ex. |
| 129 | (3-4/3-5) | 10 | 220 | A+ | A | None | 541 | 2 | 271 | Ex. |
| 130 | 3-7 (3-14/3-15) | 10 | 218 | A | A | None | 527 407 | 2 | 264 204 | Ex. |
| 131 | 2-3-3 (2-9-3/2-9-4) | 10 | 217 | A | A | None | 499 392 | 2 | 250 196 | Ex. |
| 132 | 4-1 | 10 | 204 | B | A | None | 587 | 4 | 147 | Ex. |
| 133 | 4-3 | 10 | 209 | B | A | None | 619 | 4 | 155 | Ex. |
| 134 | 4-5 | 10 | 213 | B | A | None | 635 | 4 | 159 | Ex. |
| 135 | 4-8 | 10 | 215 | A | A | None | 579 | 4 | 145 | Ex. |
| 136 | 4-10 | 10 | 218 | A | A | None | 613 | 4 | 153 | Ex. |
| 137 | 4-11 | 10 | 222 | A+ | A | None | 430 | 3 | 143 | Ex. |
| 138 | 4-12 | 10 | 220 | A+ | A | None | 464 | 3 | 155 | Ex. |
| 139 | 4-13 | 10 | 224 | A+ | A | None | 607 | 4 | 152 | Ex. |
| 140 | 4-14 | 10 | 220 | A+ | A | None | 641 | 4 | 160 | Ex. |
| 141 | 4-15 | 10 | 223 | A+ | A | None | 607 | 4 | 152 | Ex. |
| 142 | 4-16 | 10 | 219 | A+ | A | None | 641 | 4 | 160 | Ex. |
| 143 | Comp. Compound 1 | 10 | 204 | B | D | None | 484 | 2 | 242 | Comp. Ex. |
| 144 | Comp. Compound 2 | 10 | 201 | B | B | Present | 221 | 1 | 221 | Comp. Ex. |
| 145 | Comp. Compound 3 | 10 | 183 | D | A | Present | 225 | 1 | 225 | Comp. Ex. |
| 146 | Comp. Compound 4 | 10 | 175 | D | D | None | >2000 | >2 | 1000 or more | Comp. Ex. |
| 147 | Comp. Compound 5 | 10 | 186 | D | D | None | 1174 | 2 | 587 | Comp. Ex. |
| 148 | None | 0 | 180 | D | A | — | — | — | — | Comp. Ex. |

*wt % is mass % of the additive relative to 100 mass % of cellulose acylate. Two types of additives in the parentheses were employed in the form of a mixture obtained in the synthesis example. In films 130, 131, the compound indicated outside the parentheses and the mixture of two types of the compounds in the parentheses were employed in a mixing ratio of 1:1 (mass ratio).

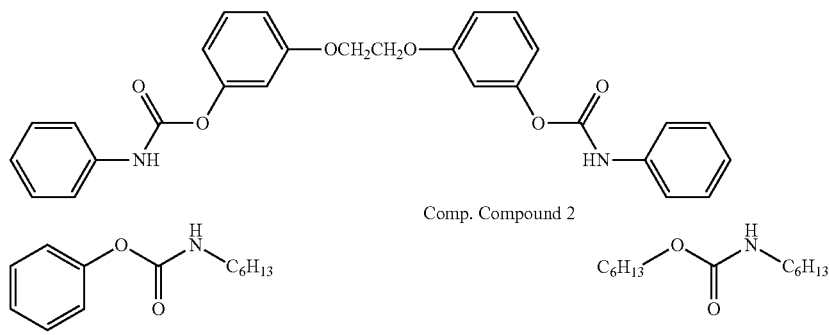

Comp. Compound 1

Comp. Compound 2

Comp. Compound 3

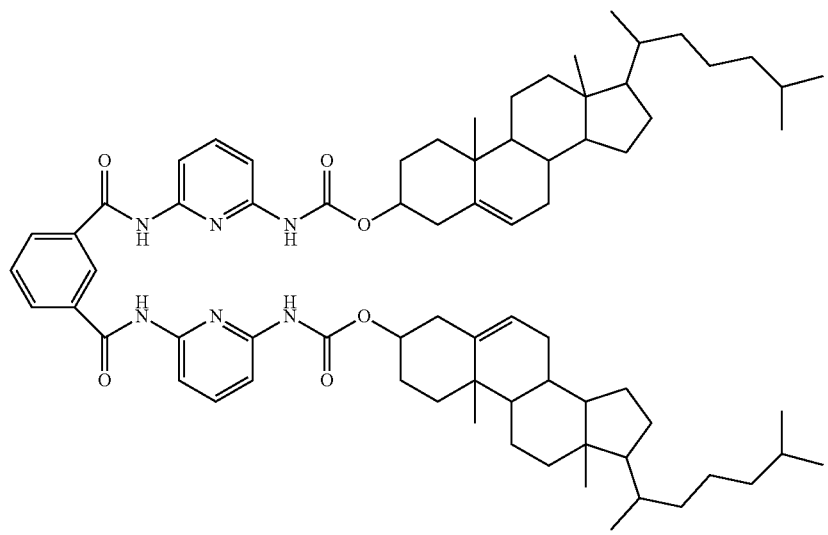

Comp. Compound 5

Comparative Compound 1 is Compound A-23 (molecular weight 484) described in JP-A-No. 2005-272566. Comparative Compound 2 was Compound A-32 (molecular weight 221.3) of the same. And Comparative Compound 3 was Compound A-29 (molecular weight 225.3) of the same.

Comparative Compound 4 is polyurethane (cellulose acetate modifying agent C1 described in JP-A-No. 2004-175971, paragraph 0043) in the form of a condensation product of polyester (molecular weight 2,000) comprised of polyethylene glycol/1,4-butylene glycol/succinic acid, and tolylene diisocyanate.

Comparative Compound 5 is Compound (48) described in JP-A-No. 2002-322294.

The Knoop hardness is an indicator of the surface hardness of a film. As shown in Table 2, the compounds employed in Examples all formed films exhibiting larger surface hardness than Comparative Compounds 3 and 4. Compared to Comparative Compounds 4 and 5, the compounds denoted by general formula (I) that were employed in the examples exhibited lower values of equivalent U. A high content of the divalent linking group denoted by —O—C(=O)—NH—, that is, a high content of the group that interacts with cellulose acylate caused efficient hydrogen bonding with the side chain of the cellulose acylate, inhibiting movement of the molecular chain of cellulose acylate. This was thought to contribute to increasing the surface hardness of the film. Further, the proton portion in the divalent linking group denoted by —O—C(=O)—NH— was thought to efficiently act on the acetyl group and hydroxyl group in cellulose acylate to form hydrogen bonds, inhibiting movement of the polymer chain of cellulose acylate and contributing to enhanced hardness.

A comparison of Film Nos. 115, 116, 122, and 123 indicates that compared to an aliphatic ring (cyclohexanone ring) (Film No. 122) as the terminal ring structure, films containing a compound having an aromatic ring (benzene ring) (Film Nos. 115, 116, and 123) were found to have better hardness. Compounds having benzene rings were thought to have high affinity for cellulose acylate and tend to enter into the spaces in the polymer chain of cellulose acylate.

The contribution of the substituents adjacent to divalent linking groups denoted by —O—C(=O)—NH— was found to be great in inhibiting light tinting in the films. Films containing compounds in which alkylene groups were bonded to divalent linking groups denoted by —O—C(=O)—NH— all exhibited little light tinting (were scored A).

Comparative Compound 1, in which a nitrogen atom and oxygen atom were directly bonded to the benzene ring, and Comparative Compound 5, in which a nitrogen atom and carbon atom were directly bonded to the benzene ring, were found to exhibit particularly high light tinting and were unpreferable as additives for optical films. By contrast, films containing compounds in which the benzene ring was directly bonded directly to just a nitrogen atom were found to exhibit good evaluation results with regard to inhibiting light tinting (scores of B and C). Films in which benzene rings directly bonded to nitrogen atoms were unsubstituted (Film Nos. 101-107) and films containing compounds having alkyl groups or alkoxy groups (Film Nos. 113, 114) exhibited better evaluation results (score of B) with regard to inhibiting light tinting than films containing conjugating substituents (Nos. 111, 112) (score of C).

Comparative Compounds 2 and 3 were extremely inferior with regard to volatility. By contrast, the compounds employed in Examples were found to have low-volatility.

From the above results, the first aspect of the present invention was found to yield cellulose acylate films of great hardness and little light tinting. Since the compound denoted by general formula (I) had little volatility, it made it possible to manufacture cellulose acylate films with good transparency.

Example 1-2

With the exception that the types of the various additives and quantities added were changed as indicated in the table below, cellulose acylate films were prepared in the same manner as in Example 1.

The various characteristics were evaluated in the same manner as in Example 1. The results are given in Table 3 below.

The various characteristics were evaluated in the same manner as in Example 1.

The value of the Knoop hardness of each of the films was compared to the value of the Knoop hardness of the film fabricated without adding the additives and evaluated based on the following scale.

A: Greater than or equal to 1.15-fold the value of the Knoop hardness when the additives were not added B: Greater than or equal to 1.05-fold but less than 1.15-fold the Knoop hardness when the additives were not added C: Greater than or equal to 1.00-fold but less than 1.05-fold the Knoop hardness when the additives were not added D: Less than 1.00-fold the Knoop hardness when the additives were not added The above results are given in Table 4.

TABLE 4

| Film No. | Cellulose acylate Degree of acetyl substitution | Additive Compound No. | Additive Content (wt %*) | Film thickness (μm) | Film Performance Surface hardness | Film Performance Light tinting | Volatility | Remarks |
|---|---|---|---|---|---|---|---|---|
| 301 | 2.42 | 1-2 | 10 | 54 | A | B | None | Ex. |
| 302 | 2.42 | 1-5 | 10 | 61 | B | B | None | Ex. |
| 303 | 2.77 | 1-11 | 10 | 62 | A | B | None | Ex. |
| 304 | 2.93 | 1-11 | 10 | 57 | A | B | None | Ex. |
| 305 | 2.93 | 2-3-3 | 10 | 59 | A | A | None | Ex. |
| 306 | 2.93 | 2-5-3 | 10 | 60 | A | A | None | Ex. |
| 307 | 2.87 | 2-6-3 | 10 | 61 | A | A | None | Ex. |
| 308 | 2.87 | 3-9 | 10 | 63 | A | A | None | Ex. |
| 309 | 2.87 | (3-14/3-15) | 10 | 60 | A | A | None | Ex. |
| 310 | 2.87 | 3-16 | 10 | 59 | A | A | None | Ex. |
| 311 | 2.87 | 3-9 3-16 | 10 | 59 | A | A | None | Ex. |

*wt % is mass % of the additive relative to 100 mass % of cellulose acylate. Two types of additives in the parentheses were employed in the form of a mixture obtained in the synthesis example. In film 311, the mixing ratio of Compound 3-9 and Compound 3-16 is 1:1 (mass ratio).

TABLE 3

| | Additives | | Film performance | | |
|---|---|---|---|---|---|
| Film No. | Compound No. | Content (wt %*) | Surface hardness | Inhibition of light tinting | Volatility |
| 201 | 2-3-3 | 5 | 206 | A | A | None |
| 202 | 2-3-3 | 25 | 238 | A+ | A | None |
| 203 | 3-1 | 5 | 201 | B | A | None |
| 204 | 3-1 | 7.5 | 210 | A | A | None |

*wt % is mass % of the additive relative to 100 mass % of cellulose acylate

Example 2

With the exceptions that the degree of substitution and the types of additives of the cellulose acylate were changed as indicated in the table below, cellulose acylate films were fabricated in the same manner as in Example 1.

As shown in Table 4, the above compounds were found to permit the realization of preferable surface hardness irrespective of the degree of substitution of the cellulose acylate.

Example 3

With the exceptions that the type of cellulose acylate, the type of the various additives, and the thickness of the cellulose acylate film were varied as indicated in the following table, a cellulose acylate film was fabricated in the same manner as in Example 1.

The various characteristics were evaluated in the same manner as in Example 1. However, in the course of evaluating the surface hardness, the indentation load was changed to 20 mN in measuring the films that were less than or equal to 40 μm in thickness.

—Evaluation of Surface Hardness—

The surface hardness of the cellulose acylate films obtained as set forth above were measured by the same method as that described in Example 1 with the exception that the indentation load was changed as set forth above. The unit was denoted in N/mm².

The value of the Knoop hardness of each of the films was compared to the value of the Knoop hardness of the film fabricated without adding additives and evaluated based on the following scale.
A: Greater than or equal to 1.15-fold the value of the Knoop hardness when the additives were not added
B: Greater than or equal to 1.05-fold but less than 1.15-fold the Knoop hardness when the additives were not added
C: Greater than or equal to 1.00-fold but less than 1.05-fold the Knoop hardness when the additives were not added
D: Less than 1.00-fold the Knoop hardness when the additives were not added

TABLE 5

| Film No. | Cellulose acylate Acetyl substitution | Additive Compound No. | Additive Content (wt %*) | Film thickness (μm) | Film Performance Surface hardness | Film Performance Light tinting | Volatility | Remarks |
|---|---|---|---|---|---|---|---|---|
| 401 | 2.86 | 1-2 | 12 | 31 | A | B | None | Ex. |
| 402 | 2.86 | 1-11 | 12 | 26 | A | B | None | Ex. |
| 403 | 2.86 | 2-3-3 | 12 | 23 | A | A | None | Ex. |
| 404 | 2.86 | 2-9-1 | 12 | 42 | B | A | None | Ex. |
| 405 | 2.86 | Comp. Compound 4 | 12 | 27 | D | B | None | Ex. |

*wt % is mass % of the additive relative to 100 mass % of cellulose acylate.

As indicated in Table 5, the films of Examples were found to realize preferable surface hardness even at reduced thickness.

Example 4

Fabrication of Optical Film with Hard Coat Layer

A hard coat layer solution of the following curable composition was coated on the surfaces of single-layer optical films comprised of each of cellulose acylates fabricated above, ultraviolet radiation was irradiated to cure the compositions, and each optical film on which was formed a hard coat layer 6 μm in thickness was fabricated.

| Curable composition of hard coat layer solution | |
|---|---|
| Monomer: Pentaerythritol triacrylate/pentaerythritol tetraacrylate (mixing mass ratio 3/2) | 53.5 mass parts |
| UV initiator Irgacure TM907 (made by Ciba Specialty Chemicals (Ltd.)) | 1.5 mass parts |
| Ethyl acetate | 45 mass parts |

—Evaluation of Pencil Hardness—

Each of the cellulose acylate films with a hard coat was placed under conditions of 25° C. at 60% relative humidity for two hours. The test pencils specified in JIS-S6006 was then used to repeatedly scratch 5 times the surface of the hard coat layer with pencils of various hardness using a weight of 500 g in accordance with the pencil hardness evaluation method specified in JIS-K5400, and the hardness at which one scratch was made was measured. In JIS-K5400, a scratch is defined as a break or rub mark in the coating, and not a dent in the coating. However, in the present evaluation, dents in the coating were judged to be scratches. In practical use, 3H or higher is preferable. The higher the number, the greater the hardness, being preferred.

As a result, the films to which the compound denoted by general formula (I) was added were all found to achieve high scores of 3H.

Example 5

Fabrication of Polarizing Plate

Saponification Treatment of Polarizing Plate Protective Film

Each of the cellulose acylate films obtained in Example 1 was immersed for 3 minutes at 55° C. in a 2.3 mol/L aqueous solution of sodium hydroxide, rinsed in a water washing bath at room temperature, and neutralized with 0.05 mol/L of sulfuric acid at 30° C. The film was then rinsed again at room temperature in a water washing bath and dried with warm air at 100° C. The surface of the cellulose acylate film was thus subjected to a saponification treatment.

Fabrication of Polarizing Plate

A polarizer was fabricated by adsorbing iodine onto a stretched polyvinyl alcohol film.

The saponified cellulose acylate film was bonded with a polyvinyl alcohol adhesive to one side of the polarizer. A commercial cellulose triacetate film (Fujitac D80UF, made by FUJIFILM Corporation) was subjected to the same saponification treatment and then bonded with polyvinyl alcohol adhesive to the surface on the opposite side of the polarizing plate from that on which the various cellulose acylate films fabricated above had been bonded.

In this process, the films were disposed so that the transmission axis of the polarizer was parallel to the slow axis of the cellulose acylate film, and the transmission axis of the polarizer was perpendicular to the slow axis of the commercial cellulose triacetate film.

Various polarizing plates were thus fabricated.

—Evaluation of Durability of Polarizing Plate—

A polarizing plate durability test was conducted in the following manner with the polarizing plate bonded to glass with an adhesive.

Two samples (about 5 cm×5 cm) were produced by bonding polarizing plates on glass such that the cellulose acylate film of Example that was obtained in Example 1 was on the side of the interface with air. Single crossed transmittance measurement was conducted with the side of the sample on which the cellulose acylate film of the example obtained in Example 1 set facing the light source. Measurement was conducted over a range of 380 nm to 780 nm with a VAP-7070 automated polarizing film measuring device made by JASCO (Ltd.). The measurement value obtained at 410 nm was adopted. The two samples were each measured and the average value was adopted as the crossed transmittance of the polarizing plate. Subsequently, the two polarizing plates were stored for 120 hours in an environment of 80° C. at a relative humidity of 90% RH. Subsequently, crossed transmittance measurement was conducted by the same method. The change in crossed transmittance before and after was calculated and evaluated as the polarizing plate durability. The relative humidity of an environment without humidity control ranged from 0 to 20% RH.

Film Nos. 112 and 116 of the examples exhibited less change in before and after crossed transmittance than Comparative Example Film No. 148 of Example 1 which did not contain the compound denoted by general formula (I). The compound denoted by general formula (I) was found to enhance polarizing plate durability.

Example 6

Fabrication of Liquid Crystal Display Device

The polarizing plate on the viewer-side of a commercial liquid-crystal television (Bravia J5000 made by Sony Corp.) was peeled off and each of the polarizing plates fabricated in the above Examples as polarizing plates of the present invention was bonded on the viewer-side with adhesive such that the polarizing plate protective film of the various above Examples was on the opposite side from the liquid crystal cell, yielding a liquid crystal display device.

Example 101

With the exception that the compounds described in Table 2 were replaced with the compounds described in Table 6 below, cellulose acylate films were fabricated and evaluated by the same methods as in Example 1.

—Haze Evaluation—

The haze in each of the films obtained in Example 101 was measured and evaluated on the following scale.

Haze measurement was conducted for each film with an "HGM-2DP" commercial haze meter (made by Suga Test Instruments Co., Ltd.) in accordance with JIS K-7136. The results are given in the table.

A: Haze of less than 0.5%
B: Haze of greater than or equal to 0.5% but less than 0.7%
C: Haze of greater than or equal to 0.7%

The results of the above are given in Table 6.

TABLE 6

| | Additive | | | Film performance | | | | | Structure of additive | | |
| --- | --- | --- | --- | --- | --- | --- | --- | --- | --- | --- | --- |
| Film No. | Compound No. | Content (wt %**) | Volatility | Surface hardness | Inhibition of light tinting | Haze | | Molecular weight | Total number of connecting groups * | Equivalent U | Remarks |
| 501 | 101-1-A 101-1-B | 10 | None | 224 | A+ | A | 0.24 | A | 406 | 2 | 203 | Ex. |
| 502 | 101-3-A 101-3-B | 10 | None | 217 | A | A | 0.20 | A | 468 | 2 | 234 | Ex. |
| 503 | 101-4-A 101-4-B | 10 | None | 215 | A | A | 0.12 | A | 460 | 2 | 230 | Ex. |
| 504 | 101-6-A 101-6-B | 10 | None | 207 | B | A | 0.25 | A | 406 | 2 | 203 | Ex. |
| 505 | 101-7-A 101-7-B | 10 | None | 192 | C | A | 0.14 | A | 462 | 2 | 231 | Ex. |
| 506 | 101-8-A 101-8-B | 10 | None | 219 | A | B | 0.21 | A | 454 | 2 | 227 | Ex. |
| 507 | 101-9-A 101-9-B | 10 | None | 228 | A+ | A | 0.14 | A | 448 | 2 | 224 | Ex. |
| 508 | 101-20 | 10 | None | 224 | A+ | A | 0.16 | A | 397 | 2 | 199 | Ex. |
| 509 | 101-24 | 10 | None | 212 | A | C | 0.20 | A | 389 | 2 | 195 | Ex. |
| 510 | 101-25 | 10 | None | 215 | A | A | 0.25 | A | 362 | 2 | 181 | Ex. |
| 511 | 102-4 | 10 | None | 216 | A | B | 0.23 | A | 341 | 2 | 171 | Ex. |
| 512 | 102-6 | 10 | None | 217 | A | A | 0.28 | A | 382 | 2 | 191 | Ex. |
| 513 | 105-1 | 10 | None | 207 | B | A | 0.20 | A | 639 | 4 | 160 | Ex. |
| 514 | 105-4 | 10 | None | 211 | B | A | 0.27 | A | 643 | 4 | 161 | Ex. |
| 515 | 105-6 | 10 | None | 216 | A | A | 0.26 | A | 687 | 4 | 172 | Ex. |
| 516 | 105-7 | 10 | None | 216 | A | A | 0.26 | A | 631 | 4 | 158 | Ex. |
| 517 | 105-10 | 10 | None | 218 | A | B | 0.27 | A | 631 | 4 | 158 | Ex. |
| 518 | 105-11 | 10 | None | 228 | A+ | A | 0.29 | A | 455 | 3 | 152 | Ex. |
| 519 | 105-12 | 10 | None | 227 | A+ | A | 0.26 | A | 489 | 3 | 163 | Ex. |
| 520 | 105-13 | 10 | None | 229 | A+ | A | 0.29 | A | 659 | 4 | 165 | Ex. |
| 521 | 105-14 | 10 | None | 226 | A+ | A | 0.25 | A | 693 | 4 | 173 | Ex. |
| 522 | Comp. Compound 101 | 5 | Present | 191 | C | D | 0.72 | B | 212 | 1 | 212 | Comp. Ex. |
| 523 | Comp. Compound 101 | 10 | Present | ※ | — | — | — | — | 212 | 1 | 212 | Comp. Ex. |
| 524 | Comp. Compound 102 | 10 | Present | ※ | — | — | — | — | 340 | 2 | 170 | Comp. Ex. |
| 525 | Comp. Compound 102 | 2 | Present | 184 | D | A | 12.20 | C | 340 | 2 | 170 | Comp. Ex. |
| 526 | Comp. Compound 103 | 10 | None | ※ | — | — | — | — | 537 | 2 | 269 | Comp. Ex. |

TABLE 6-continued

| | Additive | | | Film performance | | | Structure of additive | | | |
|---|---|---|---|---|---|---|---|---|---|---|
| Film No. | Compound No. | Content (wt %**) | Volatility | Surface hardness | Inhibition of light tinting | Haze | Molecular weight | Total number of connecting groups * | Equivalent U | Remarks |
| 527 | None | 0 | — | 180  D | A | 0.30  A | — | — | — | Comp. Ex. |

*Total number of divalent connecting group denoted by —NH—(C=O)—NR[100]— and divalent connecting group denoted by —NH—(C=O)—O— contained per molecule
**wt % is mass % of the additive relative to 100 mass % of cellulose acylate. For films for which two types of additives are indicated, the mixture obtained in the synthesis example was employed.
※ A cellulose acetate solution prepared by adding the comp. compound was not thoroughly dissolved, resulting in failure of film formation.

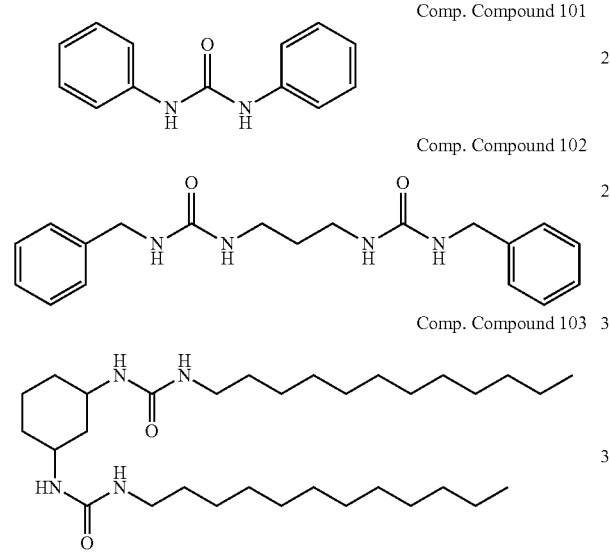

Comp. Compound 101

Comp. Compound 102

Comp. Compound 103

Comparative Compound 101 is Compound (A-26) described in JP-A-No. 2005-272566 and Comparative Compounds 102 and 103 are Compounds (53) and (35) described in JP-A-No. 2002-322294.

Each of the films of Examples exhibited less haze and greater transparency than the films of Comparative Examples. The comparative compounds, particularly Comparative Compounds 102 and 103, in which two groups denoted by —NH—CO—NH— were contained within the molecule, exhibited poor solubility in the film-forming solvent and did not readily lend themselves to the preparation of transparent cellulose acylate compositions and films. Although Comparative Compound 102 permitted the fabrication of a film with the addition of a small quantity, it exhibited a high haze value.

Further, the films of Examples exhibited high Knoop hardness. It is thought that the proton portions in the divalent linking groups denoted by —NH—CO—NR[100]— or —NH—CO—O— effectively acted on the acetyl groups and hydroxyl groups in the cellulose acylate to form hydrogen bonds which inhibited movement of the polymer chains of the cellulose acylate, which contributed to increasing the surface hardness (Knoop hardness).

The contribution of the substituent group adjacent to the divalent linking groups denoted by —NH—CO—NR[100]— or —NH—CO—O— with regard to light tinting was found to be great. All of the embodiments in which an alkylene group was bonded to such a divalent linking group exhibited good light tinting inhibiting effects (a score of A).

In Comparative Compound 101, in which two nitrogen atom were directly bonded to the benzene ring, light tinting was particularly high and the compound was found to be unpreferable as an additive for optical films. By contrast, films containing compounds in which a benzene ring was directly bonded to a nitrogen atom on just one side exhibited good light tinting inhibiting effects (scores of B and C). Further, films containing compounds in which benzene rings were not directly bonded to nitrogen atoms also exhibited good light tinting inhibiting effects.

Based on the above results, the second aspect of the present invention was determined to provide a cellulose acylate film of high surface hardness (Knoop hardness), in which light tinting was inhibited, that exhibited little haze.

Example 102

With the exceptions that the type of cellulose acylate, the types of various additives, and the thickness of the cellulose acylate film were changed as indicated in Table 7, cellulose acylate films were fabricated in the same manner as in Example 101.

The various characteristics were evaluated in the same manner as in Example 101. However, in the course of evaluating the surface hardness, the indentation load was changed to 20 mN in measuring the films that were less than or equal to 40 μm in thickness.

—Evaluation of the Surface Hardness of the Cellulose Acylate Films—

With the exception that the indentation load was changed as set forth above, the surface hardness of the cellulose acylate films obtained as set forth above was measured by the same method as that described in Example 101. The unit was denoted in N/mm².

The value of the Knoop hardness of each of the films was compared to the value of the Knoop hardness of the film fabricated without adding additives and evaluated based on the scale employed in Example 2 above.

TABLE 7

| Film No. | Cellulose acylate Degree of acetyl substitution | Additive Compound No. | Content (wt %) | Film thickness (μm) | Film performance Surface hardness | Inhibition of light tinting | Hase | Volatility | Remarks |
|---|---|---|---|---|---|---|---|---|---|
| 601 | 2.86 | 101-1-A, 101-1-B | 12 | 42 | A | A | A | None | Ex. |
| 602 | 2.86 | 101-9-A, 101-9-B | 12 | 24 | B | A | A | None | Ex. |
| 603 | 2.86 | 101-20 | 12 | 27 | A | A | A | None | Ex. |
| 604 | 2.86 | 102-6 | 12 | 32 | A | A | A | None | Ex. |
| 605 | 2.86 | Comp. compound 101 | 12 | ※ | — | — | — | Present | Comp. Ex. |

※ A cellulose acetate solution prepared by adding the comp. compound was not thoroughly dissolved, resulting in failure of film formation.
※※ For films for which two types of additives are indicated, the mixture obtained in the synthesis example was employed.

As shown in Table 7, the films of Examples exhibited good surface hardness even at thinner thickness, and inhibited light tinting and haze. Comparative Example 102 which had two groups denoted by —NH—CO—NH—, dissolved poorly in the film-forming solvent and did not lend itself readily to the fabrication of transparent cellulose acylate compositions or films.

Example 103

Fabrication of Optical Film with Hard Coat Layer

A hard coat layer 6 μm in thickness was formed by the same method as in Example 4 on the surfaces of single-layer optical films comprised of the cellulose acylates of the various Examples fabricated above, and optical films with hard coat layers were fabricated.
—Evaluation of Pencil Hardness—
The pencil hardness of each of the cellulose acylate films with hard coat layers was evaluated by the same method as in Example 4 above. As a result, each of the films to which the compound denoted by general formula (A-100) had been added as an additive was found to exhibit a good score of 3H.

Example 104

Fabrication of Polarizing Plate and Evaluation of Polarizing Plate Durability

Polarizing plates were fabricated and the durability of the polarizing plates was evaluated by the same methods as those set forth in Example 5 above using the various cellulose acylate films obtained in Example 101.
Example Film Nos. 510 and 509 exhibited less change in before and after crossed transmittance than Film No. 526, a comparative example of Example 100, which did not contain the compound denoted by general formula (A-100). The compound denoted by general formula (A-100) was thus found to enhance the polarizing plate durability.

Example 105

Fabrication of Liquid Crystal Display Device

The polarizing plate on the viewing side of a commercial liquid-crystal television (Bravia J5000 made by Sony Corp.) was peeled off and each of the polarizing plates fabricated in the above Examples was bonded on the viewer-side with adhesive such that the polarizing plate protective film of the various above Examples was on the opposite side from the liquid crystal cells, yielding a liquid crystal display device.

EXPLANATION OF THE SYMBOLS

1 Cellulose acylate film according to an aspect of the present invention
2 Polarizer
3 Phase-difference film
4 Liquid crystal cell
10 Upper polarizing plate

What is claimed is:
1. A cellulose acylate film,
which comprises a compound denoted by general formula (I) below,
wherein the equivalent U of the compound, which is calculated as a value obtained by dividing the molecular weight of the compound by the number of divalent linking groups denoted by —O—C(=O)—NH—contained per molecule, is less than or equal to 515:

$$Q^1\text{-}(L^{12}\text{-}L^{11})_{n1}\text{-O—C(=O)—NH-}(L^{21}\text{-}L^{22})_{n2}\text{-}Q^2 \quad \text{General formula (I)}$$

wherein, in general formula (I),
each of $L^{11}$ and $L^{21}$ independently denotes an optionally substituted alkylene group;
each of $L^{12}$ and $L^{22}$ independently denotes a single bond, any one of or any combination of —O—, —NR$^1$—, —S—, and —C(=O)—;
$R^1$ denotes a hydrogen atom or a substituent;
each of n1 and n2 independently denotes an integer of 0 to 20, with at least either n1 or n2 being an integer of greater than or equal to 1;
when $L^{11}$, $L^{12}$, $L^{21}$, and $L^{22}$ are present in a plurality of number, the plurality of $L^{11}$, $L^{12}$, $L^{21}$, and $L^{22}$ can be identical or different;
and each of $Q^1$ and $Q^2$ independently denotes a substituent, with at least either $Q^1$ or $Q^2$ comprising a ring structure.

2. The cellulose acylate film according to claim 1, wherein the compound denoted by general formula (I) comprises 1 to 6 divalent linking groups denoted by —O—C(=O)—NH— per molecule.

3. The cellulose acylate film according to claim 1, wherein the molecular weight of the compound denoted by general formula (I) ranges from 230 to 2,000.

4. The cellulose acylate film according to claim 1, wherein the compound denoted by general formula (I) is a compound denoted by general formula (I-1) below:

$(Q^3-(L^{32}-L^{31})_{n3}-A-(L^{41}-L^{42})_{n4})_m-Z^1$  General formula (I-1):

wherein, in general formula (I-1),
each of $L^{31}$ and $L^{41}$ independently denotes an optionally substituted alkylene group;
each of $L^{32}$ and $L^{42}$ independently denotes a single bond, any one of or any combination of —O—, —NR$^1$—, —S—, and —C(=O)—;
$R^1$ denotes a hydrogen atom or a substituent;
each of n3 and n4 independently denotes an integer of 0 to 20, with at least either n3 or n4 being an integer of greater than or equal to 1;
when $L^{31}$, $L^{32}$, $L^{41}$, and $L^{42}$ in a plurality of number, the plurality of $L^{31}$, $L^{32}$, $L^{41}$, and $L^{42}$ can be identical or different;
$Q^3$ denotes a substituent;
$Z^1$ denotes a linking group of valence m;
A denotes *—O—C(=O)—NH— or *—NH—C(=O)—O—, where * denotes a position of a bond with $L^{41}$; m denotes an integer of 2 to 6;
when $Q^3$ and A are present in a plurality of number, the plurality of $Q^3$ and A can be identical or different; with at least either $Q^3$ or $Z^1$ comprising a ring structure.

5. The cellulose acylate film according to claim 4, wherein, at least either $Q^3$ or $Z^1$ in the compound denoted by general formula (I-1) comprises a ring structure, and the compound denoted by general formula (I-1) has 2 or 3 ring structures per molecule.

6. The cellulose acylate film according to claim 4, wherein, in general formula (I-1), at least one of the plurality of $Q^3$ comprises an aromatic group, or $Z^1$ comprises an alicyclic group or aromatic group.

7. The cellulose acylate film according to claim 4, wherein, in general formula (I-1), at least one of the plurality of $Q^3$ comprises an aromatic group, or $Z^1$ comprises a alicyclic group.

8. The cellulose acylate film according to claim 1, wherein the compound denoted by general formula (I) is a compound denoted by general formula (I-2) below:

$(Q^4-(L^{52}-L^{51})_{n5}-A-(L^{61}-L^{62})_{n6})_{m1}-Z^2$  General formula (I-2):

wherein, in general formula (I-2),
each of $L^{51}$ and $L^{61}$ independently denotes an optionally substituted alkylene group;
each of $L^{52}$ and $L^{62}$ independently denotes a single bond, or any one of or any combination of —O—, —NR$^1$—, —S—, and —C(=O)—;
$R^1$ denotes a hydrogen atom or a substituent;
each of n5 and n6 independently denotes an integer of 0 to 20, with at least either n5 or n6 being an integer of greater than or equal to 1;
when $L^{51}$, $L^{52}$, $L^{61}$, and $L^{62}$ are present in a plurality of number, the plurality of $L^5$, $L^{52}$, $L^{61}$, and $L^{62}$ can be identical or different;
$Q^4$ denotes a substituted or unsubstituted phenyl group, substituted or unsubstituted cyclohexyl group, methyl group, or t-butyl group;
$Z^2$ denotes a group comprising at least one or any combination of linear, branched, or alicyclic group and aromatic group;
A denotes *—O—C(=O)—NH— or *—NH—C(=O)—O—, where * denotes a position of a bond with $L^{61}$; m1 denotes the integer 2 or 3;
when $Q^4$ and A are present in a plurality of number, the plurality of $Q^4$ and A can be identical or different; with at least one from among $Z^2$ and the plurality of $Q^4$ comprising a ring structure.

9. The cellulose acylate film according to claim 8, wherein, in general formula (I-2), $Q^4$ is an unsubstituted phenyl group.

10. The cellulose acylate film according to claim 1, wherein the compounded denoted by general formula (I) is selected from the group consisting of a compound denoted by general formula (II) below and a compound denoted by general formula (III) below:

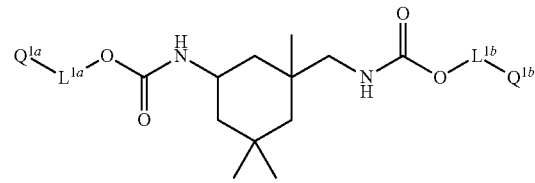

General formula (II)

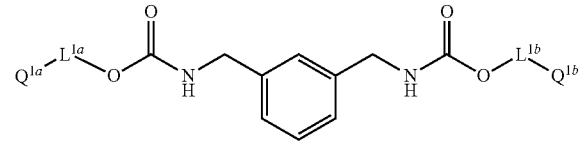

General formula (III)

wherein, in general formulas (II) and (III),
each of $L^{1a}$ and $L^{1b}$ independently denotes a single bond, an alkylene group, one of groups denoted by general formulas (2A) to (2E) below, or a group comprised of a combination of one or more groups denoted by general formulas (2A) to (2E) and one or more alkylene groups;
each of $Q^{1a}$ and $Q^{1b}$ independently denotes a substituent, with at least either $Q^{1a}$ or $Q^{1b}$ denoting a phenyl group optionally substituted with an alkoxy group having 1 to 3 carbon atoms or an alkyl group having 1 to 3 carbon atoms;

—{$R^b_{jb}$(CR$^a$R$^c$)$_{ja}$—O—(C=O)}—*;  General formula (2A)

—{$R^b_{jb}$(CR$^a$R$^c$)$_{ja}$—O}—*;  General formula (2B)

—{$R^b_{jb}$(CR$^a$R$^c$)$_{ja}$—(C=O)O—}—*;  General formula (2C)

—{$R^b_{jb}$(CR$^a$R$^c$)$_{ja}$—NR$^1$(C=O)O—}—*;  General formula (2D)

—{$R^b_{jb}$(CR$^a$R$^c$)$_{ja}$—O—(C=O)NR$^1$}—*;  General formula (2E)

wherein, in general formulas (2A) to (2E),
* denotes a position of a bond with $Q^{1a}$ or $Q^{1b}$, or a position of a bond with an adjacent group on the $Q^{1a}$ or $Q^{1b}$ side;
each of $R^a$ and $R^c$ independently denotes a hydrogen atom or an alkyl group having 1 to 3 carbon atoms;
ja denotes an integer that is greater than or equal to 1;
when $R^a$ and $R^c$ are present in a plurality of number, the plurality of $R^a$ and $R^c$ can be identical or different;
$R^b$ denotes a cycloalkylene group optionally substituted with one or more alkyl groups having 1 to 3 carbon atoms;
jb denotes 0 or 1;
and $R^1$ denotes a hydrogen atom or an alkyl group having 1 to 4 carbon atoms;

when $R^1$ are present in a plurality of number, the plurality of $R^1$ can be identical or different.

11. The cellulose acylate film according to claim 1, which comprises the compound denoted by general formula (I) in a quantity of 0.1 to 50 mass parts per 100 mass parts of cellulose acylate.

12. A polarizing plate, which comprises the cellulose acylate film according to claim 1 and a polarizer.

13. A liquid crystal display device, which comprises the polarizing plate according to claim 12.

14. The liquid crystal display device according to claim 13, wherein the polarizing plate is provided on at least a viewer-side of the liquid crystal display device.

15. A compound denoted by general formula (II-1) below:

General formula (II-1)

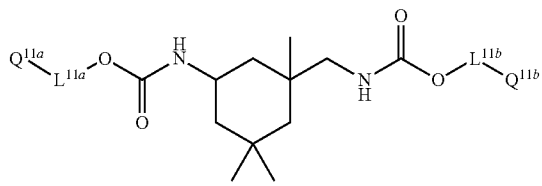

wherein, in general formula (II-1),
each of $L^{11a}$ and $L^{11b}$ independently denotes any one of groups denoted by general formulas (2A-1) to (2E-1) below, a group comprising a combination of two or more groups denoted by general formulas (2A-1) to (2E-1) below, or a group comprising a combination of one or more groups denoted by general formulas (2A-1) to (2E-1) below and one or more alkylene groups;
each of $Q^{11a}$ and $Q^{11b}$ independently denotes a substituent, with at least either $Q^{11a}$ or $Q^{11b}$ denoting a phenyl group optionally substituted with an alkoxy group having 1 to 3 carbon atoms or an alkyl group having 1 to 3 carbon atoms:

—{$(CR^aR^c)_{ja}$—O—(C=O)}—*;  General formula (2A-1)

—{$(CR^aR^c)_{ja}$—O}—*;  General formula (2B-1)

—{$(CR^aR^c)_{ja}$—(C=O)O—}—*;  General formula (2C-1)

—{$(CR^aR^c)_{ja}$—$NR^1$(C=O)O—}—*;  General formula (2D-1)

—{$(CR^aR^c)_{ja}$—O—(C=O)$NR^1$}—*;  General formula (2E-1)

wherein, in general formulas (2A-1) to (2E-1),
* denotes a position of a bond with $Q^{11a}$ or $Q^{11b}$, or a position of a bond with an adjacent group on the $Q^{11a}$ or $Q^{11b}$ side;
each of $R^a$ and $R^c$ independently denotes a hydrogen atom or an alkyl group having 1 to 3 carbon atoms;
$R^1$ denotes a hydrogen atom or an alkyl group having 1 to 4 carbon atoms;
ja denotes an integer greater than or equal to 1;
when $R^a$, $R^c$, and $R^1$ are present in a plurality of number, the plurality of $R^a$, $R^c$, and $R^1$ can be identical or different.

16. A compound denoted by general formula (III-1) below:

General formula (III-1)

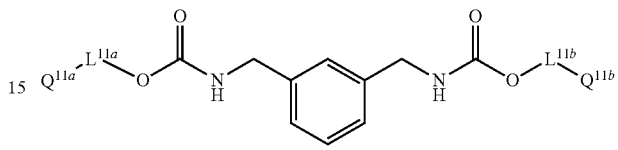

wherein, in general formula (III-1),
each of $L^{11a}$ and $L^{11b}$ independently denotes any one of groups denoted by general formulas (2A-1) or (2C-1) to (2E-1) below, a group comprising a combination of two or more groups denoted by general formulas (2A-1) or (2C-1) to (2E-1) below, or a group comprising a combination of one or more groups denoted by general formulas (2A-1) or (2C-1) to (2E-1) below and one or more alkylene groups;
each of $Q^{11a}$ and $Q^{11b}$ independently denotes a substituent, with at least $Q^{11a}$ or $Q^{11b}$ denoting a phenyl group optionally substituted with an alkoxy group having 1 to 3 carbon atoms or an alkyl group having 1 to 3 carbon atoms:

—{$(CR^aR^c)_{ja}$—O—(C=O)}—*;  General formula (2A-1)

—{$(CR^aR^c)_{ja}$—(C=O)O—}—*;  General formula (2C-1)

—{$(CR^aR^c)_{ja}$—$NR^1$(C=O)O—}—*;  General formula (2D-1)

—{$(CR^aR^c)_{ja}$—O—(C=O)$NR^1$}—*;  General formula (2E-1)

wherein, in general formulas (2A-1) and (2C-1) to (2E-1),
* denotes a position of a bond with $Q^{11a}$ or $Q^{11b}$, or a position of a bond with an adjacent group on the $Q^{11a}$ or $Q^{11b}$ side;
each of $R^a$ and $R^c$ independently denotes a hydrogen atom or an alkyl group having 1 to 3 carbon atoms;
ja denotes an integer greater than or equal to 1;
$R^1$ denotes a hydrogen atom or an alkyl group having 1 to 4 carbon atoms;
when $R^a$, $R^c$, and $R^1$ are present in a plurality of number, the plurality of $R^a$, $R^c$, and $R^1$ can be identical or different.

* * * * *